US008792968B2

(12) United States Patent
Xiao et al.

(10) Patent No.: US 8,792,968 B2
(45) Date of Patent: Jul. 29, 2014

(54) SYSTEM AND METHOD FOR HEALTH EVALUATION

(76) Inventors: Song Xiao, Beijing (CN); Pei Si Cai, Beijing (CN); Jun Yang, Beijing (CN); Xiu Fang Deng, Beijing (CN); Ying Jie Wu, Cedar Knolls, NJ (US)

( * ) Notice: Subject to any disclaimer, the term of this patent is extended or adjusted under 35 U.S.C. 154(b) by 1265 days.

(21) Appl. No.: 11/903,300

(22) Filed: Sep. 21, 2007

(65) Prior Publication Data

US 2008/0077019 A1    Mar. 27, 2008

Related U.S. Application Data

(60) Provisional application No. 60/847,155, filed on Sep. 25, 2006, provisional application No. 60/847,333, filed on Sep. 25, 2006.

(51) Int. Cl.
*A61B 6/00* (2006.01)
*A61B 5/01* (2006.01)
*G06T 7/00* (2006.01)

(52) U.S. Cl.
CPC *A61B 5/01* (2013.01); *G06T 7/0012* (2013.01)
USPC .......................................... 600/474; 382/128

(58) Field of Classification Search
USPC ............................ 600/474; 348/164; 382/118
See application file for complete search history.

(56) References Cited

U.S. PATENT DOCUMENTS

| | | | | |
|---|---|---|---|---|
| 4,428,382 A * | 1/1984 | Walsall et al. | ................ | 600/549 |
| 5,803,082 A | 9/1998 | Stapleton et al. | | |
| 5,865,743 A * | 2/1999 | Godik | ........................... | 600/407 |
| 6,023,637 A | 2/2000 | Liu et al. | | |
| 6,442,419 B1 | 8/2002 | Chu et al. | | |
| 6,618,608 B1 * | 9/2003 | Watkins et al. | ............... | 600/412 |
| 6,975,898 B2 | 12/2005 | Seibel | | |
| 7,027,621 B1 * | 4/2006 | Prokoski | ....................... | 382/118 |
| 2004/0242976 A1 * | 12/2004 | Abreu | .......................... | 600/315 |
| 2005/0020924 A1 * | 1/2005 | Mitra | ............................. | 600/474 |
| 2006/0142661 A1 | 6/2006 | Demos et al. | | |
| 2006/0161063 A1 * | 7/2006 | Shau | ............................. | 600/504 |

OTHER PUBLICATIONS

Ablameyko, S. et al, Automatic/Interactive Interpretation of Color Map Images, Proceedings of International Conference on Signal Processing 2000, pp. 1269-1272, vol. 2.*
Chen, Kuo-Gen, Electrical Properties of Meridians, IEEE Engineering in Medicine and Biology, May/Jun. 1996, pp. 58-63.*
Hunold, S. et al, Thermographic studies on patterns of skin temperature after exercise, European Journal of Applied Physiology, 65, p. 550-554, (1992).*

* cited by examiner

*Primary Examiner* — Unsu Jung
*Assistant Examiner* — Daniel Huntley
(74) *Attorney, Agent, or Firm* — The Patel Law Firm, PC; Natu J. Patel

(57) ABSTRACT

A system, an apparatus and a method for human health evaluation utilizing Thermal Micro Texture (TMT) mapping technology is disclosed. The method comprises scanning body areas of a patient utilizing an infrared camera, detecting abnormalities in the body of the patient, analyzing abnormalities of the patient against information stored in a database, and reporting results to the patient in a pre-determined format. The method provides an earlier discovery of disease by mapping and analyzing abnormal temperatures changes in the body, which can help prevent the disease from progressing at an early stage.

33 Claims, 80 Drawing Sheets

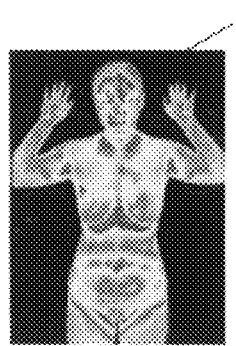 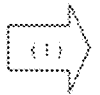 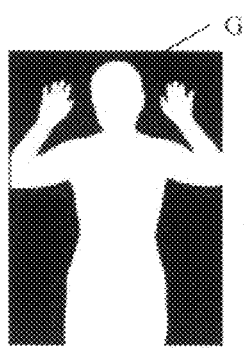  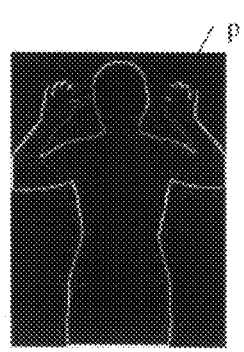
FIG. 13A  FIG. 13B  FIG. 13C

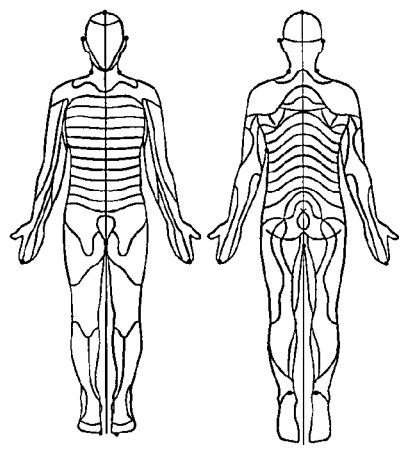 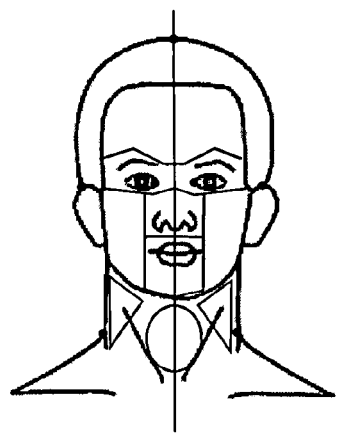
FIG. 17A   FIG. 17B   FIG. 18

550O
550P
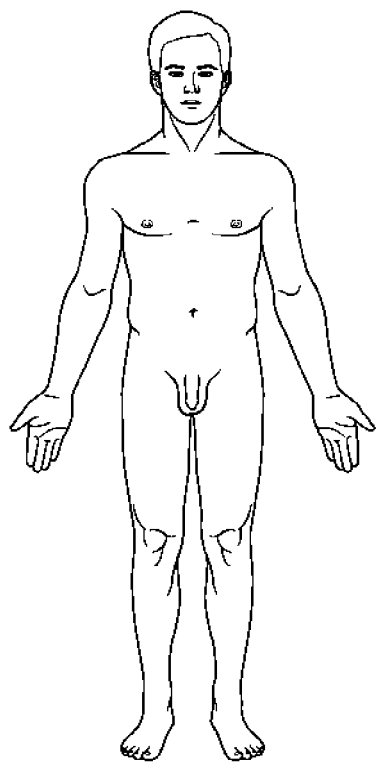
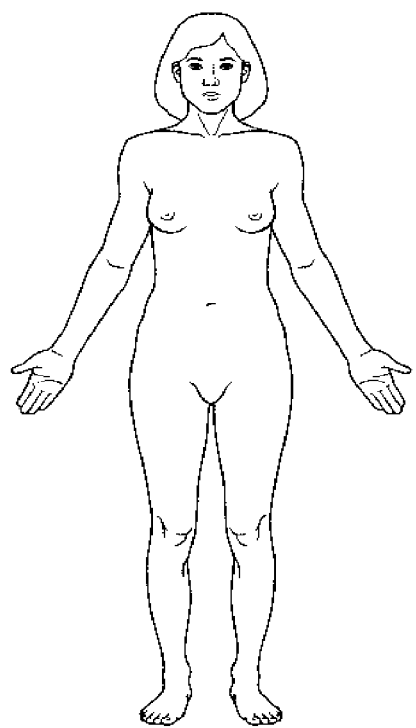
FIG. 21O
FIG. 21P

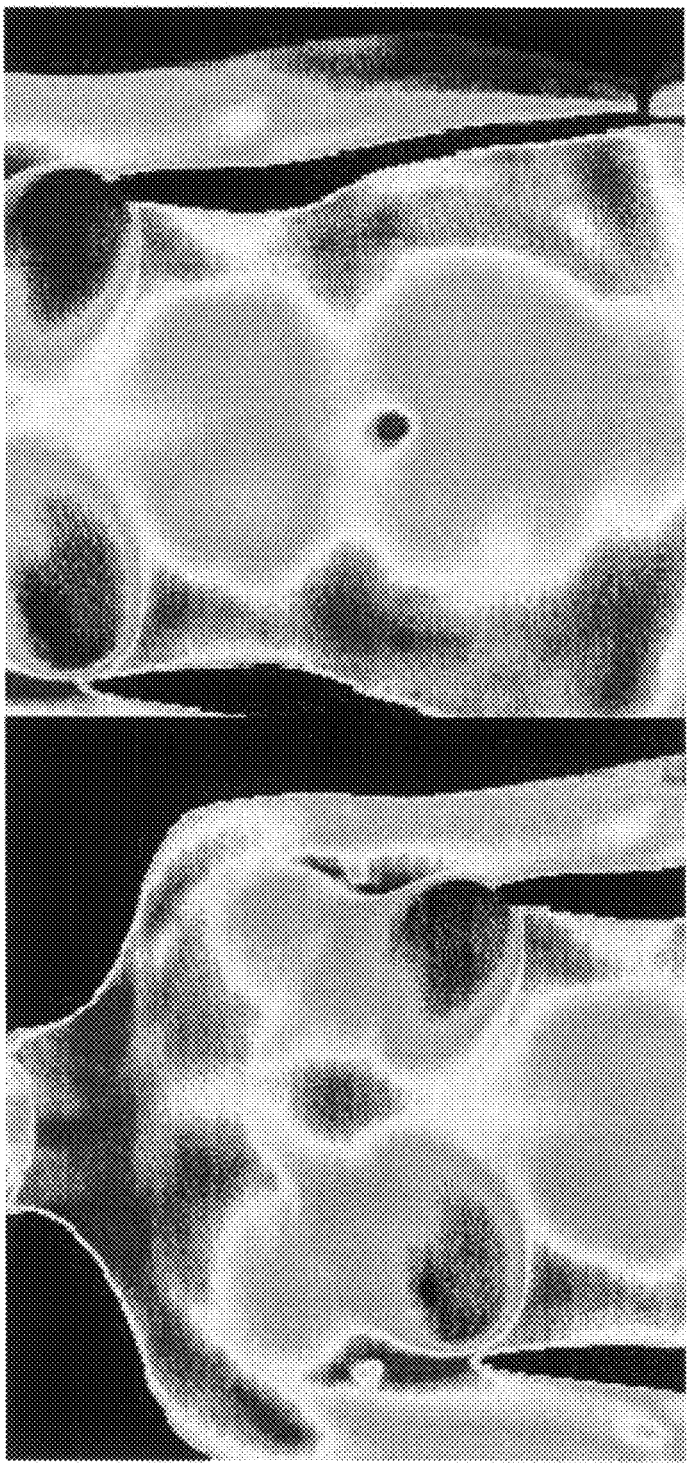

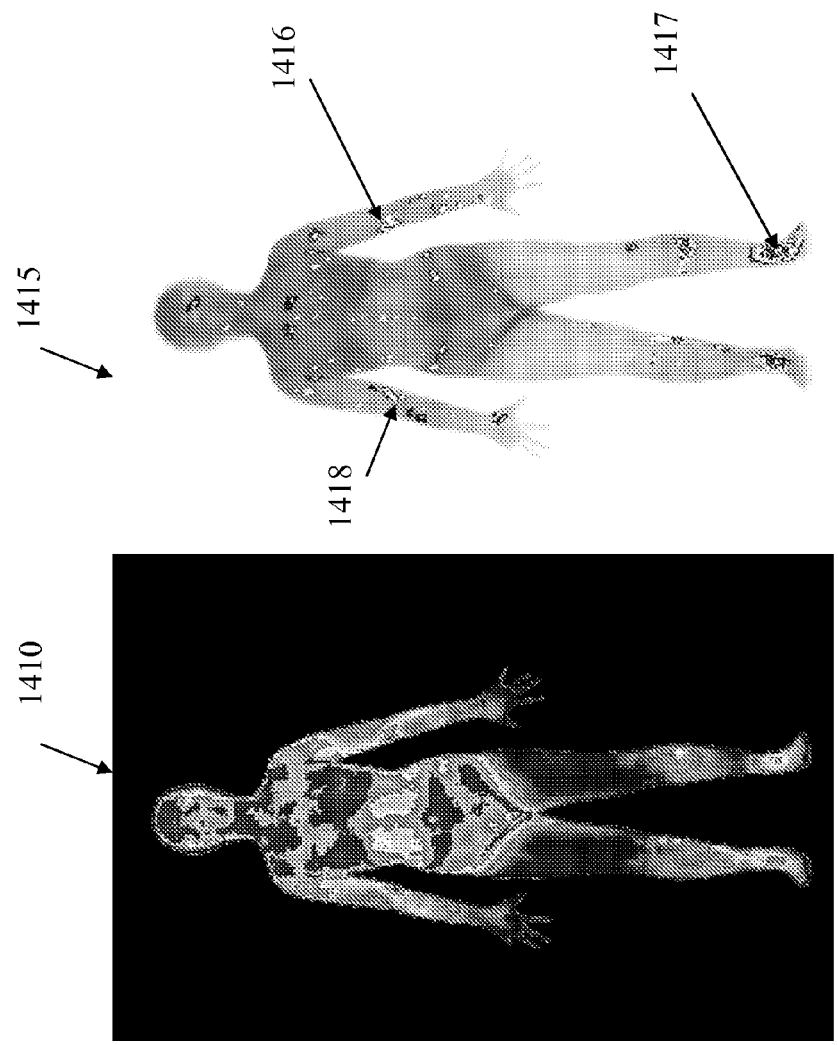

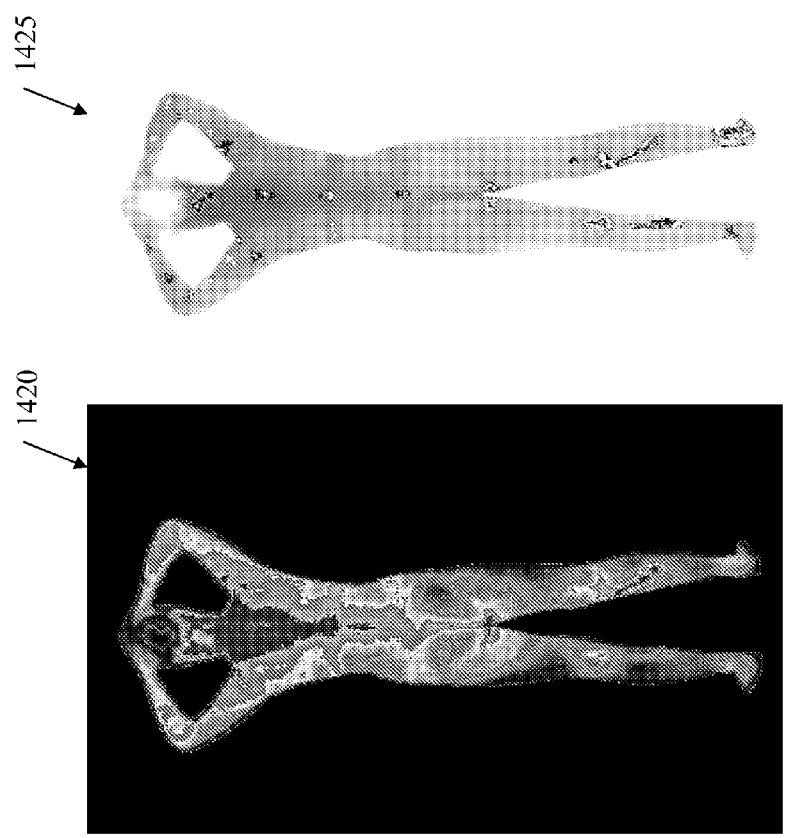

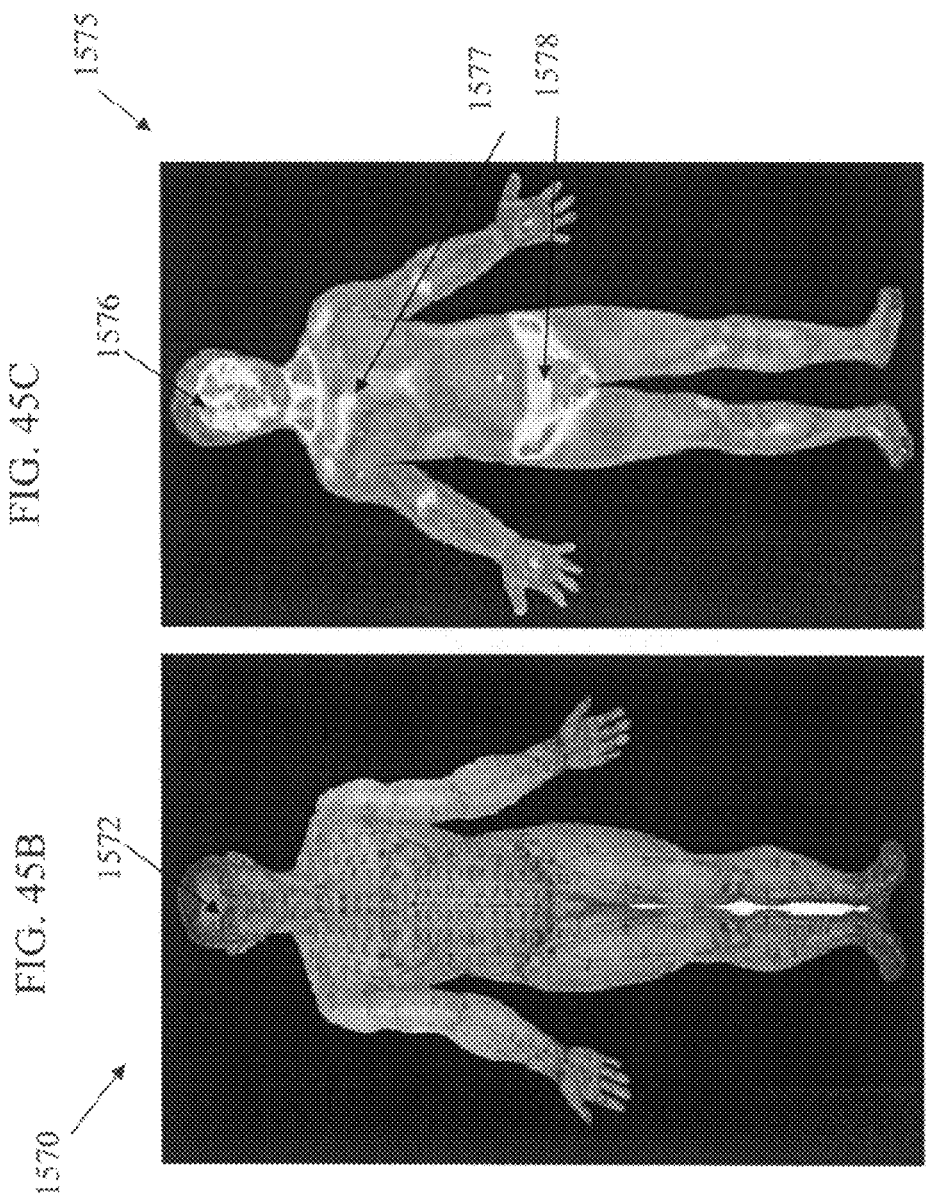

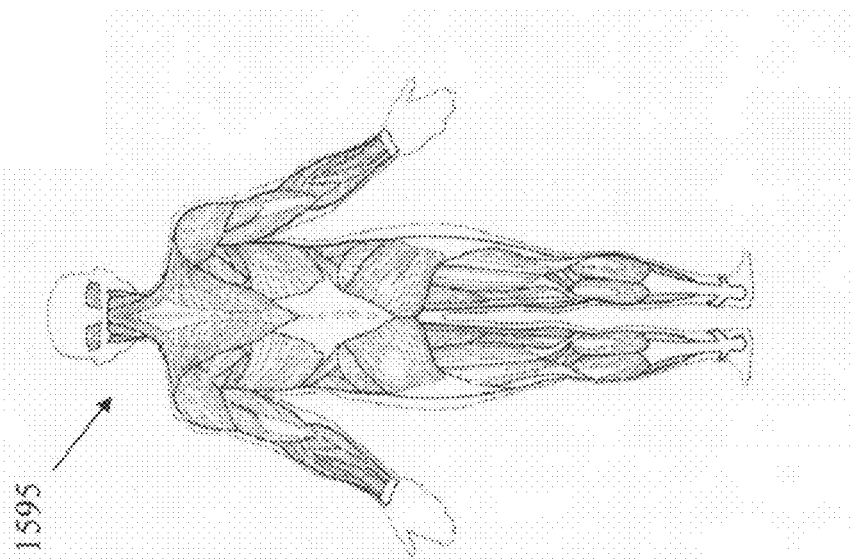
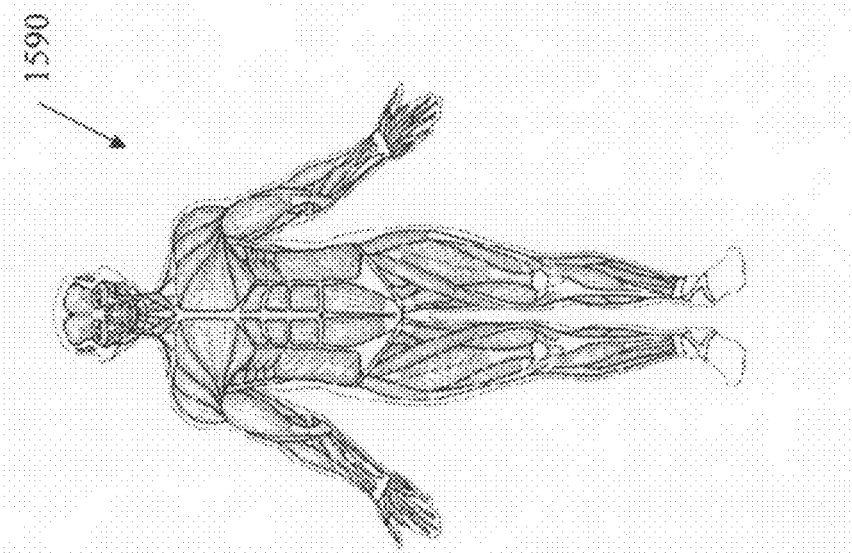
FIG. 46A
FIG. 46B

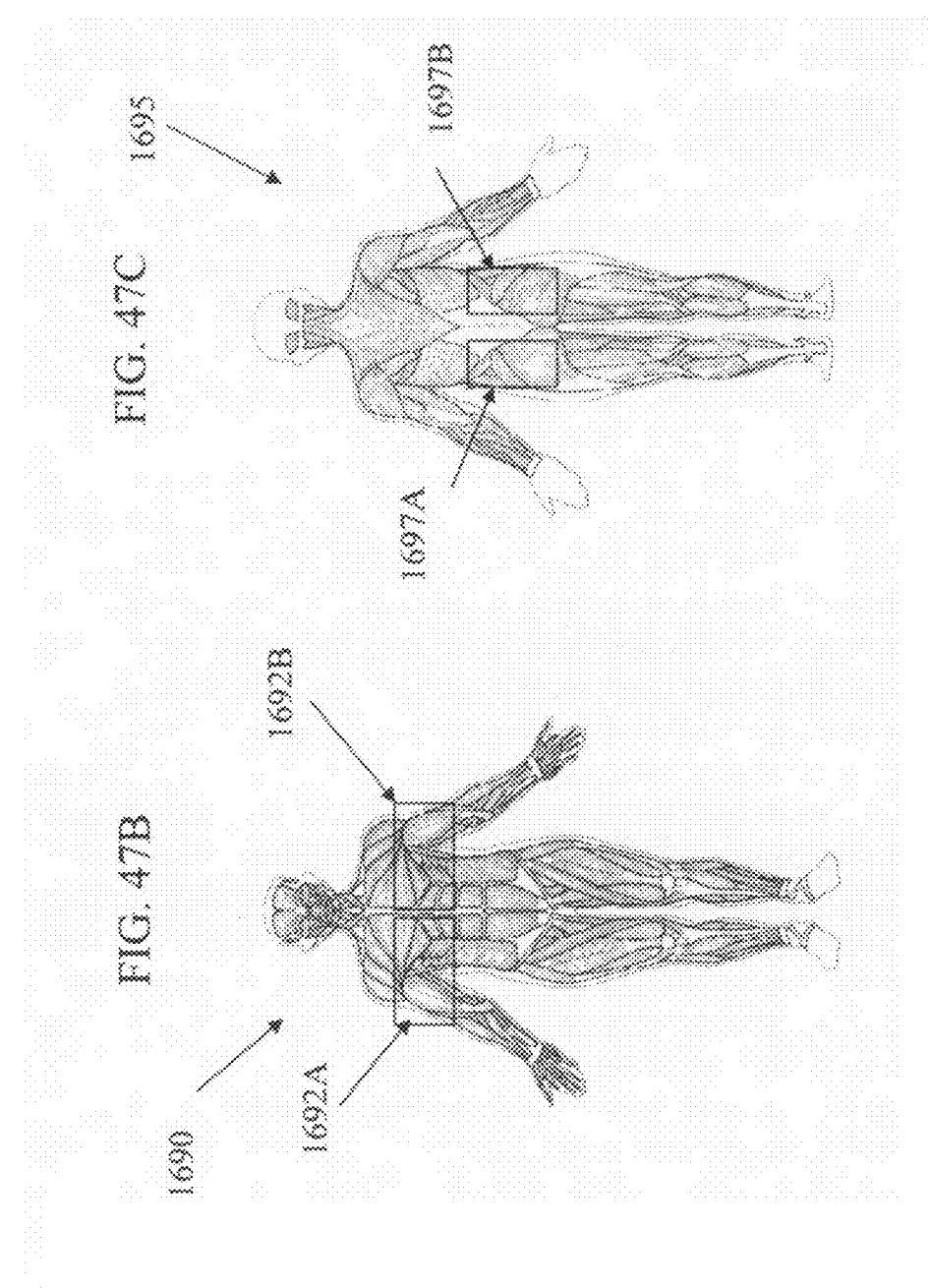

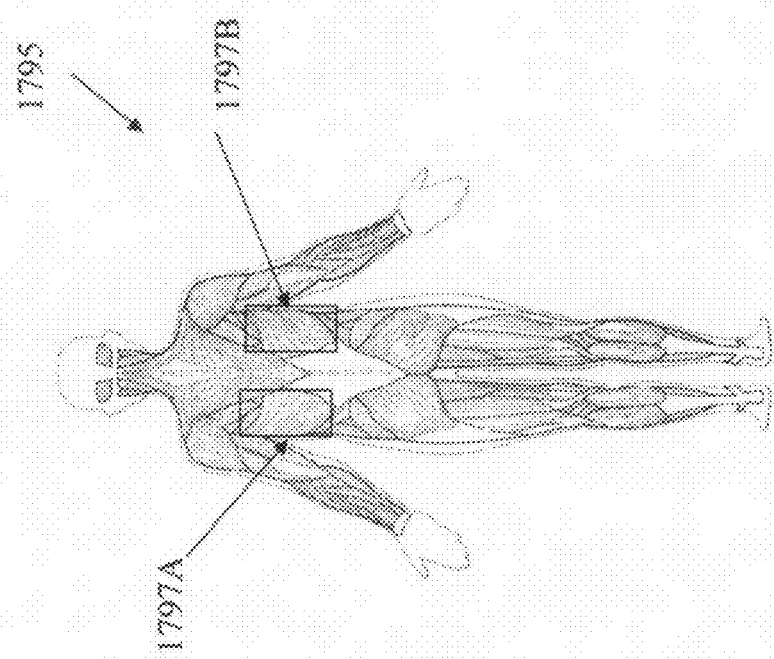
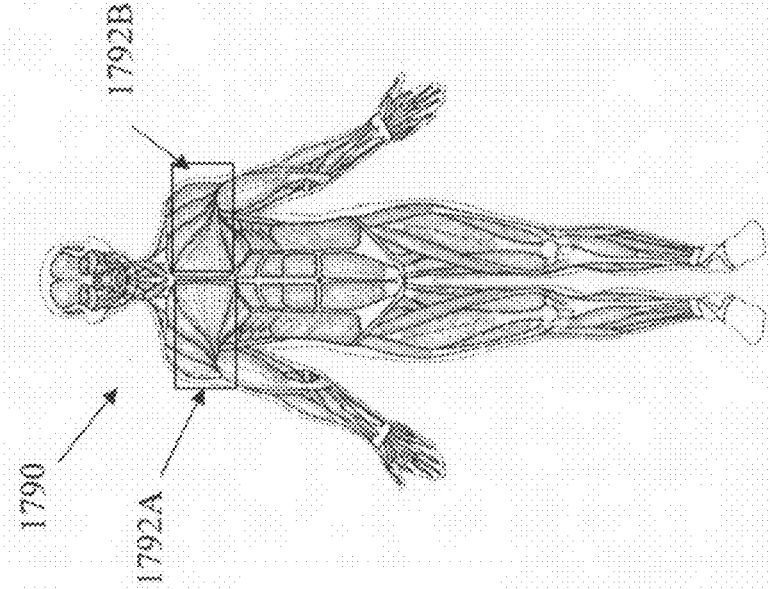

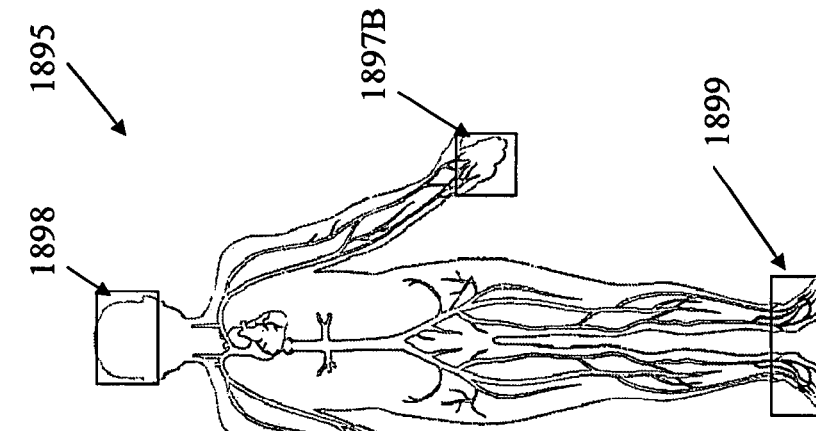
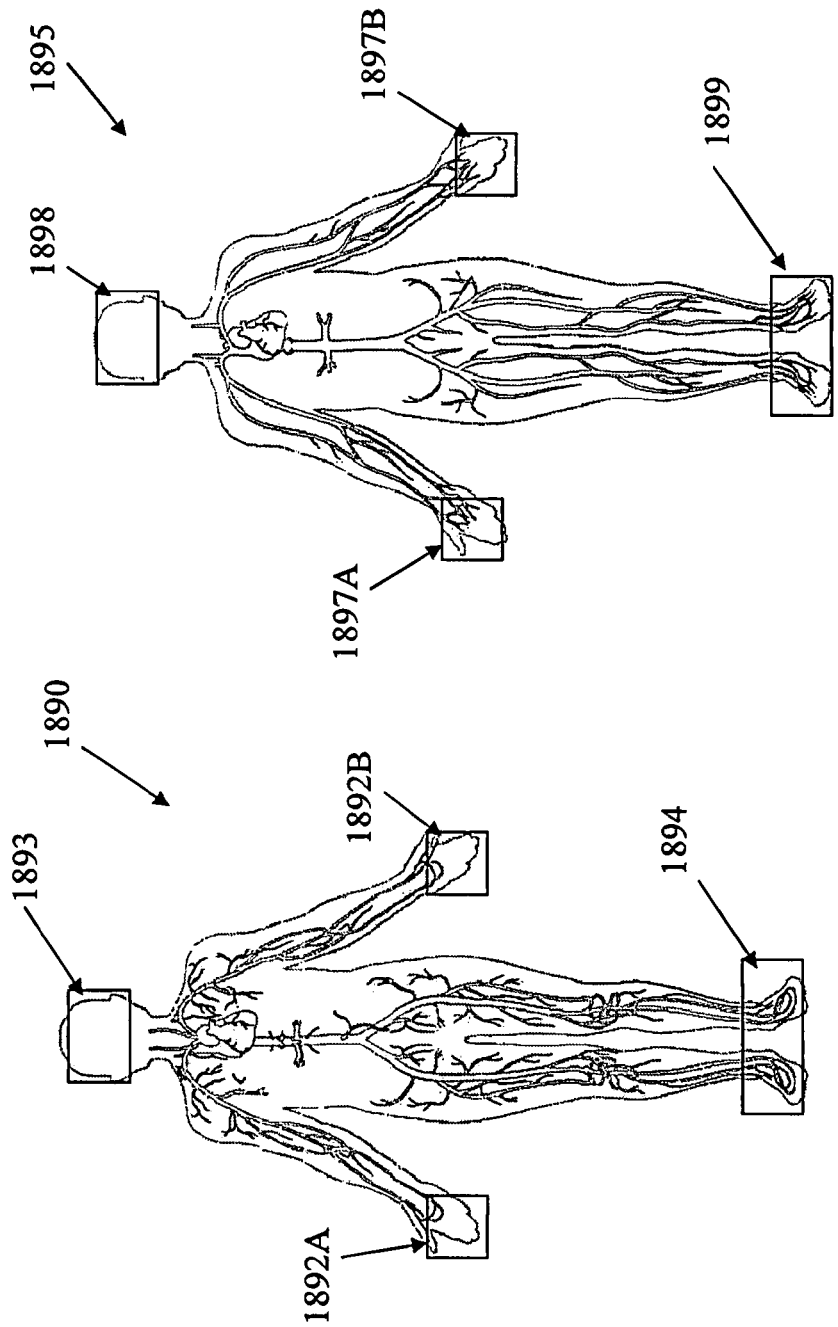

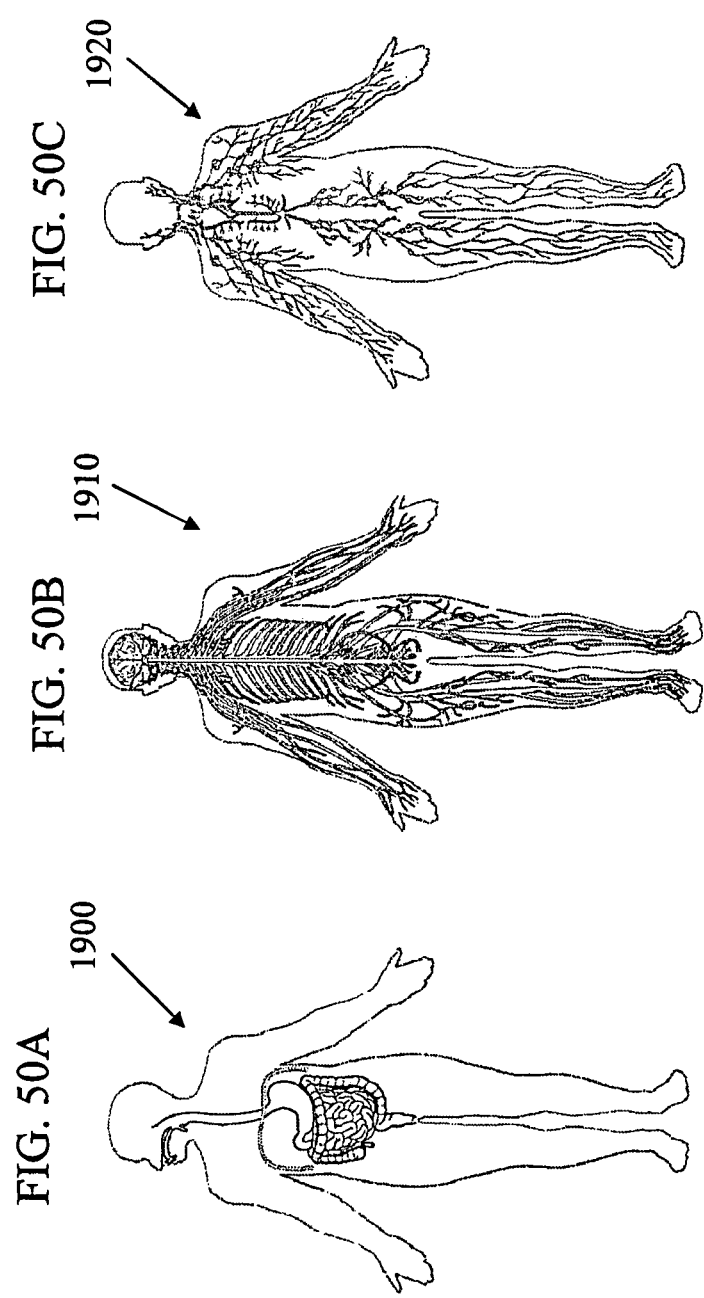

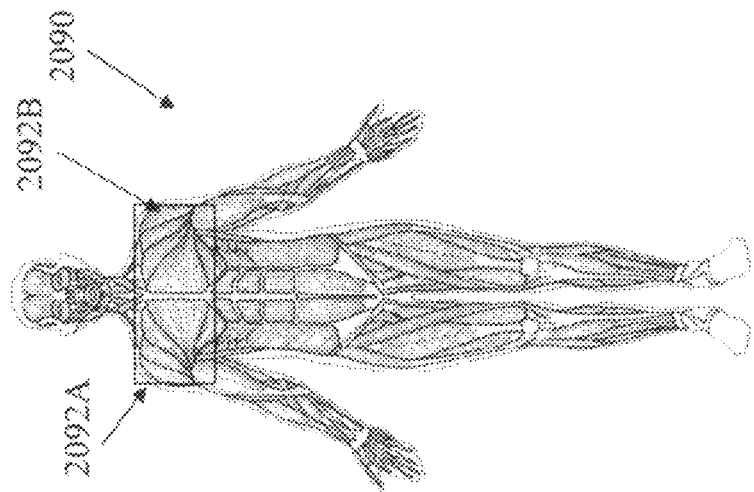

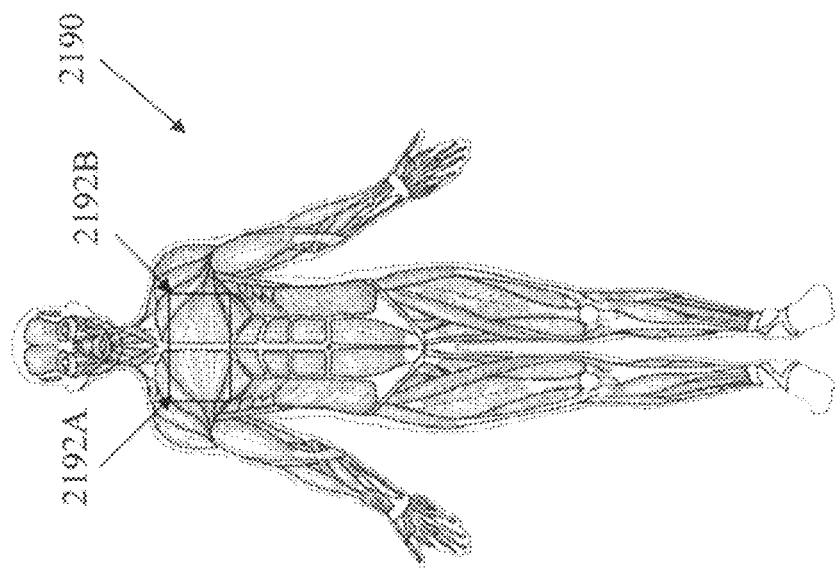

SYSTEM AND METHOD FOR HEALTH EVALUATION

CROSS-REFERENCE TO RELATED APPLICATIONS

This utility patent application claims the priority benefit of U.S. provisional patent application entitled "System and Method For Health Evaluation" by the same inventors, filed Sep. 25, 2006, Ser. No. 60/847,155, and provisional patent application entitled "System and Method for Human Health Evaluation Utilizing Thermal Micro Texture Mapping Technology" filed also on Sep. 25, 2006, Ser. No. 60/847,333, both of which are incorporated herein in their entirety by reference as if set forth in full below.

COPYRIGHT NOTICE

A portion of the disclosure of this patent application contains material that is subject to copyright protection. The copyright owner has no objection to the facsimile reproduction by anyone of the patent application or the patent disclosure, as it appears in the Patent and Trademark Office patent file or records, but otherwise reserves all copyright rights whatsoever.

BACKGROUND OF THE INVENTION

CAT scans, MRIs, and other traditional diagnostic techniques use X-rays, which are harmful to the human body. High energy radiation X-rays emitted by CAT scans and MRIs that are used to diagnose diseases cause damage to cells in the body. The risk of developing cancer from one X-ray procedure may be low, but the risk increases with each subsequent X-ray test a patient undergoes. Additionally, CAT scans and MRIs have limitations when used to diagnose diseases. Although these procedures are used to identify structural physical changes in the body, they are often not capable of diagnosing a disease when it is in its early stage.

SUMMARY OF THE INVENTION

The human health evaluation system utilizing Thermal Micro Texture (TMT) mapping technology, according to the present invention, departs from the conventional concepts and designs of the prior art, and in doing so, provides a means to detect structural physical changes and functional physiological changes in the body to provide an earlier discovery of a disease by mapping and analyzing abnormal temperatures changes in the body. In one embodiment, human health evaluation system (hereinafter referred to as "TMT system" or "health evaluation system") utilizes TMT mapping technology for diagnosing human illness at an early stage without exposing a patient to harmful rays.

In one embodiment, a health evaluation system includes a thermal imaging device to capture a thermal image of a human anatomy and a medical analysis rules library database for storing a set of rules to perform a thermal mapping and automatic zoning analysis. The database includes significant number of patients' clinical data files, which provide a stable platform for comparison and analysis. The system also includes a processor, wherein the processor is coupled to the thermal imaging device and configured to apply the thermal mapping and automatic zoning analysis to the thermal image to create thermal zones and to calculate a temperature distribution for each thermal zone. The processor is further configured to automatically evaluate and determine a health condition of the human anatomy based on a comparison between the temperature distribution for each thermal zone and at least one of a particular temperature range, a distribution, and a corresponding symmetry to said each thermal zone. The processor is configured to utilize thermal mapping and vectorization techniques. The processor is further configured to evaluate a human respiratory system abnormalities, otorhinolaryngological abnormalities, cardiovascular system abnormalities, reproductive system abnormalities, respiratory system abnormalities, digestive system abnormalities, urinary system abnormalities, endocrine system abnormalities, and lymphatic system abnormalities.

In another embodiment, an apparatus for a human health evaluation is disclosed wherein the apparatus includes means for capturing a thermal image of a human anatomy, means for applying thermal mapping and automatic zoning analysis to the thermal image to create thermal zones, means for calculating a temperature distribution for each thermal zone, and means for automatically evaluating and determining the health condition of the human anatomy based on a comparison between the temperature distribution for each thermal zone and predefined criteria for evaluation selected from a medical analysis rules library database to said each thermal zone. The apparatus further includes means for generating and displaying three-dimensional (3D) results related to the human anatomy to help diagnose a human illness.

In one embodiment, a computer program product is disclosed. The computer program product includes a computer readable medium having instructions for causing a computer to receive a thermal image of a human anatomy, to apply a thermal mapping and automatic zoning analysis to the thermal image to create thermal zones, calculate a temperature distribution for each thermal zone, and automatically evaluate and determine a health condition of the human anatomy based on a comparison between the temperature distribution for each thermal zone and at least one of a particular temperature range, a distribution, and a corresponding symmetry, from a medical analysis rules library database to said each thermal zone.

In another embodiment, a system and method for health evaluation utilizing TMT mapping technology is disclosed. The health evaluation system includes a client system, a centralized database for storing information, and a server system configured to be coupled to the client system and the centralized database. The server system is further configured to measure temperature data at various points of a patient's body utilizing an infrared camera, to process temperature data, and to map and analyze temperature data against information stored in the centralized database. The system is further capable of reporting results in a predetermined format including clinical information, thermal images and all corresponding analysis relating to the thermal images. The server system includes a medical records management module, an image collection management module, an image processing and analysis module, a report output module, a thermal image comparison module, and a cascade chromatography module.

The software utilized in the health evaluation system includes various independent yet integrated modules. The software is capable of managing a patient's medical records, analyzing, printing and storing the patient's thermal images, comparing the patient's thermal images to other patients' information stored in the database, and converting static thermal images into dynamic thermal images through cascade chromatography.

The health evaluation system produces three dimensional data and images. The different colors represent different temperature areas of the human body or parts of the body that are scanned. The health evaluation system is capable of scanning more than the surface area of a patient. The TMT mapping technology identifies abnormal heat sources deep within the body, including abnormalities from tissues and organs, blood vessels, and heat sources under hair, which help pin-point a location and cause of an illness or disease.

In one embodiment, a method for evaluating human health utilizing TMT mapping technology includes the steps of scanning body areas of a patient utilizing an infrared camera, detecting abnormal temperature changes in the body of the patient, mapping and analyzing abnormal temperature changes in the body of the patient against information stored in a centralized database, evaluating health condition of the patient, and reporting results to the patient in a pre-determined format. Another embodiment includes capturing a thermal image of a selected human anatomy area of a patient, applying a thermal mapping and automatic zoning analysis to the thermal image to create thermal zones, calculating a temperature distribution for each thermal zone, and automatically evaluating and determining the health condition of the patient based on a comparison between the temperature distribution for each thermal zone and at least one of a particular temperature range, a distribution, and a corresponding symmetry, from a medical analysis rules library database to said each thermal zone.

In yet another embodiment, a computer program for fitness evaluation embodied on a computer readable medium is disclosed. The computer program is capable of evaluating human fitness by performing a Qi (flow) evaluation process, a thermal muscle metabolism evaluation process, a fat mapping evaluation process, a thermal microcirculation metabolism evaluation process, an anatomical structures and systems evaluation process, a muscle endurance evaluation process, and a psychological evaluation process.

BRIEF DESCRIPTION OF THE DRAWING

To the accomplishment of the above and related objects, the invention may be embodied in the form illustrated in the accompanying drawings, attention being called to the fact, however, that the drawings are illustrative only and that changes may be made in the specific construction and method illustrated:

FIG. 13A illustrates an example of an infrared thermal image;

FIG. 13B illustrates an example of the human body in the infrared thermal image of FIG. 13A removed;

FIG. 13C illustrates an example of an outline created of the human body in the infrared thermal image of FIG. 13A;

FIGS. 17A and 17B illustrate innervation-based zoning templates for a front and back of the human anatomy;

FIG. 18 illustrates a facial zoning template;

FIGS. 37A and 37B illustrate thermal images of a healthy woman;

FIG. 38A illustrates a representation of a vectorized thermal image;

FIG. 38B illustrates a representation of an analyzed thermal image;

FIG. 39A illustrates a representation of another vectorized thermal image;

FIG. 39B illustrates a representation of another analyzed thermal image;

FIG. 45B illustrates a human Qi channel diagram template;

FIG. 45C illustrates a thermal image 1575 corresponding to the flow of Qi;

FIGS. 46A and 46B illustrate an embodiment of front and back anatomy reference images;

FIGS. 47B and 47C illustrate a front anatomy image and a back anatomy image;

FIGS. 48B and 48C illustrate a front anatomy image and a back anatomy image;

FIG. 49B illustrates a human arterial system image with microcirculation areas designated;

FIG. 49C illustrates a human venous system image with the microcirculation areas designated;

FIG. 50A illustrates a digestive system reference image;

FIG. 50B illustrates a nervous system reference image;

FIG. 50C illustrates a lymphatic system reference image;

FIG. 52B illustrates a front anatomy reference image for muscle evaluation;

FIG. 53 illustrates a front anatomy reference image for muscle damage evaluation;

DETAILED DESCRIPTION OF THE INVENTION

Embodiments described herein relate to methods and systems of structuring the infrared software, mapping, processing, analysis, data-sharing, and work-flow systems. Methods and structures of the system are not limited to the specific embodiments described herein. Any embodiment described herein as "exemplary" is not necessarily to be construed as preferred or advantageous over other embodiments.

In one embodiment, a system and method for health evaluation utilizing Thermal Micro Texture (TMT) mapping technology is disclosed (hereinafter referred to as "the TMT system" or "health evaluation system"). The TMT system detects and maps changes in the body's temperature by analyzing the infrared rays emitted by the body in order to discover and diagnose early signs of an illness or disease.

When an individual undergoes a health check-up to detect early signs of a disease, he or she undergoes screening such as CAT scans or MRIs. The TMT system differs from these types of X-ray detection devices on four respects described below.

The first difference is that CAT scans, ultrasound X-rays, and MRIs (traditional techniques) generally provide structural checks reflecting changes in human tissue organs. In contrast, the TMT system reflects changes in an individual's human metabolism and blood circulation, or the body's change in temperature. The metabolism of cancerous tissue is the most active in the early phases of cancer. This cancerous tissue thereby produces a large amount of local surface heat and subsequently causes a change in the body surface temperature. Because of this, the TMT system enables the physician to diagnose and evaluate the source/cause of the variation or disease. The TMT system thereby enables early discovery of cancer.

The second difference is that traditional techniques, identified earlier, generally provide structural checks that reflect changes in human tissue structure. The TMT system tracks changes in the function and thermal radiation of a specific area of the body. These changes occur generally before changes to the tissue or organ structure. This allows the TMT system to detect signs of a disease while it is in the early stage. Hence, the TMT system acts as a preventive, rather than a reactive, system.

The third difference is that the TMT system avoids potential damage caused by X-rays. As discussed earlier, traditional techniques are known to expose the body to harmful radiation. Exposure to harmful rays does not occur when utilizing the TMT system because it does not make use of such harmful radiation techniques. Instead, the technology in the TMT system is set up to receive (and pinpoint) any heat energy that is emitted from the body. The TMT system does not produce any harmful radiation, thereby avoiding the risk of exposing an individual to harmful radiation.

Finally, the TMT system provides a procedure which is convenient, quick, and cost-effective compared to other systems.

Figure 1:
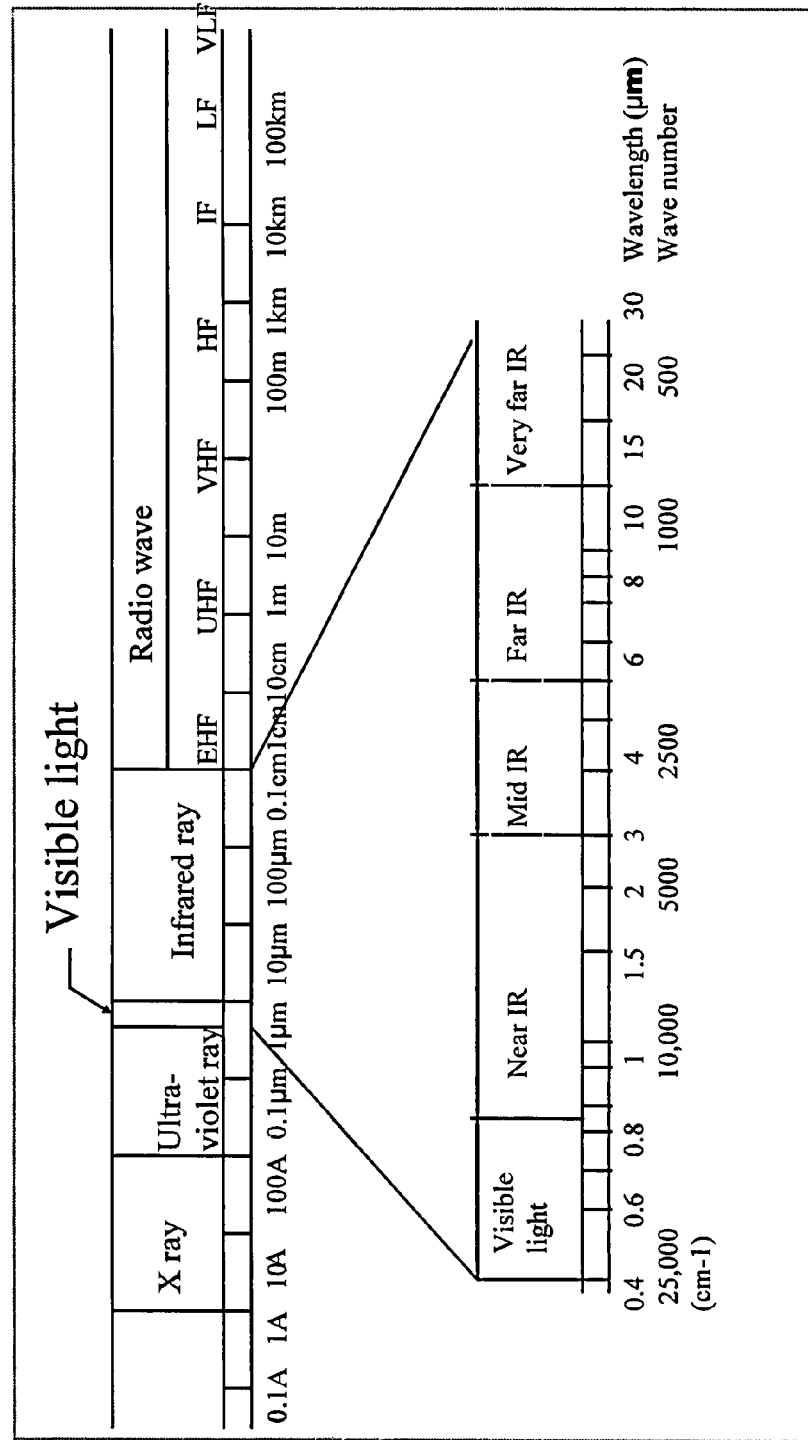
FIG. 1 illustrates a conventional electromagnetic spectrum distribution.

FIG. 1 illustrates a conventional electromagnetic spectrum distribution. The infrared ray portion of the electromagnetic spectrum distribution is expanded and shown following a visible light range. The visible light range includes violet, blue, green, yellow, orange, and red colors. The visible light range is followed by the infrared ray range, which includes a near infrared range, a mid infrared range, a far infrared range, and a very far infrared range. The infrared ray is a kind of ray invisible to the human eye, in the spectrum beyond the visible red light. The infrared ray range is comprised of electromagnetic radiation in the wavelength interval 0.76 µm~1000 µm, connected to visible light at the lower end and millimeter wave at the higher end. The visible light range is 0.4 µm~0.76 µm and is considerably narrower than the wide infrared ray range (0.76 µm~1000µ).

Infrared (IR) rays are also known as heat rays or thermal radiation. Although different in form, the infrared ray, the visible light, and the radio wave are the same in essence, all being part of electromagnetic radiation, only differing in frequency (wavelength). Infrared rays have the same properties as other light waves: linear propagation in a vacuum and follow the laws of reflection, refraction, diffraction and polarization.

There are three laws which describe the radiation. The three laws include the Planck Law, the Stephan-Boltzmann Law, and the Wien Displacement Law. The Planck Law, in general, describes the spectral distribution of blackbody radiation. The Stephan-Boltzmann Law describes the total power radiated from an object in a unit area. According to the Stephan-Boltzmann Law, the higher the absolute temperature, the greater the radiant existence. According to the Wien Displacement Law, the wavelength of infrared radiation of an object relates to its temperature. Thus, the higher the absolute temperature, the shorter the radiation wavelength, and vice versa.

The TMT system provides functional checks reflecting changes in human metabolism and blood circulation. Such changes are expressed through human thermal micro-sectional view technology. X-ray, CAT Scans, Ultrasonic B, and nuclear magnetic resonance technologies provide structural checks reflecting changes in human tissue structure. The two kinds of checks are complementary to, but not replaceable by, each other.

Figure 2:
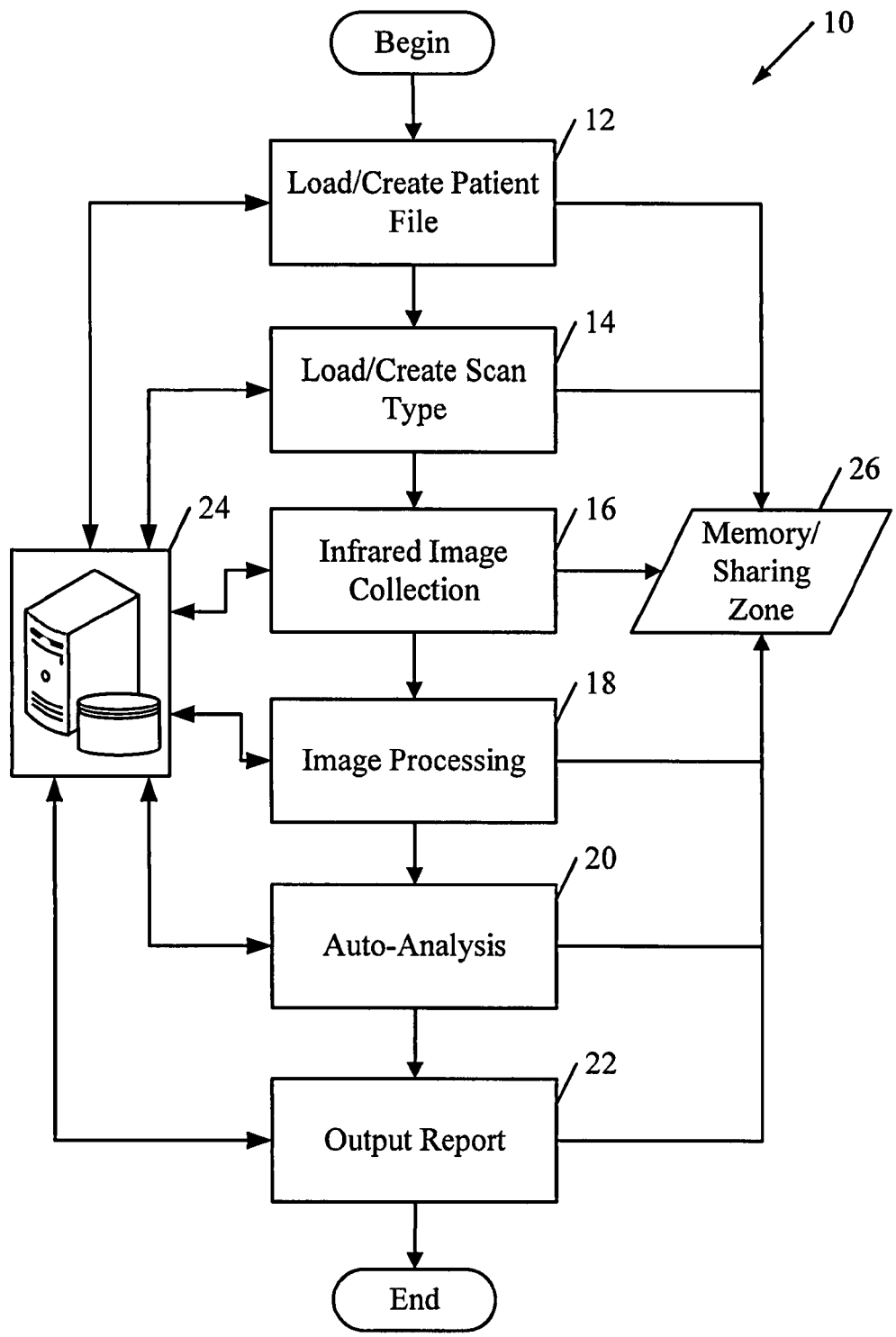
FIG. 2 illustrates a flow diagram of one embodiment of a Thermal Micro Texture (TMT) mapping technology health evaluation process.

FIG. 2 illustrates a flow diagram of one embodiment of a TMT mapping technology health evaluation process 10. Health evaluation process 10 allows a user to create or load a patient file at block 12 or retrieve patient file at block 12 from a database or a computer readable medium denoted by block 24. Once the patient file is created or loaded at block 12, the desired scan type is selected (created or loaded) at block 14 for capturing an infrared image capture at block 16.

The scan type is made up of sets of predefined infrared positional images (shown in FIGS. 21A-21R) of the human anatomy, which are specific to the type of evaluation scan to be performed. In one embodiment, the scan type can be retrieved from the database or computer readable medium denoted by block 24 or loaded from memory/sharing zone denoted by block 26. Following the loading of the scan type, infrared images are captured or collected at block 16 in order to provide health evaluation system 40 (shown in FIG. 3) with infrared data to process and evaluate. Once the infrared images are captured at block 16, image processing is performed at block 18. The image processing at block 18 is accomplished through several software modules, further described below in FIG. 4, which enable the user to enhance the raw infrared data for manual and automated use. Block 18 is followed by block 20 where auto-analysis takes place. The auto-analysis operation at block 20 receives the refined data from block 18, after image processing has been completed. The auto-analysis includes the processing of the data against a rule-set corresponding to the selected scan type to determine the health of the patient in regards to the selected scan type. After the auto-analysis at block 20, an output report is generated at block 22 with results of the auto-analysis on the infrared scan. The data for the patient file, scan type, infrared image capture, image processing, auto-analysis, and report output may be loaded and stored utilizing the database or computer readable medium denoted by block 24 and the memory/sharing zone denoted by block 26.

In an alternate embodiment, health evaluation process 10 may omit certain blocks or steps illustrated in FIG. 2. For example, block 16 to capture or collect the infrared image may be omitted if pre-captured infrared images are used or a scan type which does not require the capture of new positional infrared images is used. Block 20 for performing auto-analysis may also be omitted if health irregularities are determined manually.

Figure 3:
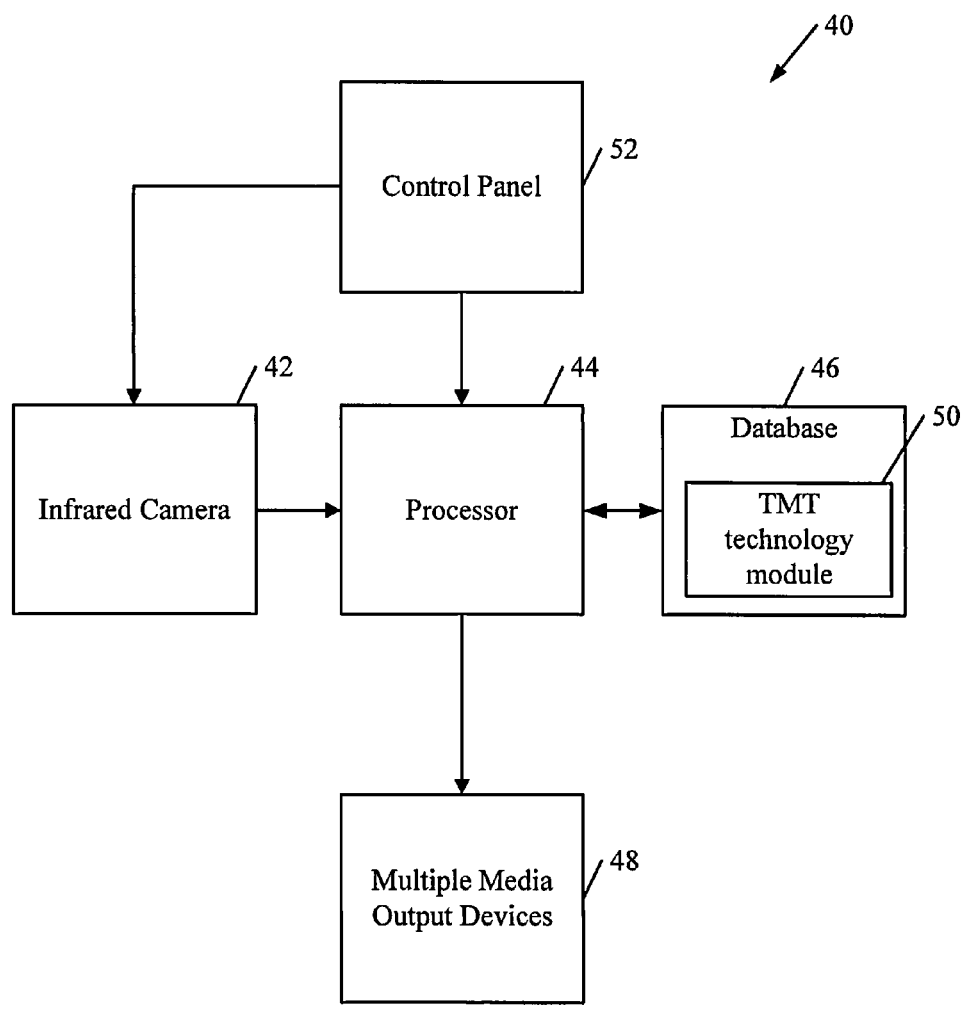
FIG. 3 illustrates a general block diagram of system components of a health evaluation system.

FIG. 3 illustrates a general block diagram of system components of a health evaluation system 40. Health evaluation system 40 includes, in general, a control panel 52 to operate and manage an infrared camera 42. Control panel 52 transmits instructions to a processor 44, as necessary. Infrared camera 42 captures an infrared image and communicates the infrared image to processor 44. The captured infrared image is initial raw data. Processor 44 communicates the initial raw data to a database or computer storage medium 46 for storage therein and subsequent retrieval.

Control panel 52 is configured to send a command to instruct processor 44 to process the initial raw data according to methods described in FIGS. 7-10, and to store the processed data in a database or computer storage medium 46. In addition, control panel 52 is also capable of sending a command to instruct processor 44 to auto-analyze the processed image data according to rule-sets, as described in more detail below, retrieved from database or computer readable medium 46. Image data and results are also available to be displayed on a client system (not shown) or output to multiple media output devices 48 including, but not limited to, display monitors, computers, web pages, email, fax machines, and printers.

Database or computer readable medium 46 includes a TMT technology module 50 for carrying out health evaluation process 10. Module 50 includes instructions and rule-sets for performing health evaluation process 10. Module 50 includes at least the rule-set for auto-analyzing the processed image data, as well as the TMT graphical user interfaces (FIGS. 22-39) for allowing the user to interact with health evaluation system 40 for carrying out health evaluation process 10.

In one embodiment, database or computer readable medium 46 stores all of the system information including raw infrared image data, processed infrared image data, auto-analysis results, and reports. In another embodiment, however, database or computer readable medium 46 may also be split into multiple databases, each database storing its own set of specific data. In yet another embodiment, a computer may act as multiple components as shown in FIG. 3.

Figure 3A:
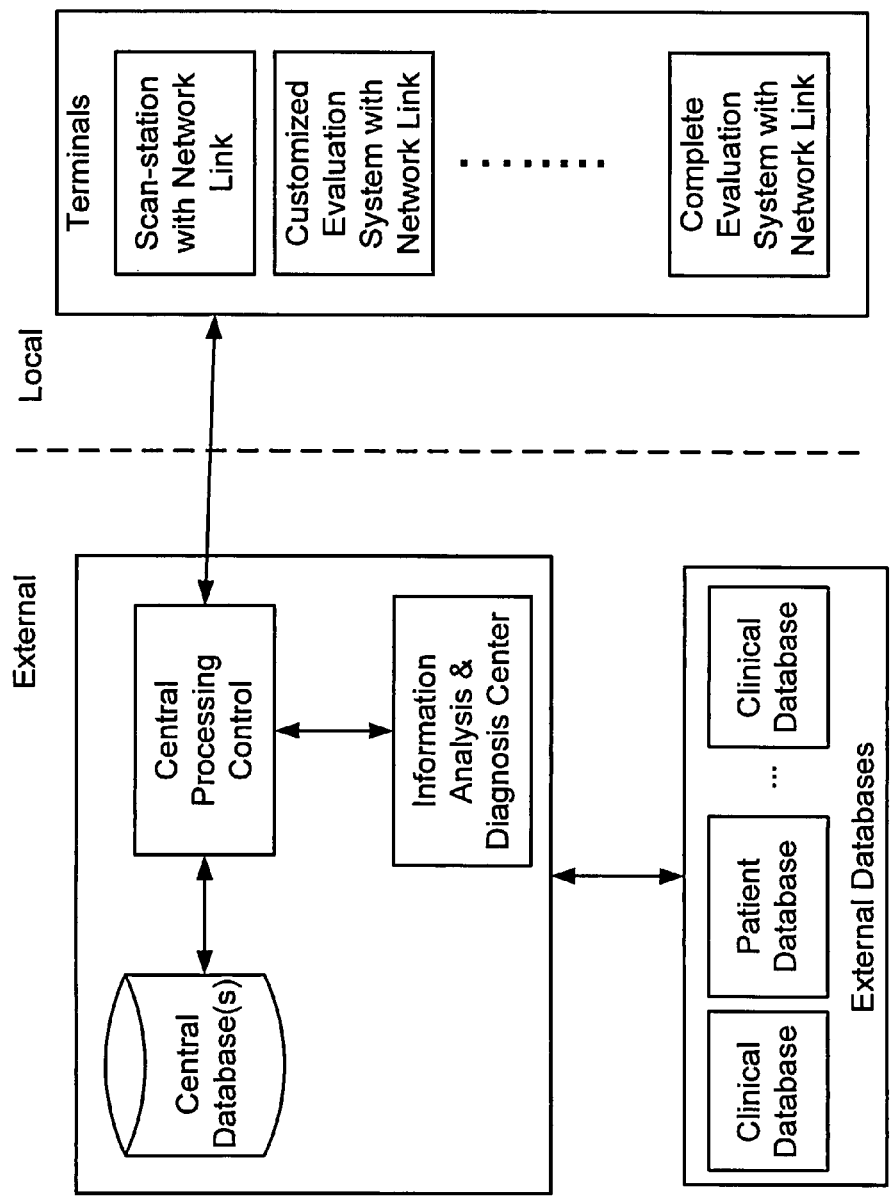
FIG. 3A illustrates a network diagram depicting a multi-modal data sharing system.

FIG. 3A illustrates a network diagram depicting a multimodal data sharing system. In one embodiment, multiple systems 40 all over the world are linked to a central database. The central database contains patient information and analysis from external linked systems 40 all over the world. When a local network linked system 40 gathers and analyzes data from a patient, the data is sent to the central database. At the central database, central processing control sends information to the information analysis and diagnosis center. The information analysis and diagnosis center compares the patient information gathered from local system 40 against information in the central database of patients with similar TMT mappings. Based on comparison with the previously diagnosed patients, the information analysis and diagnosis center determines the illness of the patient scanned at local system 40.

Figure 4:
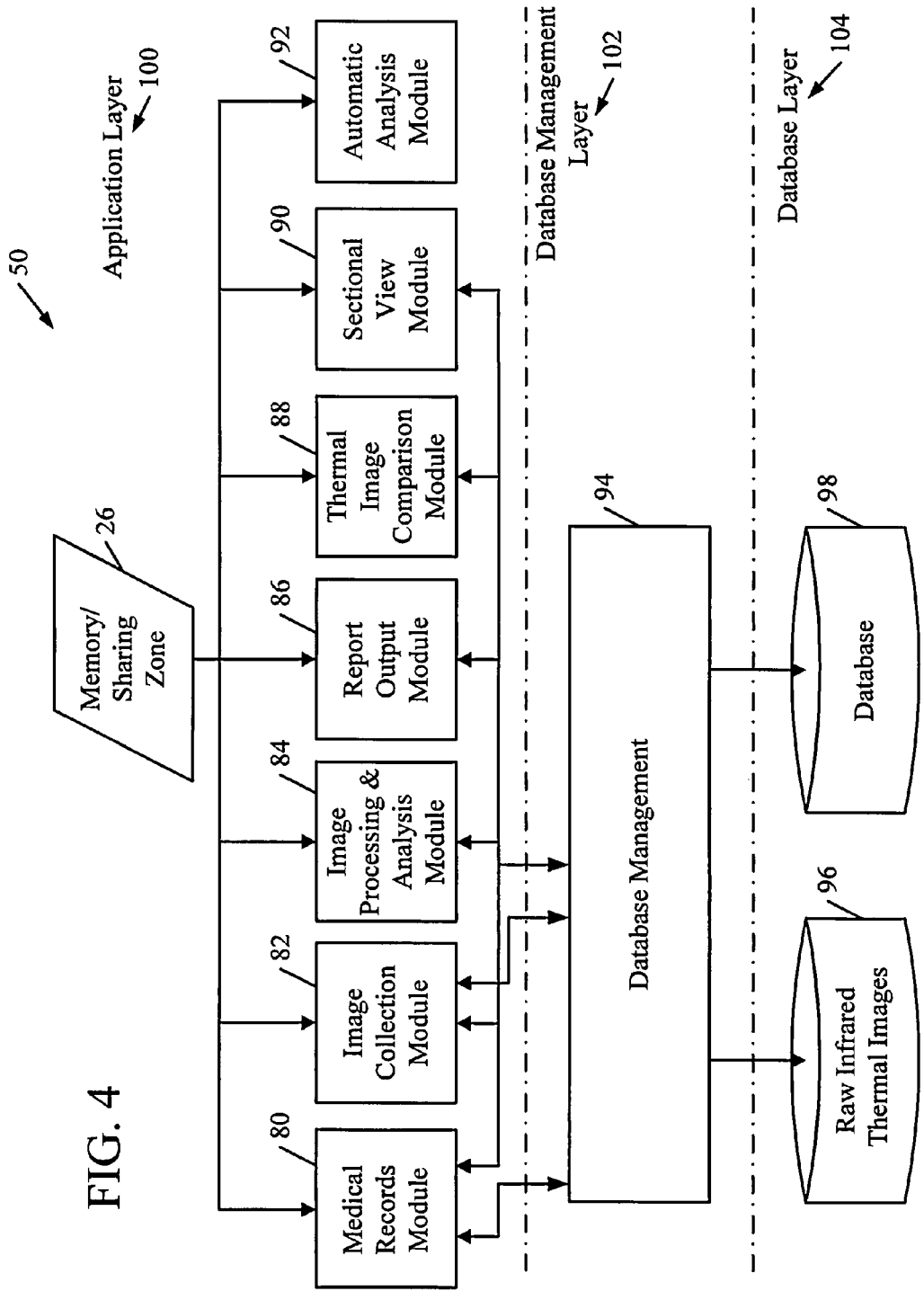
FIG. 4 illustrates a general block diagram of a TMT technology module of the health evaluation system.

FIG. 4 illustrates a general block diagram of module 50 of health evaluation system 40 (shown in FIG. 3). Module 50 has generally three layers: an application layer 100, a database management layer 102, and a database layer 104. Application layer 100 is made up of a common memory or sharing zone 26 for which data between modules is shared and accessed. Application layer 100 includes a medical records module (MRM) 80, an image collection module (ICM) 82, an image processing and analysis module (IPAM) 84, a report output module (ROM) 86, a thermal image comparison module (TICM) 88, a sectional view module 90, and an automatic analysis module (AAM) 92. These modules are further described and depicted in FIGS. 5-13. As illustrated in FIG. 2 and FIG. 3, data for each module may be stored in a database or a computer readable medium 98. A database management component 94 identifies the module request to store or retrieve information and routes the request to database 98 if the module request is valid. Through database management component 94, the modules exchange information, data disk files etc. among each other. At database layer 102, the generation, retrieval, and addition of medical records take place. Database layer 104 stores such information as the basic medical information, additional medical information, image file index information, and temperature measurements of patients.

MRM 80 includes, for each patient, basic and clinical information which is saved and managed in database 98. The medical history, present condition of the patient, etc. can be readily accessed and retrieved from database 98.

ICM 82 includes, for each patient, infrared information obtained through scanning or image capturing. The infrared information is also saved and stored in database 98. ICM 82 converts the infrared information into color images and displays them onto a suitable user interface such as a display monitor.

IPAM 84 allows a user to manipulate a patient's three-dimensional images so as to most effectively depict the thermal distribution. The user can also make a comprehensive analysis of the thermal images using different functions. Completed analysis is saved in the database and may be retrieved at a later date for future comparison.

ROM 86 allows the user to print out the records of a patient, including all clinical information, thermal images, and corresponding analysis utilizing the various features of ROM 86.

TICM 88 allows the user to compare the same bodily areas of different patients and their corresponding body area temperatures. Because database 98 is capable of saving and storing a large number of patients' thermal images, the user can utilize different options to compare the same bodily areas of different patients for various data sets of information.

Module 90 is also referred to as the cascade chromatography module (CCM). CCM allows dynamic temperature changes of a patient's thermal image to be converted into a static form through cascade chromatography of the thermal image, as described later in relation to FIGS. 40A, 40B, and 40C.

Health evaluation system 40 (shown in FIG. 3) is capable of automatically analyzing the infrared images using artificial intelligence with reference to the results generated by various modules including, but not limited to, modules 82, 84, 86, 88, and 90. The system is capable of storing the sectional views of the patients' data and medical analysis rules, and also storing final analysis results.

As can be appreciated, to describe each and every request, storage, and retrieval operation is prohibitive. Thus, one example is described below. In one embodiment, ICM 82 sends a request to store new infrared images captured for a patient. Database management component 94 stores the new infrared images in a raw infrared thermal images database 96. Other information pertaining to other modules, such as ROM 86, may store and retrieve its information from another database 98.

Figure 5:
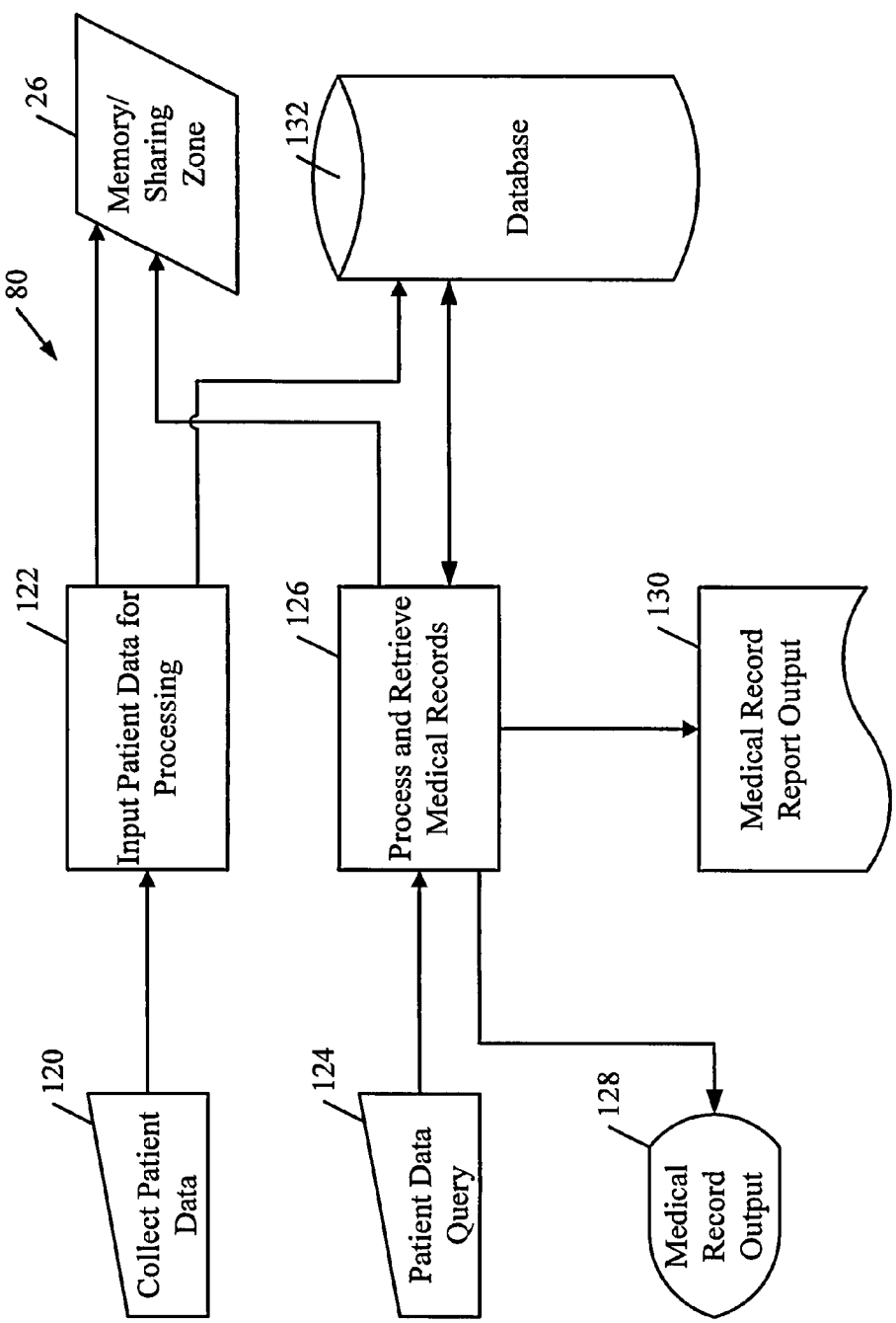
FIG. 5 illustrates a flow diagram depicting a medical record module.

FIG. 5 illustrates a flow diagram depicting MRM 80. MRM 80 can create a new patient record by collecting patient data at block 120 (via hand-written forms or questionnaires, etc.) including information such as the patient's name, date of birth, case history, family history, and symptoms. Graphical user interfaces (GUI) as shown in FIGS. 22-29 allow a user to enter the patient's information into data entry fields of the GUI. Block 120 is followed by block 122 where the collected patient data is input or entered for processing. During the operations of block 122, the electronic processing of patient data assigns the patient a medical record index for storage and retrieval using a database 132.

Block 124 provides for a patient data query. If the patient already has a medical record, then a patient data query can be generated at block 124. Block 124 is followed by block 126 where the query is processed and medical records (previously stored) are retrieved from the database 132. Patient data queries of block 124 are not limited to retrieval of records for a single patient. Thus, patient data queries can include population studies of a pool of patients for clinical studies use. Once the desired medical record(s) are retrieved from block 126, the medical record(s) can be output as raw data via a direct medical record(s) output at block 128, or as a formatted medical record report output at block 130. The medical record output generated at block 128 and medical record report generated at block 130 can be output to multiple media formats, including electronic and hard-copy forms. Information collected from the electronic processing of patient data at block 122 and retrieval of medical records at block 126 is also sent to memory or sharing zone 26 for access by other modules.

Figure 6:
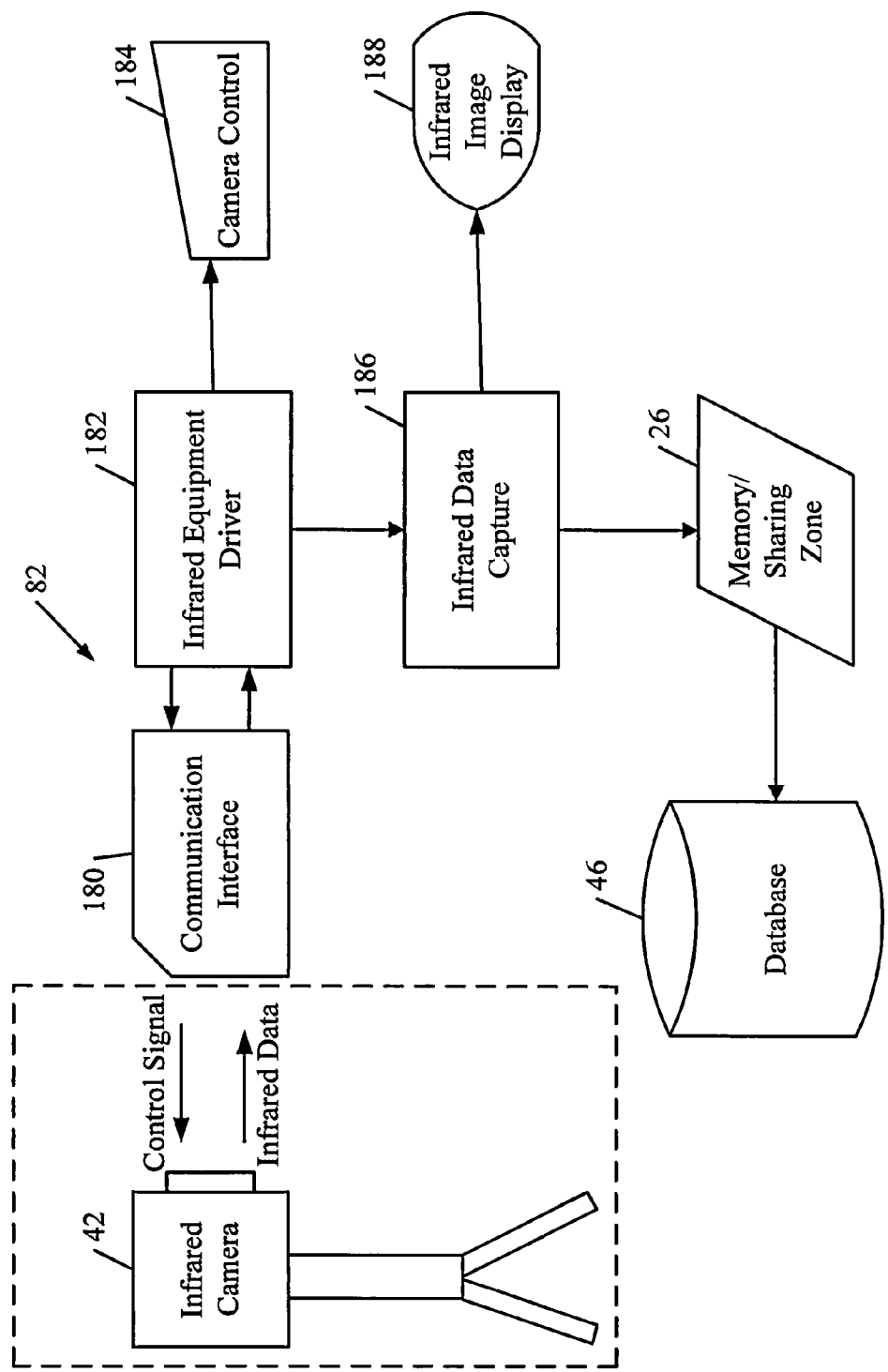
FIG. 6 illustrates a flow diagram depicting an image collection module.

FIG. 6 illustrates a flow diagram depicting ICM 82. An infrared camera 42 is controlled through a communications interface 180, which sends control signals and receives infrared data. Infrared camera 42 is demarcated in a dashed-line box to denote separation from ICM 82. ICM 82 includes a communications interface denoted at block 180, which is driven by a camera control denoted at block 184 through an infrared equipment driver denoted at block 182.

In one embodiment, a computer may act as the camera control at block 184, using a software version of infrared equipment driver 182 to control infrared camera 42 through communications interface at block 180. By way of example, communications interface at block 180 may be a universal serial bus connection. When infrared equipment driver at block 182 is given a command to perform an infrared data capture operation at block 186, an infrared image display at block 188 is generated and output to a display device such as a monitor. Infrared data capture at block 186 is also sent to memory or sharing zone 26 for access by other modules. Infrared data captured at block 186 is also stored in database 46. In one embodiment, database 46 can be its own dedicated database to store infrared images, whereas in another embodiment, database 46 may be utilized to store all relevant information relating to health evaluation system 40 (shown in FIG. 3).

Figure 7:
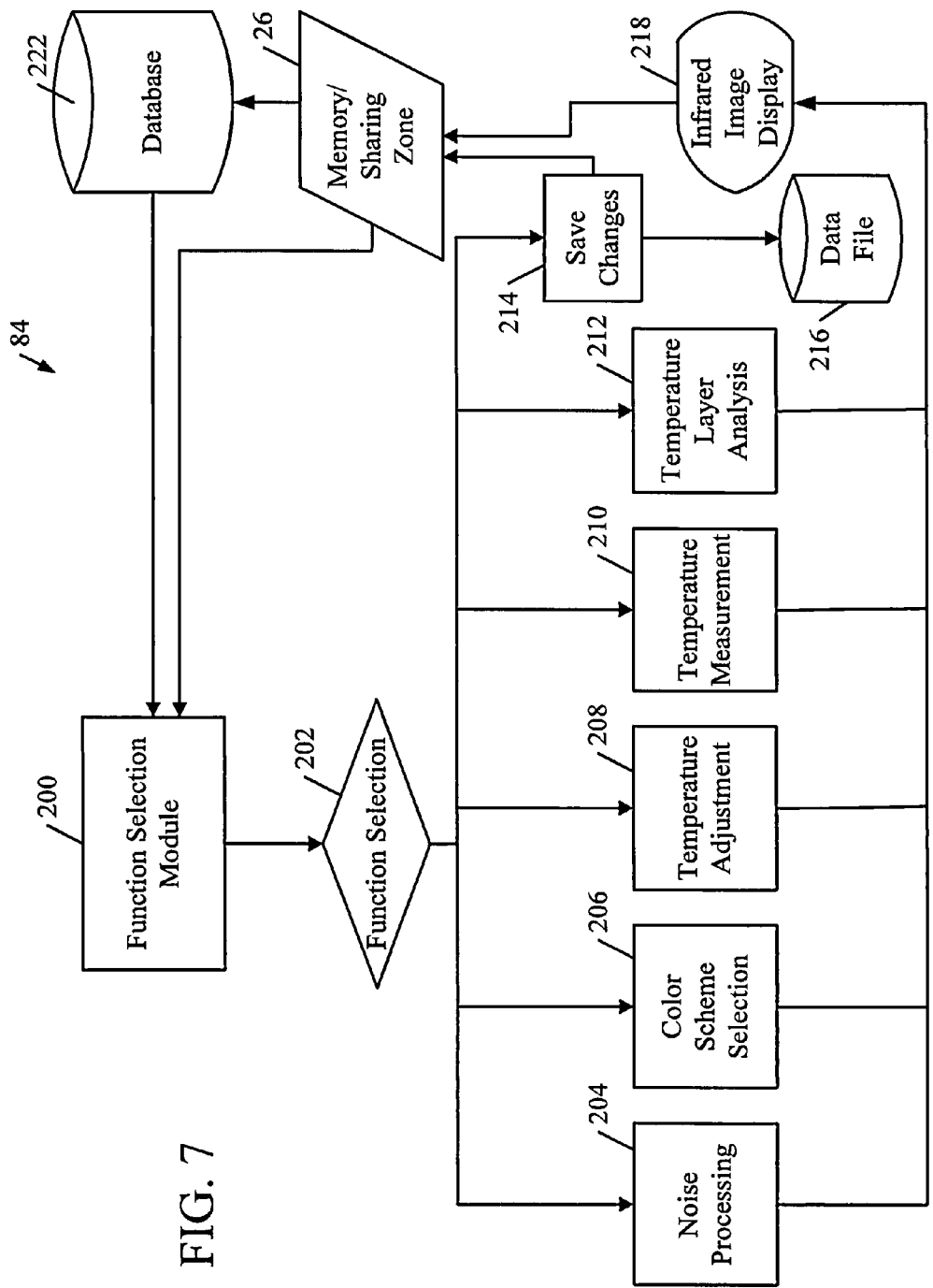
FIG. 7 illustrates a flow diagram depicting an image processing and analysis module.

FIG. 7 illustrates a flow diagram depicting IPAM 84. IPAM 84 is one of the modules which make up image processing operation of block 18 (shown in FIG. 2). IPAM 84 begins with block 200 where a function selection module is linked to a database 222 and memory or sharing zone 26. IPAM 84 retrieves infrared images and other related information from database 222 for processsing. Block 202 performs a function selection to determine how the infrared image data is manipulated. The available options for the function selection are a noise processing function at block 204, a color scheme selection function at block 206, a temperature adjustment function at block 208, a temperature measurement function at block 210, a temperature layer analysis function at block 212, and an option to save changes function at block 214.

The noise processing function at block 204 is an automated process which filters out irrelevant background infrared data that may be present in the captured infrared image. The color scheme selection function at block 206 allows for the selection or specification of color palettes which are used to display infrared images. The temperature adjustment function at block 208 allows for the specification of an upper and lower range of temperature values that is displayed by colors from the color scheme selection function at block 206. The temperature measurement function at block 210 allows temperature measurement of points, rectangles, ellipses, and polygons of parts of an infrared image. The temperature measurement function at block 210 provides values which can also be saved. The temperature layer analysis function at block 212 allows the system to determine the depth of global or local temperature areas of a patient's body.

Aside from saving changes at block 214, when one of the other functions is selected, an infrared image display at block 218 is updated to reflect the processed image. Each of the blocks 204, 206, 208, 210, and 212 proceed to block 218. Block 218 is followed by memory or sharing zone 26. Such changes to the infrared image are then sent to memory or sharing zone 26 to be used by other modules or downloaded to database 222. IPAM 84 can also save changes via the save changes function at block 214 to a data file 216 in a standard format (e.g. BMP, JPG, etc.).

Figure 8:
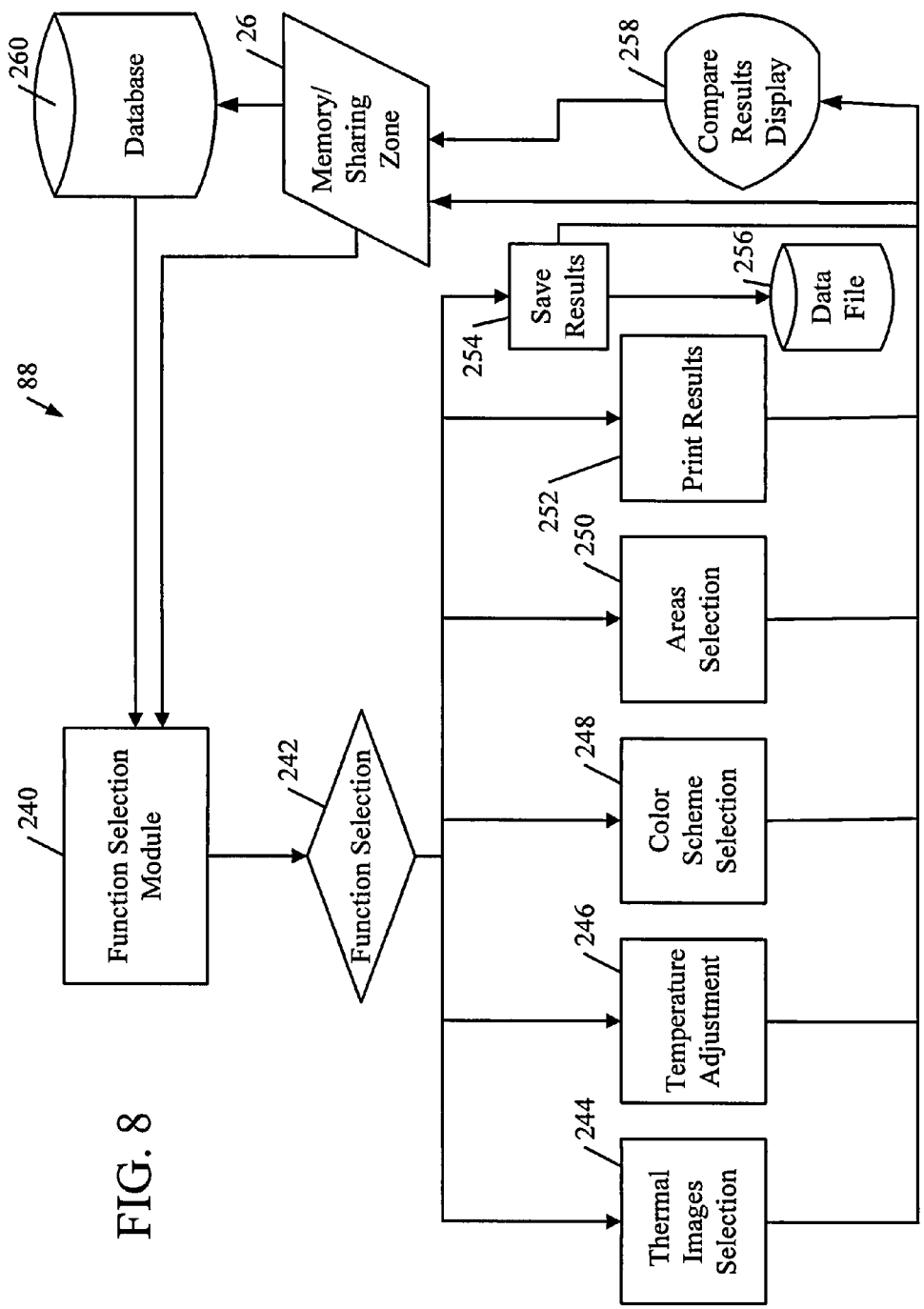
FIG. 8 illustrates a flow diagram depicting a thermal image comparison module.

FIG. 8 illustrates a flow diagram depicting TICM 88. TICM 88 is one of the modules which makes up the image processing at block 18 (shown in FIG. 2). TICM 88 begins with block 240 where a function selection module is linked to a database 260 and memory or sharing zone 26 to provide it with thermal images to compare. Block 240 is followed by block 242 where a function selection takes place to determine how the infrared image data is manipulated and compared. The available options are a thermal image selection function at block 244, a temperature adjustment function at block 246, a color scheme selection function at block 248, an area selection function at block 250, a print results function at block 252, a save results function at block 254 coupled to a data file 256 and database 260.

The thermal image selection function at block 244 allows multiple thermal images to be selected for comparison. These thermal images can be from the same or different patients, from the same or different time periods, or from the same or different image capture positions. The color scheme selection function at block 248 allows for the selection or specification of color palettes with which to represent infrared images. The temperature adjustment function at block 246 allows for the specification of an upper and lower range of temperature values that can be displayed by colors from the color scheme selection function at block 248. The area selection function at block 250 allows for a selection of points or areas of thermal images to be compared by temperature, and have such comparisons recorded for analysis. The print results function at block 252 creates a visual report showing the areas compared and the results of the comparison. The save results function at block 254 saves the temperature comparison results into database 260 or data file 256. Except for the print results function at block 252 and save results function at block 254, when one of the other functions is selected, a comparison results display at block 258 is updated to reflect the comparison results. Such changes to the infrared image are then sent to memory or sharing zone 26 to be used by other modules or written to a database 260. Thus, blocks 244, 246, 248, 250, and 254 are followed by block 258. Block 258 is followed by memory or sharing zone 26.

Figure 9:
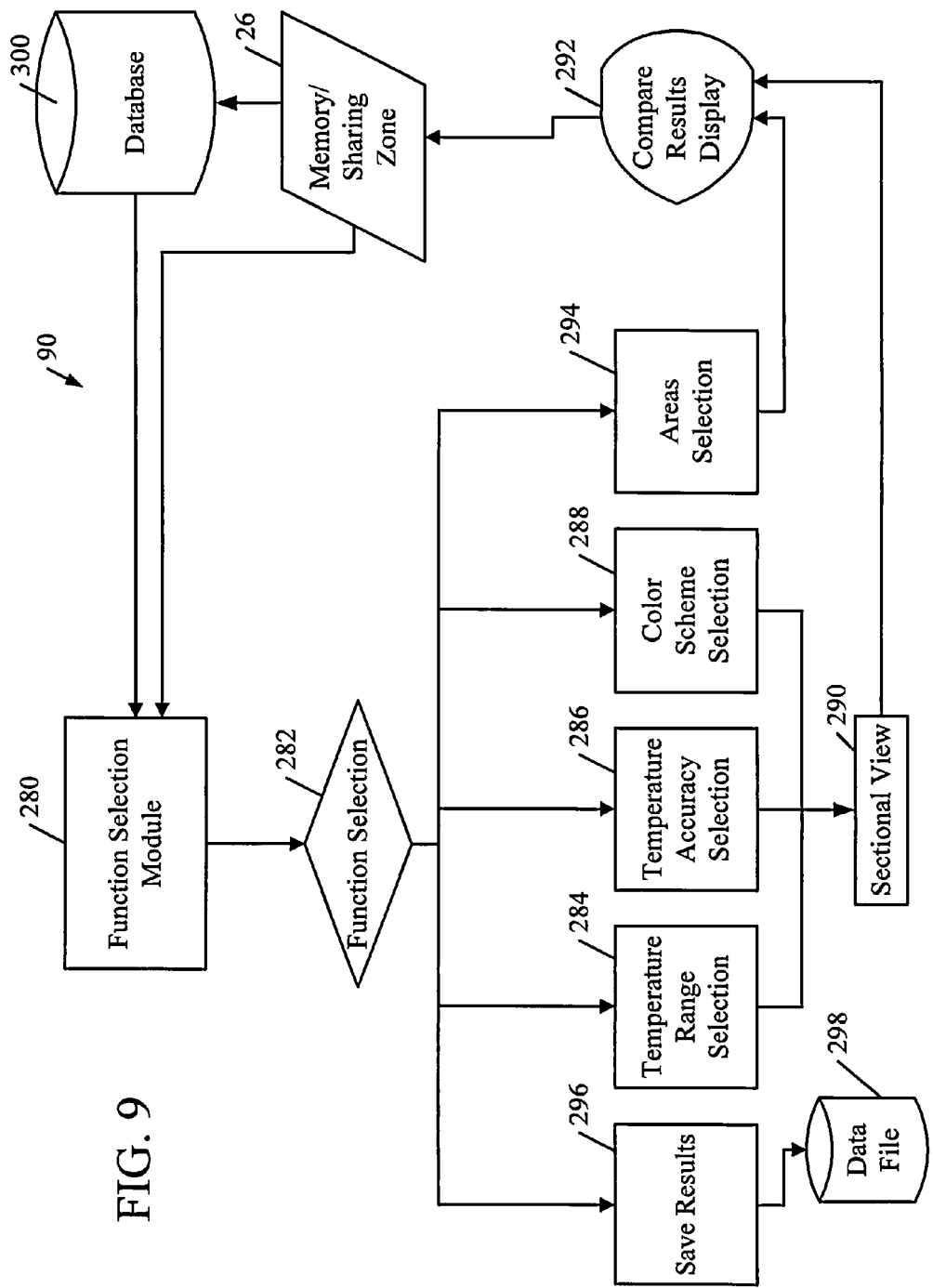
FIG. 9 illustrates a flowchart depicting a sectional view module.

FIG. 9 illustrates a flow diagram depicting module 90. Module 90 is one of the modules which makes up the image processing at block 18 in FIG. 2. Module 90 begins with block 280. A function selection module at block 280 is linked to a database 300 and memory or sharing zone 26 to provide it with thermal images to compare. Block 280 is followed by a function selection at block 282 to determine how the infrared image data is manipulated and displayed. In one embodiment, block 282 allows the user to select one or more of the five different options. The available options are a temperature range selection function at block 284, a temperature accuracy selection function at block 286, a color scheme selection function at block 288, an area selection function at block 294, and a save results function at block 296.

The color scheme selection function at block 288 allows for the selection or specification of color palettes with which to represent infrared images. The temperature range selection function at block 284 allows for the specification of an upper and lower range of temperature values to be displayed by colors selected from the color scheme selection function at block 288. The temperature accuracy selection function at block 286 specifies the temperature precision between layers of thermal sectional views. The area selection function at block 294 allows an area to be highlighted for focus (in color) while the rest of the image is displayed as gray. Use of the option of the area selection function at block 294 forces an update to a section view display at block 292. The section view display at block 292 can be output to a variety of devices or shown within an application interface. A sectional view option at block 290 generates sectional views utilizing specified or default values of temperature range, temperature accuracy, and color scheme values. The generation of these sectional images is described in further detail in FIG. 10. The section view display at block 292 shows the generated sectional views and transfers this data to memory or sharing zone 26 before being stored in a database 300. The save results function at block 296 saves all or parts of the sectional view thermal images as common graphic formats (e.g. JPEG, BMP, etc.) in a data file 298. The blocks 284, 286, and 288 are followed by the sectional view option at block 290. Block 290 is followed by block 292. The results display at block 292 is followed by memory or sharing zone 26.

Figure 10:
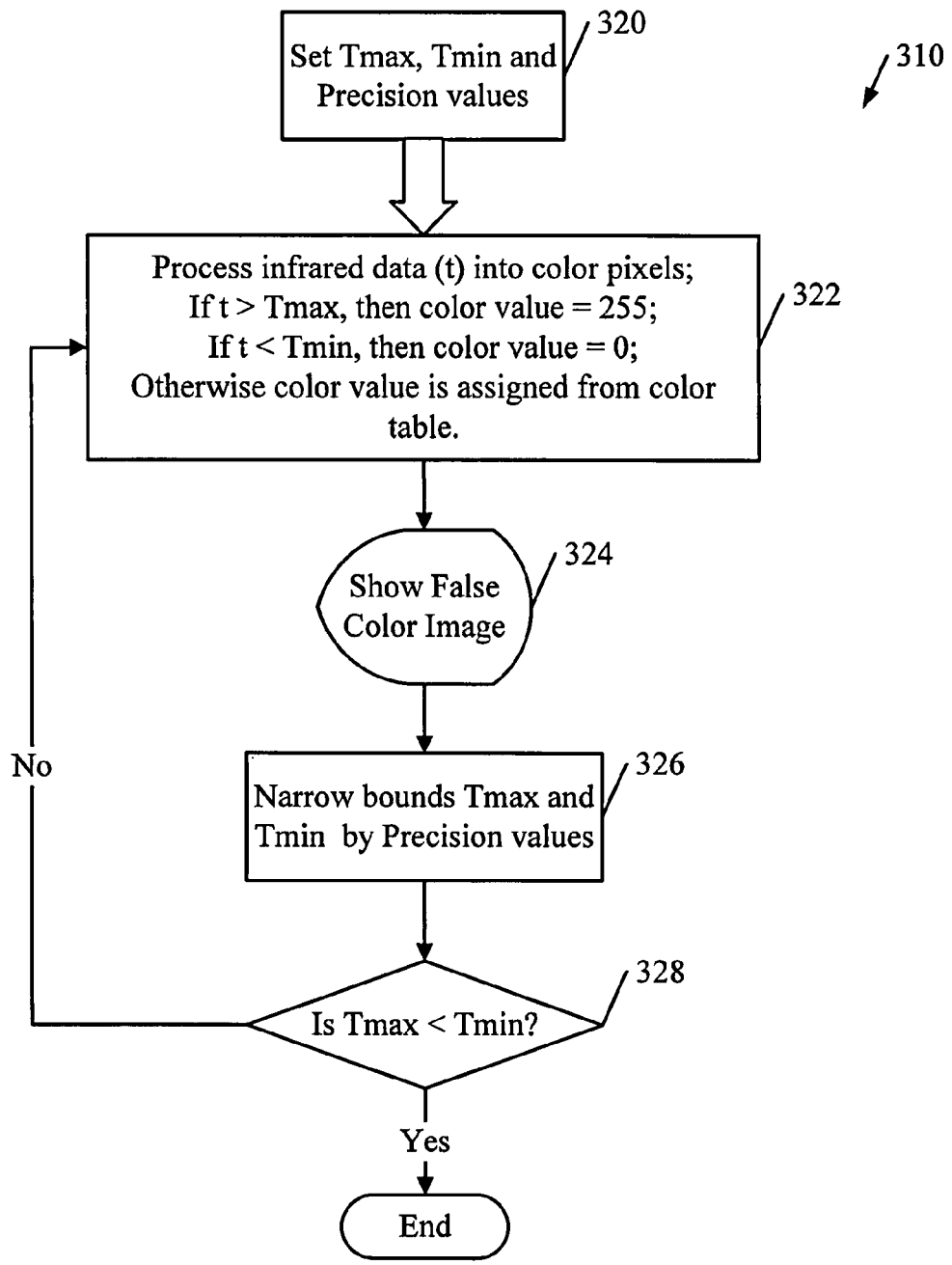
FIG. 10 illustrates a flowchart depicting a sectional view option process of FIG. 9.

FIG. 10 illustrates a flowchart depicting a sectional view option process 310 (shown in block 290 of FIG. 9). In the initial step of generating a sectional view, the maximum temperature (Tmax), minimum temperature (Tmin), and precision values (PV) are set at block 320. In block 322, the infrared data (t) is converted into color pixels according to the specified color scheme from FIG. 9. Any t values which exceed the Tmax value are assigned a color value equal to black. Any t values which fall under the Tmin value are assigned a color value equal to white. Otherwise, the t value is assigned a color corresponding to its temperature. This process generates a false color image which is then displayed in block 324. To create the next sectional view, the bounds Tmax and Tmin are narrowed by the specified precision value in block 326. Block 328 checks if Tmax is less than Tmin. If Tmax has been reduced to a value less than Tmin, sectional view option process 310 ends since there is no more precision to extract from the infrared image. Otherwise, process 310 loops back to block 322 with a new set of Tmax and Tmin values to generate a new sectional view.

Figure 11A:
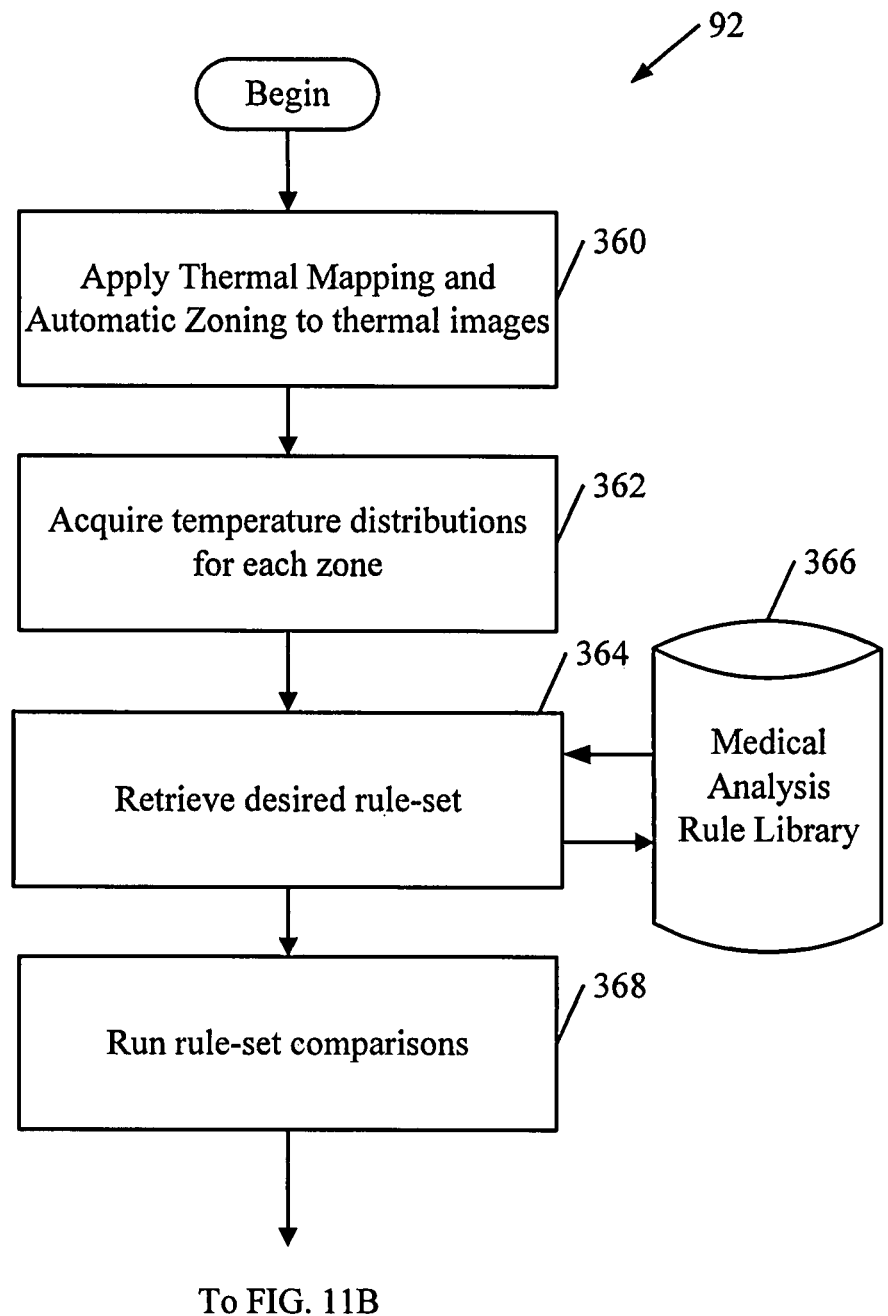
FIGS. 11A and 11B illustrate a flowchart describing an automatic analysis module.
Figure 11B:
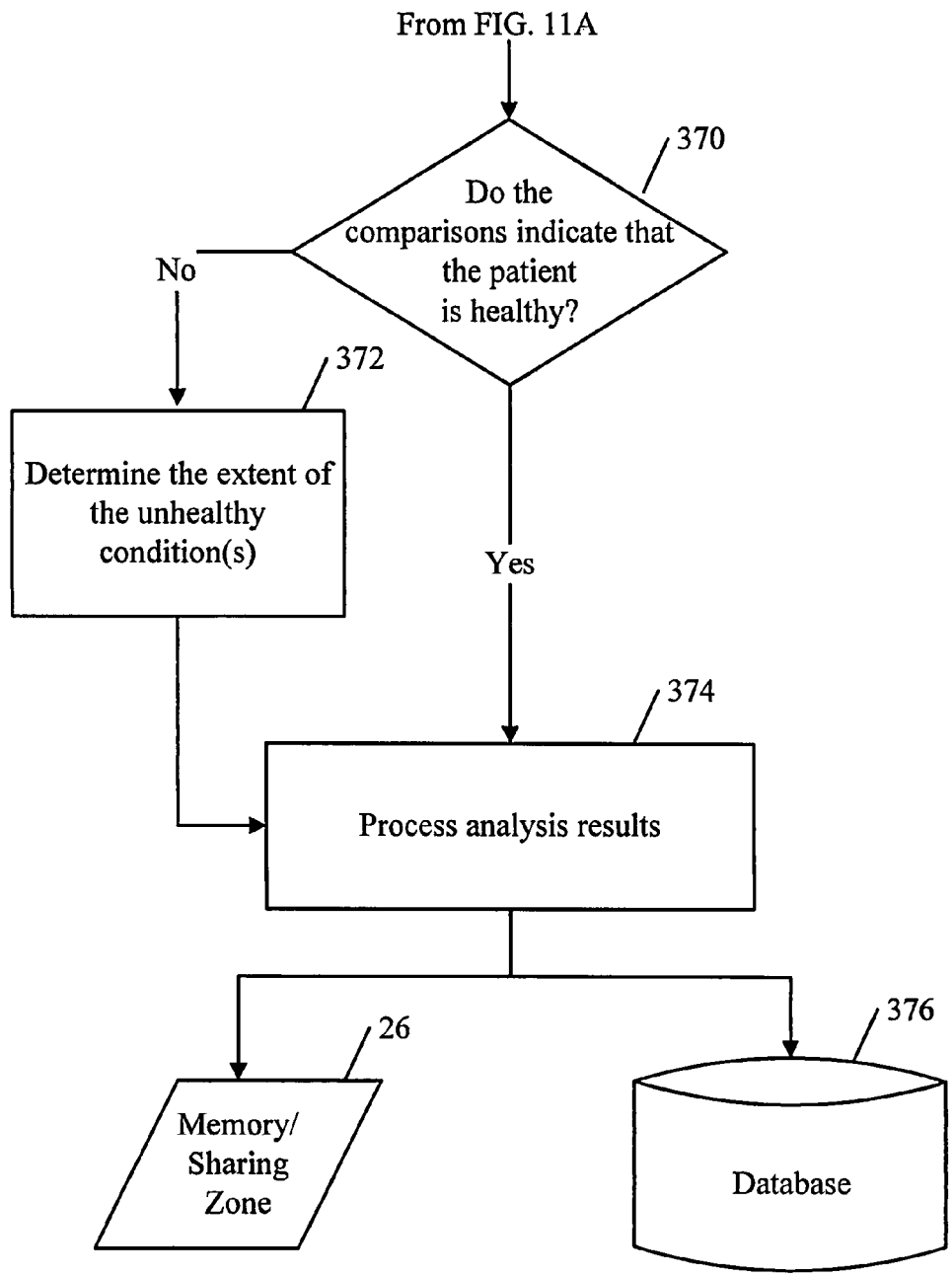

FIGS. 11A and 11B illustrate a flowchart describing automatic analysis module 92 (shown in FIG. 4). Automatic analysis module 92 utilizes a thermal mapping technique which allows the system to determine the overall health of a patient by examining relevant parts of a thermal scan. Automatic analysis module 92 begins at block 360 where thermal mapping and automatic zoning is applied to a patient's thermal images. The thermal mapping and automatic zoning is described in further detail in FIG. 12. After the zoning of infrared images is complete at block 360, the temperature distribution is calculated for each zone at block 362. Block 362 is followed by block 364, where health evaluation system 40 (shown in FIG. 3) retrieves a desired rule-set 364 from a medical analysis rule library database 366, and runs rule-set comparisons at block 368. Such rule-set comparisons may involve rules that determine the health of a patient given a variety of factors including, but not limited to, how a patient's thermal zones relate to a particular temperature range, distribution, or symmetry.

Referring now to FIG. 11B, block 368 (shown in FIG. 11A) is followed by block 370. At block 370, a determination is made whether the patient is healthy. If the determination is "No" at block 370 (i.e., the patient is not healthy), health evaluation system 40 (shown in FIG. 3) attempts to determine the extent of the unhealthy condition(s) at block 372. Block 372 is followed by block 374. If the determination at block 370 is "Yes" (i.e., that the patient is healthy), then block 370 is followed by block 374 where (healthy or unhealthy) analysis results are processed. Block 374 forwards the analysis results to memory or sharing zone 26 for access by other modules or to a database 376.

Figure 12:
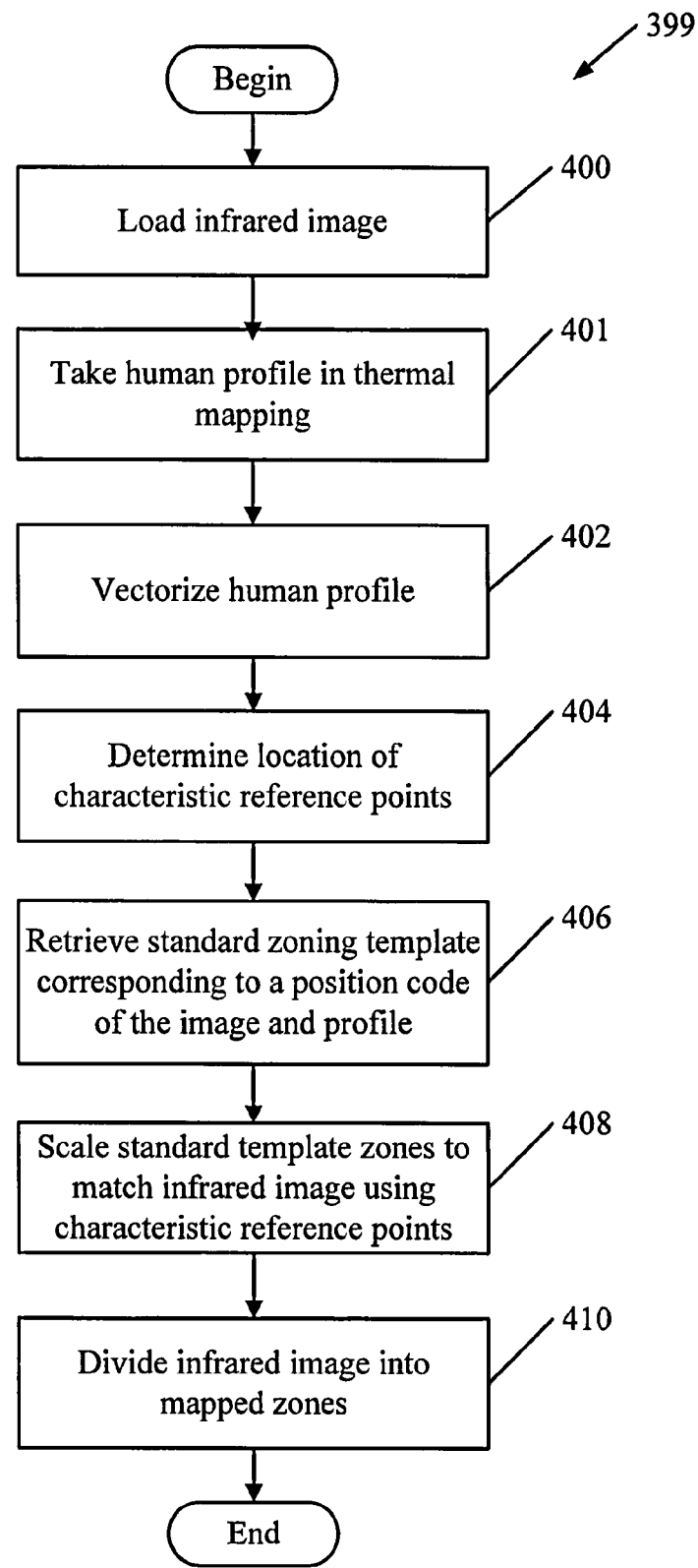
FIG. 12 illustrates a flowchart describing a process of a thermal mapping and automatic zoning.
Figure 14:
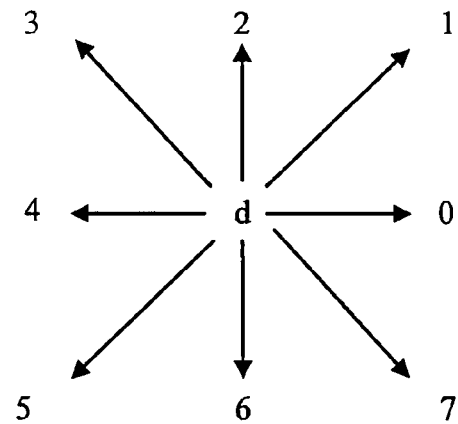
FIG. 14 illustrates a point d in an image and direction codes of its eight neighbors.
Figure 15A:
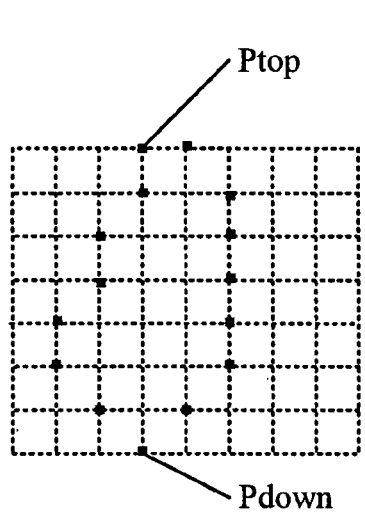
FIG. 15A illustrates points of a profile image.
Figure 15B:
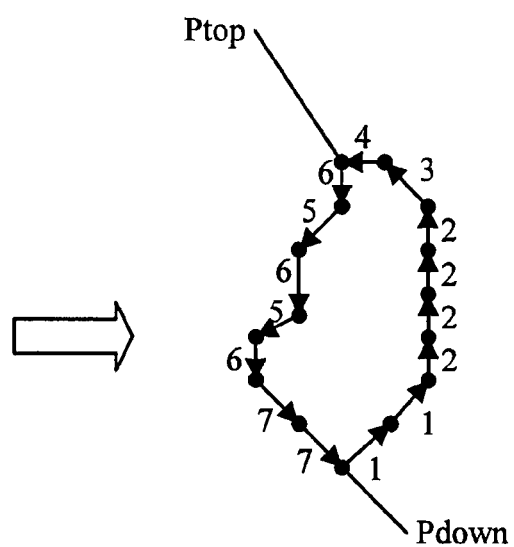
FIG. 15B illustrates a vectorization of the profile image.
Figure 16A:
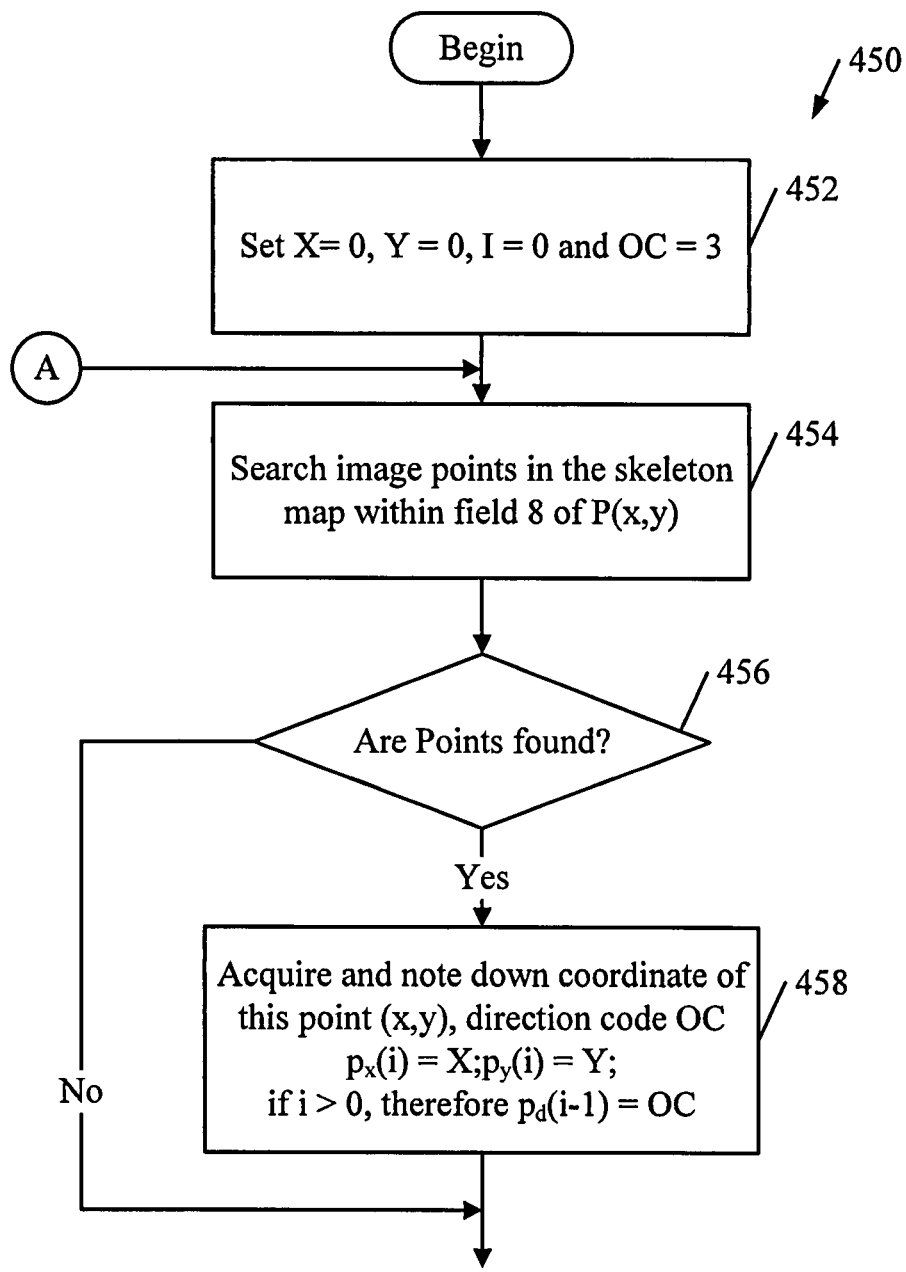
FIGS. 16A and 16B illustrate a flowchart of a process for vectorization of profile points.
Figure 16B:
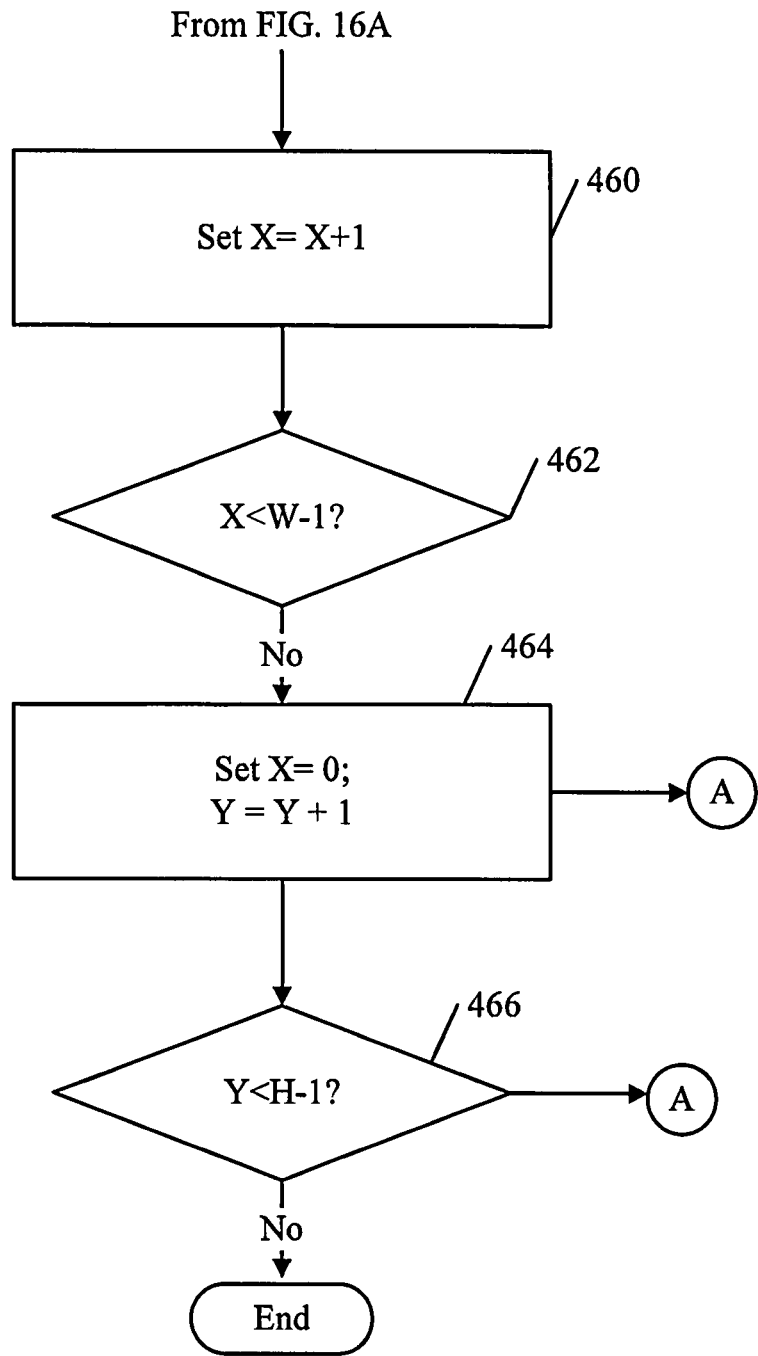

FIG. 12 illustrates a flowchart describing a process 399 for thermal mapping and automatic zoning at block 360 (shown in FIG. 11A). Process 399 for thermal mapping and automatic zoning is described in relation to the illustrations of FIGS. 13A, 13B, 13C, 14, 15A, 15B, 16A, 16B, 17A, 17B, 18, 19A, 19B, and 19C. FIG. 13A illustrates an example of an infrared thermal image. FIG. 13B illustrates an example of the human body in the infrared thermal image of FIG. 13A removed. FIG. 13C illustrates an example of an outline created of the human body in the infrared thermal image of FIG. 13A. FIG. 14 illustrates a point d in an image and direction codes of its eight neighbors. FIG. 15A illustrates points of a profile image. FIG. 15B illustrates a vectorization of the profile image. FIGS. 16A and 16B illustrate a flowchart of a process 450 for vectorization of profile points.

Figure 19:
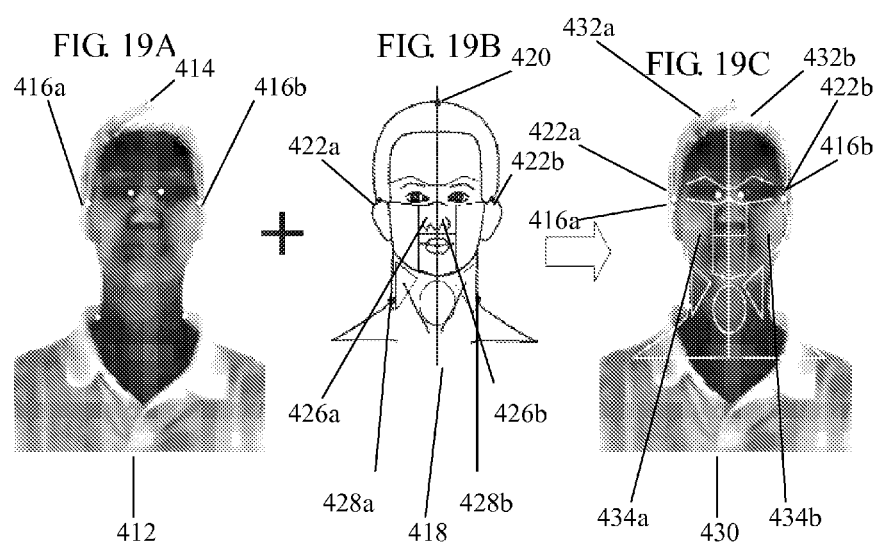
FIGS. 19A, 19B, and 19C illustrate a depiction of the thermal mapping process at different stages of FIG. 12.

FIGS. 19A, 19B, and 19C illustrate a depiction of the thermal mapping process at different stages of FIG. 12.

The process 399 (shown in FIG. 12) for thermal mapping and automatic zoning begins at block 400 where loading an infrared image, such as shown in FIG. 13A, takes place. The infrared image is processed into mathematical data such that the image can be compared against a standard template and mapped into zones. Examples of zones are shown in FIGS. 17A, 17B, and FIG. 18. FIGS. 17A and 17B illustrate an innervation-based zoning template for a front and back view of the human anatomy and FIG. 18 illustrates a facial zoning template. Once the infrared image is loaded at block 400 and the human profile is mapped at block 401, the infrared image is vectorized at block 402. The infrared image is vectorized to create a vectorized human profile represented in the infrared image, as shown in FIG. 15B.

Once the human profile image is vectorized, at block 402, the locations of characteristic reference points are determined at block 404. In FIGS. 17A and 17B, the black dots represent characteristic reference points for the innervation-based zoning template for a front and back view of the human anatomy. The black dots in FIG. 18 represent the characteristic reference points for the facial zoning template (See FIG. 19B). These characteristic reference points are common hot spots which can be found on every human. Once the characteristic reference points are found (See FIG. 19A), block 404 is followed by block 406. At block 406, a standard zoning template shown in FIGS. 17A and 17B or FIG. 18 corresponding to the position code of the infrared image is retrieved. The position code references the image capture positions (also referred to as the "predefined infrared positional images" of FIGS. 21A-21R). Block 406 is followed by block 408 where the standard template zones are scaled to match the infrared image using the characteristic reference points. Once the standard template zones, shown in FIG. 19B are matched, block 408 is followed by block 410, where the infrared image is divided into mapped zones, as shown in FIG. 19C.

The human infrared thermal mapping zoning involves image processing and mode identification technologies. The zoning is intended to automatically collect the temperatures of the respective zones on the human infrared thermal mapping and to help with medical statistics and diagnosis.

In light of the needs in medical research and clinical diagnosis, the infrared thermal image can be zoned from different medical perspectives, as from the perspectives of anatomy, innervation, and pains. Such zonings are based on a standard human body (anatomy). Each group of zones includes geometrical parameters like profiles, zoning lines, and positioning reference points.

FIGS. 17A and 17B illustrate an innervation-based zoning template for a front and back view of the human anatomy and FIG. 18 illustrates a facial zoning template. The facial zoning template of FIG. 18 is based on diseases of the upper respiratory tract. Each template consists of profiles, geometrical zoning lines (shown in FIG. 19C as white lines), and positioning reference points (shown in FIG. 19A as white dots). All the parameters can be scaled up or down. FIGS. 17A, 17B, and 18, as well as other zoning templates, are used as standard zoning graphs (PPG).

The vectorization of the thermal image or human profile begins by capturing a human profile from a thermal image of the patient's body. The vectorial human profile is p from infrared thermal image (I) (where I can be a gray image). There are multiple algorithms for image profile capture. Although several different methods may be utilized, in one example, a threshold-gradient method is used.

The threshold-gradient method is utilized to separate the human body from the background in the thermal image, as shown in FIG. 13B. The threshold-gradient method can then be used to take the boundaries and vectorize them, as shown in FIG. 13B.

The threshold-gradient method is utilized to calculate a threshold V to take the human image in the infrared thermal image I, shown in FIG. 13A, according to equations Eq. (1a) and (1b) defined as $$I(y, x) = I; 0 \le y \le H - 1; 0 \le x \le W - 1 \quad \text{Eq. (1a)}$$

then, $$V = \frac{1}{H \times W} \sum_{y=0}^{y=H-1} \sum_{x=0}^{x=W-1} I(y, x) \quad \text{Eq. (1b)}$$

where, H and W stand for height and width of I.

Image G in FIG. 13B can be obtained by equation Eq. (2) defined as:

$$G(x, y) = \begin{cases} 1, & \nabla I(x, y) \ge V \\ 0, & \nabla I(x, y) < V \end{cases} \quad \text{Eq. (2)}$$

where image G is a two-valued image, of which the white part is 1 (i.e., G1), which covers the body area in the infrared thermal image I (FIG. 13A); and the black part is 0, corresponding to the background. The profile p can then be determined, as shown in FIG. 13C.

To determine the profile p, the following gradient operator G in equation Eq. (3) can be used to convolute G and to get boundary profile image P:

$$S_x = \begin{bmatrix} -1 & 0 & 1 \\ -1 & 0 & 1 \\ -1 & 0 & 1 \end{bmatrix} \quad \text{Eq. (3)}$$

$$S_y = \begin{bmatrix} -1 & -1 & -1 \\ 0 & 0 & 0 \\ 1 & 1 & 1 \end{bmatrix}$$

where Sx and Sy stand for 3×3 convolution templates in the horizontal and vertical directions, and the convolution formula is shown in equations Eq. (4a), (4b), and (4c):

$$g_x(x, y) = \sum_{i=0}^{3-1} \sum_{j=0}^{3-1} S_x(i, j)G(x+i, y+j) \quad \text{Eq. (4a)}$$

$$g_y(x, y) = \sum_{i=0}^{3-1} \sum_{j=0}^{3-1} S_y(i, j)G(x+i, y+j) \quad \text{Eq. (4b)}$$

$$P(x, y) = \sum_{x=0}^{W-1} g_x(x, y) + \sum_{y=0}^{H-1} g_y(x, y) \quad \text{Eq. (4c)}$$

Next, vectorize the P(x,y) to get the body profile p.

As discussed earlier, FIG. 14 illustrates a point d in an image and direction codes of its eight neighbors. The vectorization process is described in relation to FIGS. 14, 15A, 15B. The vectorization process begins by defining the direction denotation code, point d in the image, and the direction codes of its eight neighboring points as illustrated FIG. 14.

FIG. 15A exemplifies the vectorization of a profile image P. After finding the first point from left to right and from top to down (i.e. bottom), in an counter-clockwise direction (consistent with the changes of the direction code), as shown in FIGS. 14, 15A, and 15B, vectorial parameters of the boundary profile are obtained. Examples of vectorial parameters are as given in Table 1. The SN 1 is denoted by Ptop and SN 8 is denoted by Pdown. Process 450 for vectorization of profile points is shown in FIGS. 16A and 16B, and explained below.

TABLE 1

| SN | X Coordinate | Y Coordinate | Direction Code |
|----|--------------|--------------|----------------|
| 1  | 3 | 0 | 6 |
| 2  | 3 | 1 | 5 |
| 3  | 2 | 2 | 6 |
| 4  | 2 | 3 | 5 |
| 5  | 1 | 4 | 6 |
| 6  | 1 | 5 | 7 |
| 7  | 2 | 6 | 7 |
| 8  | 3 | 7 | 1 |
| 9  | 4 | 6 | 1 |
| 10 | 5 | 5 | 2 |
| 11 | 5 | 4 | 2 |
| 12 | 5 | 3 | 2 |
| 13 | 5 | 2 | 2 |
| 14 | 5 | 1 | 3 |
| 15 | 3 | 0 | 4 |

In FIG. 16A, process 450 begins at block 452 where X, Y, and I are all set to zero (0). The direction code (OC) is set to 3 in this example. However, the OC may change or may be assigned to a different value.

Block 452 is followed by block 454 where image points in the skeleton map within the field 8 of P(x,y) are searched. Block 454 is followed by block 456 where a determination is made whether points are found. If the determination is "Yes," the down coordinates are acquired and noted for point(x,y). The direction code (OC) and $P_x$ and $P_y$ are defined by equations Eq. (5a), (5b) and (5c)

$$P_x(i)=X; \quad \text{Eq. (5a)}$$

$$P_y(i)=Y; \text{ and} \quad \text{Eq. (5b)}$$

$$\text{If } i>0 p_d(i-1)=OC. \quad \text{Eq. (5c)}$$

In FIGS. 16A and 16B, X and Y stand for the change coordinates of image points, I for the record index of profile points found, and OC for the direction code corresponding to FIG. 14. The direction code OC changes counter-clockwise. The result of the direction code OC depends on the azimuth relation between the profile point found at a present and the last point (shown in FIGS. 15A and 15B).

Referring again to block 456, if the determination is "No," then X (the X coordinate) is incremented by one (1) at block 460. Likewise, block 458 is followed by block 460 to increment X. Block 460 is followed by block 462 where a determination is made whether X is less than W-1 (width -1). If the determination is "Yes," block 462 (shown in FIG. 16B) returns or loops back to block 454 (shown in FIG. 16A). However, if the determination is "No" at block 462, then block 462 is followed by block 464. At block 464, X is set to 0 and the Y is incremented by one (1). Block 464 is followed by block 466 where a determination is made whether Y is less than H-1 (height -1). If the determination is "No," process 450 ends. Otherwise, block 466 returns or loops back to block 454.

The process for block 406 (shown in FIG. 12) relates to retrieving standard zoning templates corresponding to a position code. The position codes are attribute codes indicating body parts, arbitrarily defined for image collection of the infrared image. It is possible to control the program to take the characteristic positioning marks of the image. The i is an index serial number. From the thermal mapping, take position A(i) according to equation Eq. (6a) defined as $$A(i) \in G_1 \quad \text{Eq. (6a)}$$

where A(i) is an element of the set of points in the human image zone, $G_1$. A(i) includes the inner canthus, the upper fossa of the collarbone, the axilla, the umbilicus, the groin, and the lumbosacral portion, which are relatively warmer places in the human body called physiological hot zones. From the human profile, take special points B(i) according to equation Eq. (6b)

$$B(i) \epsilon p \quad \text{Eq. (6b)}$$

where B(i) is an element of the set of points in the vectorial human profile, p. B(i) includes points in the head top, the tip of the ear, the neck, the axilla, the femoral-genital joint, the wrist, the tips of the palm, the ankles, the toes, and the heel. Positions A and B may have a data structure comprising position coordinates and corresponding body zone attribute codes.

The process for block 408 (shown in FIG. 12) relates to scaling standard temperature zones to match infrared image utilizing characteristic reference points. After taking A(i) and B(i), the human infrared thermal mapping can be matched with standard zoning graphs (as shown in FIGS. 19A, 19B, and 19C). The process begins with selecting and retrieving a standard zoning graph PPG(i) from the database according to the zoning type and position code of the infrared image. A coordinate system CS of the infrared thermal mapping according to A(i) and B(i) is then calculated. After that, the proportional relations $K_x$ and $K_y$ of the body image $G_1$ according to A(i) and B(i) are computed. Then the relevant parameters of the standard zoning graph PPG(i), according to $K_x$ and $K_y$, are scaled to get $P_u$. Then $G_1$ (or g) is matched with $P_u$-align A(i), and B(i) is matched with $P_u$ positioning reference points.

The process for block 410 (shown in FIG. 12) relates to dividing infrared images into mapped zones. According to the coordinate system CS, human profile g and zoning lines in $P_u$, divide $G_1$ to get a series of closed areas in CS, and finally get the medical zoning of human infrared mapping.

As explained earlier, FIGS. 19A, 19B, and 19C illustrate a depiction of thermal mapping and process at different stages of FIG. 12. Similar to block 400 (shown in FIG. 12), a thermal image 412 of a respiratory scan is loaded. The vectorization in block 402 (shown in FIG. 12) enables the following mathematical processes to take place. Step 404 (shown in FIG. 12) determines markers 414, 416a, and 416b, which represent some of the determined characteristic reference points for this image. Image 418 (shown in FIG. 19B) represents the standard zoning template for the respiratory scan which is loaded by step 406 (shown in FIG. 12). Image 418 contains several characteristic reference points 420, 422a, and 422b, which correspond to the same characteristic reference points indicated by markers 414, 416a, and 416b on image 412 (shown in FIG. 19A). Characteristic reference points on the template are used to define the image into zones indicated by sections 426a, 426b, 428a, and 428b. Step 408 (shown in FIG. 12) combines thermal image 412 with image 418 and scales the standard zones to best fit zones placed on a mapped image 430 (shown in FIG. 19C). Mapped image 430 represents the end result of step 410 (shown in FIG. 12) by depicting the newly mapped zones represented by areas 432a, 432b, 434a, and 434b. Such mapped zones represent key interest areas for which thermal data may be interpreted and analyzed.

Figure 20:
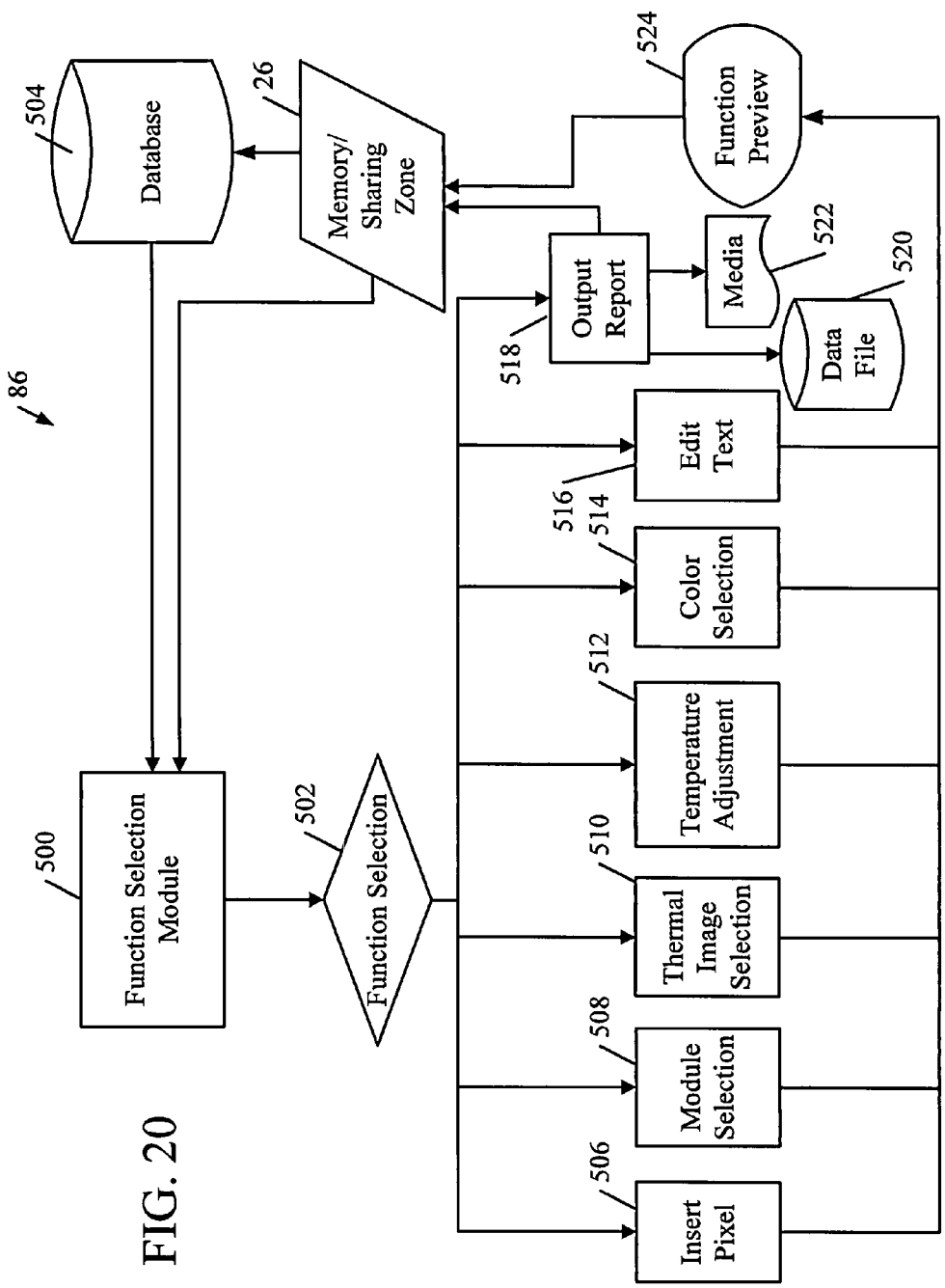
FIG. 20 illustrates a software flowchart depicting a report output module.

FIG. 20 illustrates a flowchart depicting ROM 86 (shown in FIG. 4). ROM 86 gathers processed information from other modules and allows a user to format and customize the output of a report. ROM 86 includes a function selection module denoted at block 500, which links to a database 504 and memory or sharing zone 26 to pool information. Block 500 is followed by block 502 where a function selection is determined, which determines how and what information is displayed. The available functions/options include an insert pixel function at block 506, a module selection function at block 508, a thermal image selection function at block 510, a temperature range adjustment function at block 512, a color scheme selection function at block 514, a text editing function at block 516, and a report output function at block 518.

Insert pixel function at block 506 allows the user to insert annotations or mark areas on thermal images. The module selection function at block 508 allows the user to select a module which has a predefined report layout. The thermal image selection function at block 510 allows the user to select images to be included in the report. The temperature range adjustment function at block 512 allows for the specification of an upper and lower range of temperature values that is displayed by colors from the color scheme selection at block 514. The color scheme selection function at block 514 allows for the selection or specification of color palettes in which to represent infrared images. The text editing function at block 516 permits the user to edit pre-formatted text, or add on additional text to the report. Use of any of the editing and selection modules creates a function preview at block 524 that displays the customized report. Customized reports are passed to memory or sharing zone 26 before being stored in database 504. The report output module 518 outputs the report to either a data file 520 or to an alternative media 522 (e.g. print job). Blocks 506, 508, 510, 512, 514, and 516, are followed by block 524.

Figure 21A:
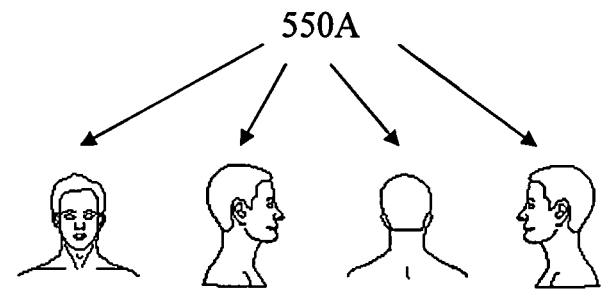
FIGS. 21A-21R illustrate pre-defined infrared positional images for use in the health evaluation system.
Figure 21B:
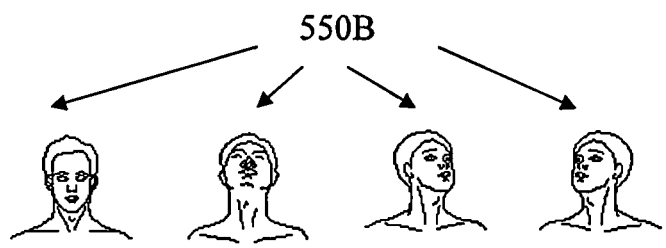
Figure 21C:
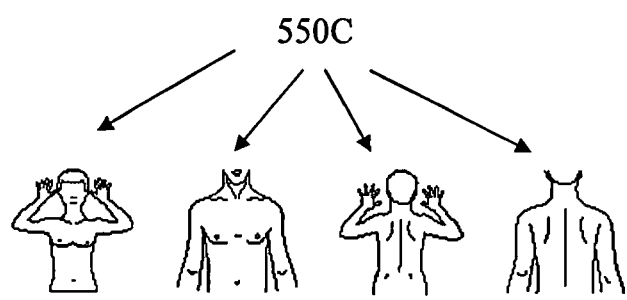
Figure 21D:
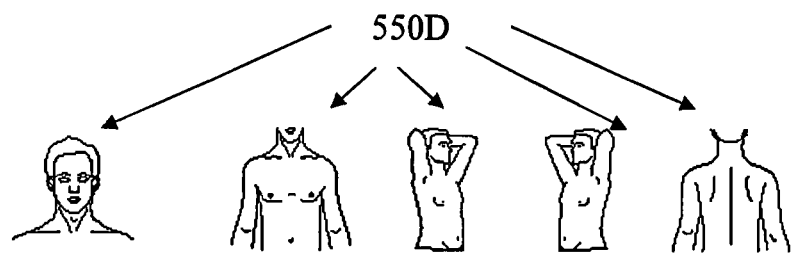
Figure 21E:
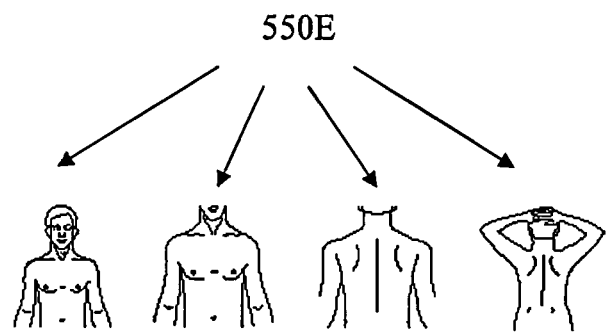
Figure 21F:
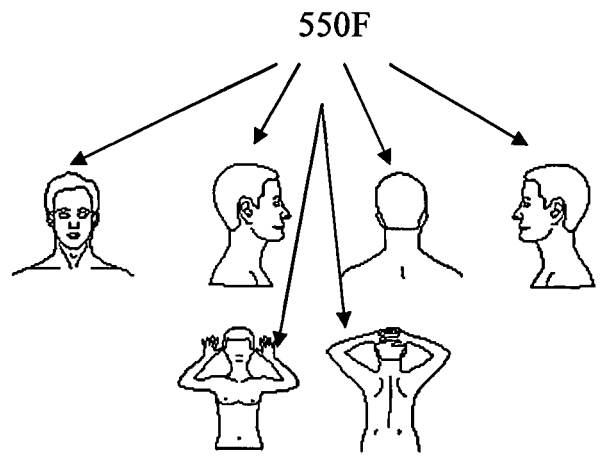
Figure 21G:
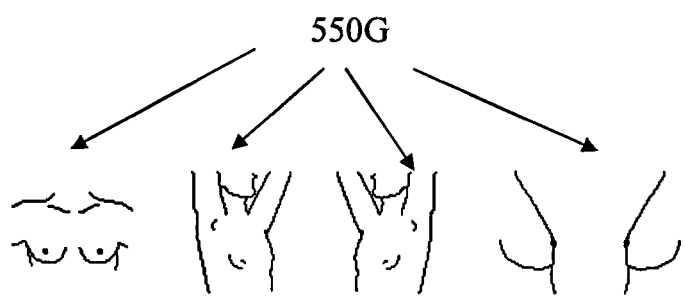
Figure 21H:
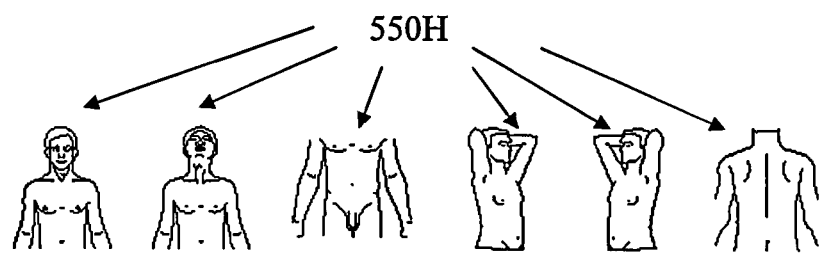
Figure 21I:
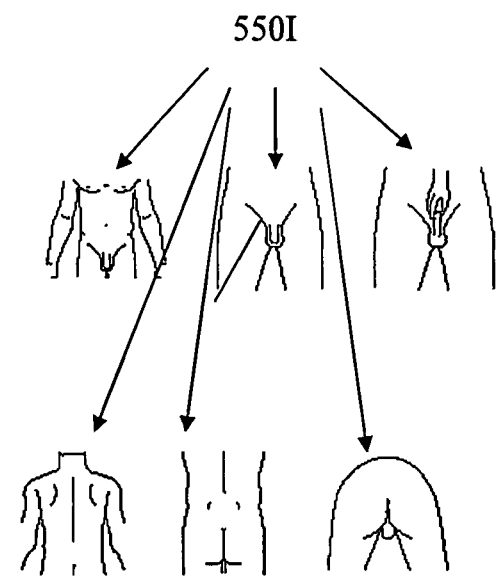
Figure 21J:
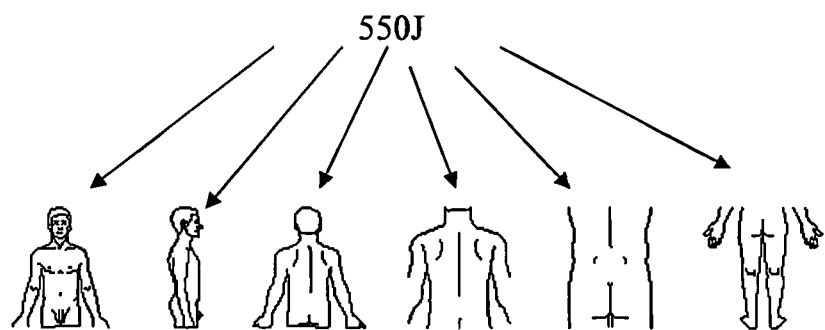
Figure 21K:
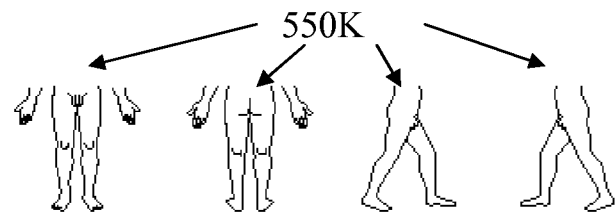
Figure 21L:
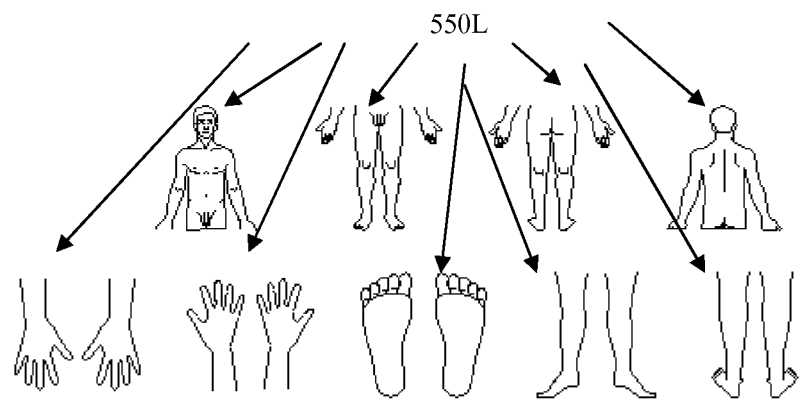
Figure 21M:
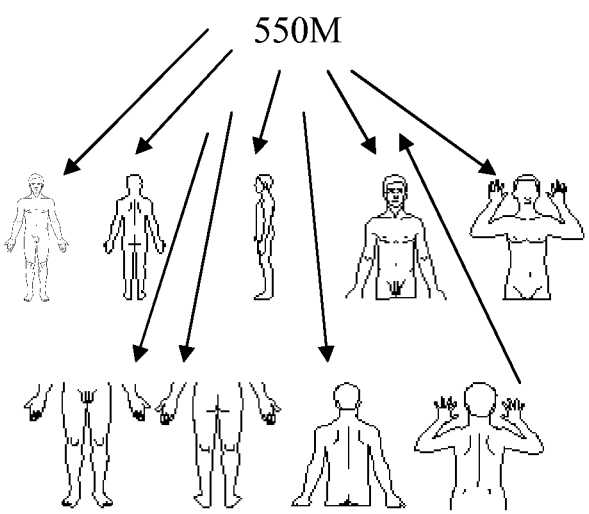
Figure 21N:
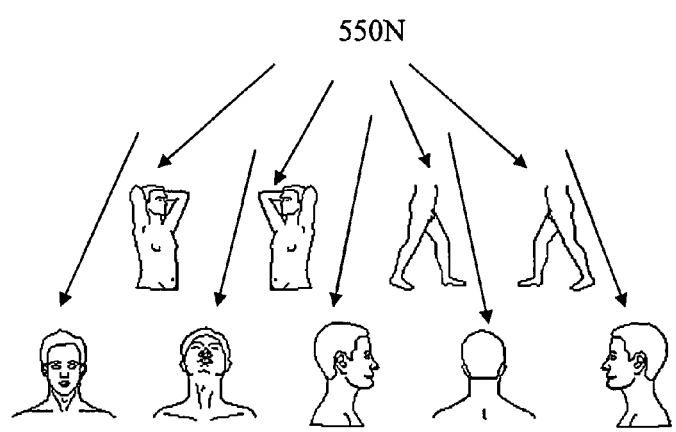
Figure 21Q:
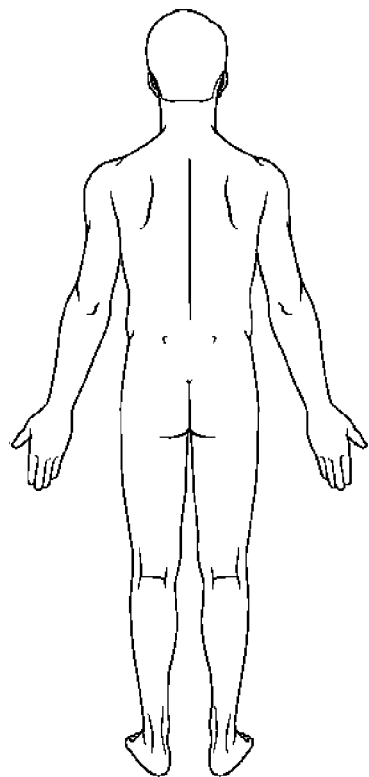
Figure 21R:
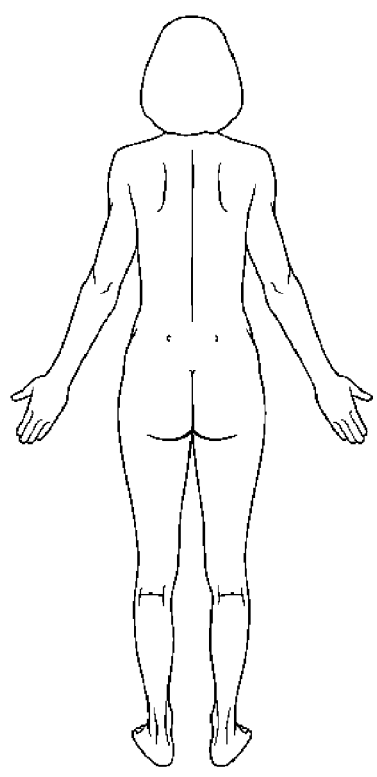

FIGS. 21A-21R illustrate predefined infrared positional images for use in health evaluation system 40 (shown in FIG. 3).

Referring now to FIG. 21A, a set of positional images 550A correspond to the brain blood supply evaluation and includes: front, right side, left side, and back of the head. Set of positional images 550A also corresponds to positions for the indications of diseases of the sense organs (eyes, nose, mouth, and ears) and includes the same positional images (550A) as with brain blood supply evaluation.

Referring now to FIG. 21B, a set of positional images 550B corresponds to positions for indications of relevant diseases of (anterior) cervical thyroid and mandibular lymph node and includes: front neck and front neck with face up, neck with face to the right and up and neck with face to the left and up.

Referring now to FIG. 21C, a set of positional images 550C corresponds to positions for the neck-shoulder syndrome and includes: front and back with hands raised (arms, neck, and head all on screen), and front and back with hands down (shoulders shown).

Referring now to FIG. 21D, a set of positional images 550D corresponds to positions for the respiratory system health status evaluation and includes: front face and front with face up (exhaling, inhaling) of head-neck part; front of the chest, back of the chest with hands around the head, and right and left slanting.

Referring now to FIG. 21E, a set of positional images 550E corresponds to positions for the myocardial blood supply evaluation and includes: front and back of head, neck, and chest.

Referring now to FIG. 21F, a set of positional images 550F corresponds to positions for the heart and brain blood supply evaluation and screening of thoracic diseases and includes the head-face positions in set of positional images 550A of brain blood supply evaluation. Set of positional images 550F also includes front and back of the chest.

Referring now to FIG. 21G, a set of positional images 550G corresponds to positions for the evaluation of mammary diseases and includes: left and right slanting positions of breasts; and left and right sides around the breasts.

Referring now to FIG. 21H, a set of positional images 550H corresponds to positions for the digestive system health status evaluation and includes: front, and front with face up of head, neck, and chest; front of the abdomen (with hands around the head), left/right front slanting, and back of trunk.

Referring now to FIG. 21I, a set of positional images 550I corresponds to positions for the urogenital system health status evaluation and includes: front/back of abdomen (legs apart); front of lower abdomen, and lower lumbosacral part. For the male only, the front of abdomen (penis in an upright position with testicles exposed, legs apart) is also included.

Referring now to FIG. 21J, a set of positional images 550J corresponds to positions for the soft tissue injury and blood supply around the spinal column and includes: front, back and side of trunk; back of cervical vertebra plus back of lumbosacral part; buttocks; and back of two lower limbs.

Referring now to FIG. 21K, a set of positional images 550K corresponds to positions for the evaluation of injuries to joints and soft tissues of lower limbs and includes: front/back of lower limbs (umbilicus-toes), and left/right stepping postures of lower limbs.

Referring now to FIG. 21L, a set of positional images 550L corresponds to positions for the functional status of blood vessels and peripheral microcirculation of four limbs and includes: front/back of upper/lower body; front/back of hand/foot; and sole.

Referring now to FIGS. 21M, 21N, 21O, 21P, 21Q, and 21R, sets of positional images 550M, 550N, 550O, 550P, 550Q, and 550R correspond to positions for the whole-body health status evaluation and includes: front/back/side of whole body; front/back of upper body; front/back of lower body; right/left slanting position of upper body; right/left slanting position of lower body; front, face up, right side, back, and left side of the head-face. FIGS. 21O and 21Q represent male front and back whole body images 550O and 550Q for use in set 550M. FIGS. 21P and 21R represent female front and back whole body images 550P and 550R for use in set 550M.

Figure 28:
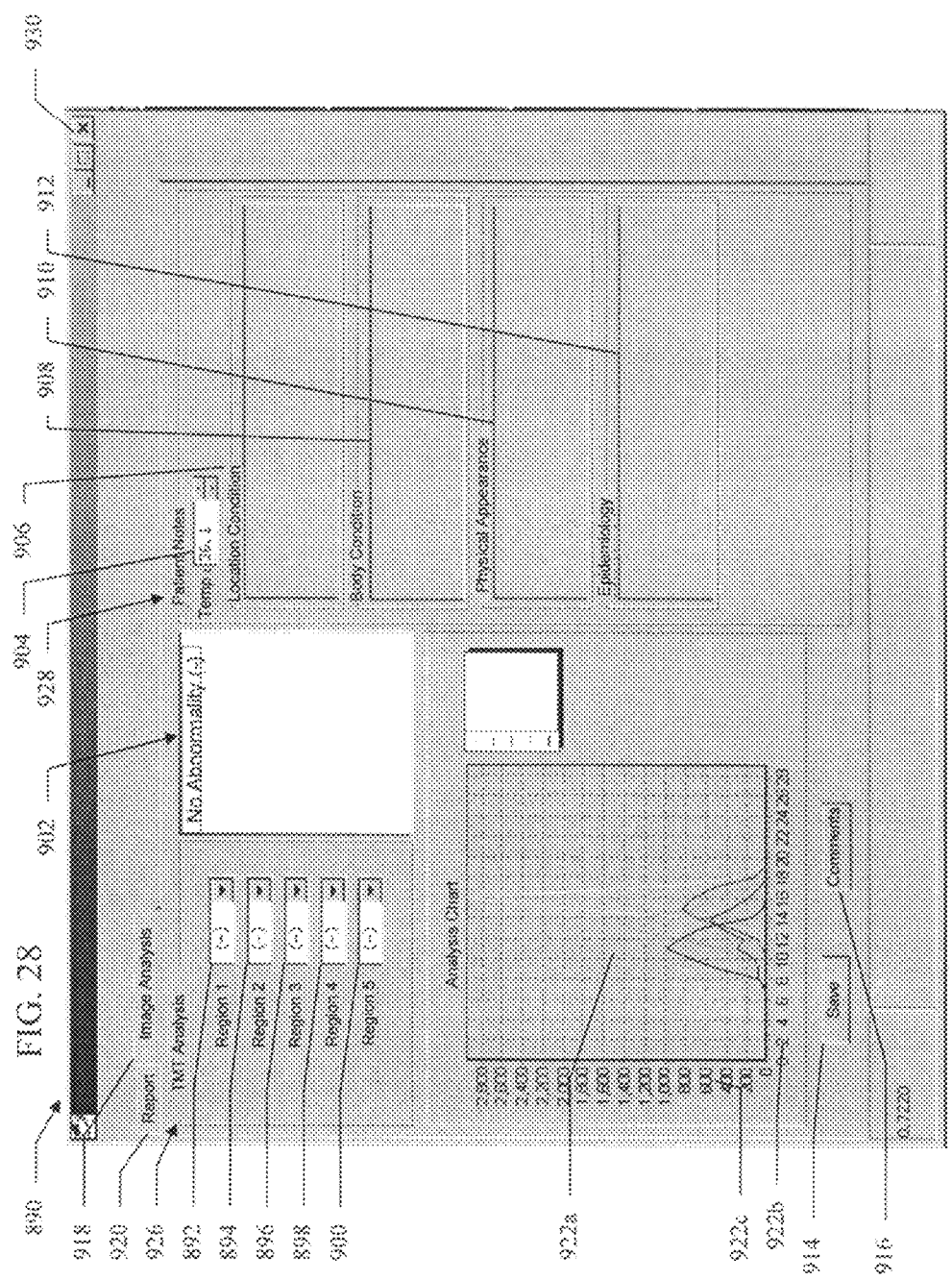
FIG. 28 illustrates an embodiment of thermal image analysis GUI.
Figure 29:
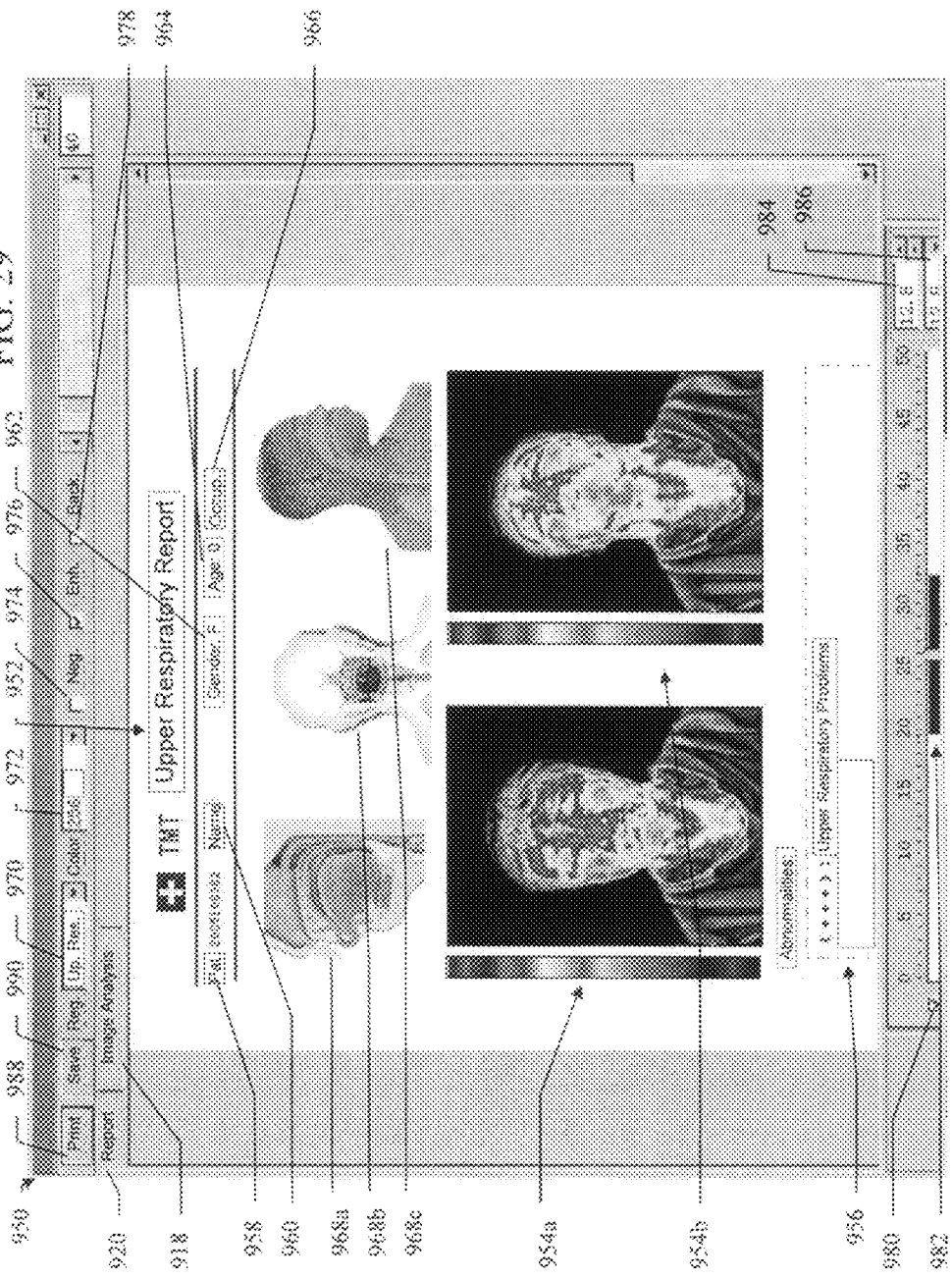
FIG. 29 illustrates an embodiment of a patient report preview GUI.
Figure 30:
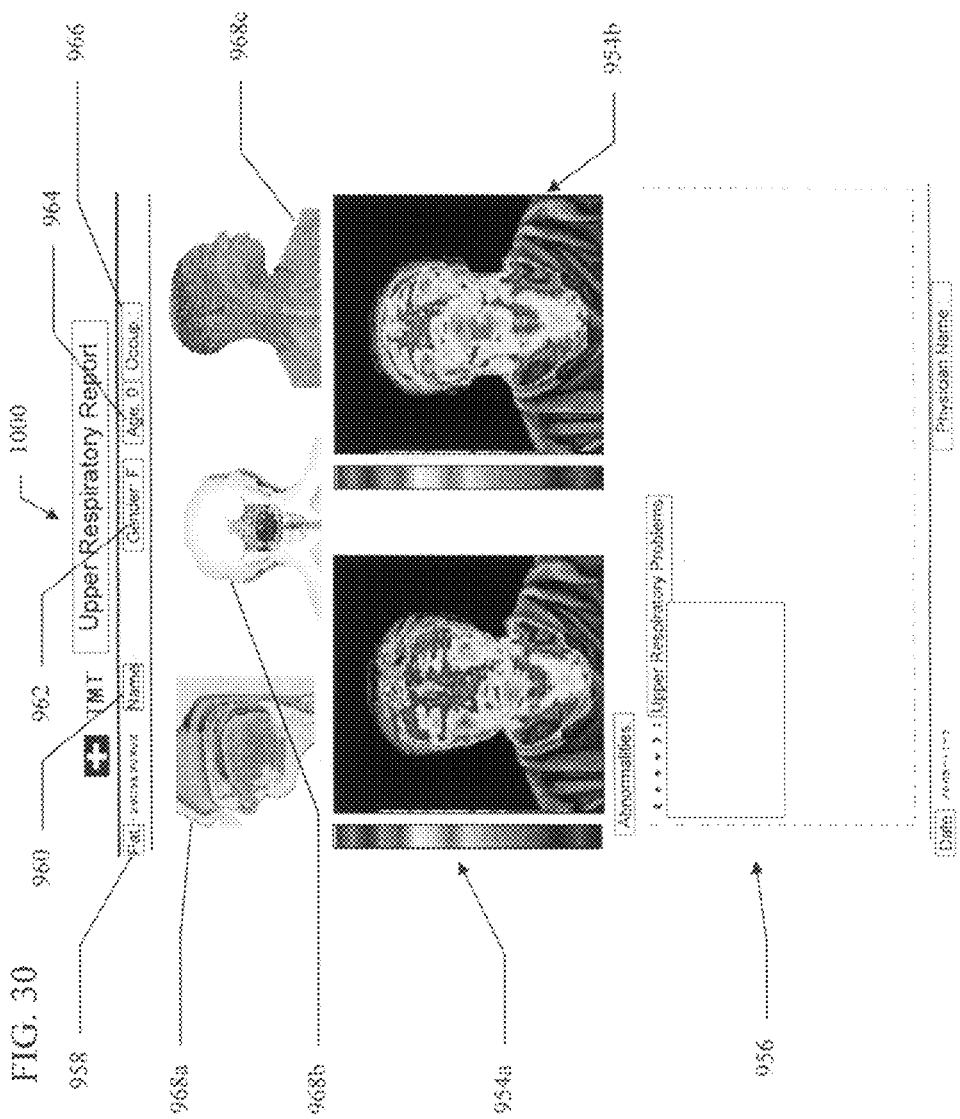
FIG. 30 illustrates an embodiment of a patient report printout.

FIGS. 22 through 32 represent GUIs implemented by health evaluation system 40. FIGS. 22-29 are examples of GUIs to enable the user to customize and create scans. FIG. 30 illustrates one embodiment of a patient report printout 1000. The GUIs contain a database of patient files with numerous information fields. Through these options, the user can create new patient files, edit patient files, take IR thermal images of patients, analyze the thermal images, and print a report of the analysis by activating a corresponding GUI. These GUIs' are described later.

Figure 33:
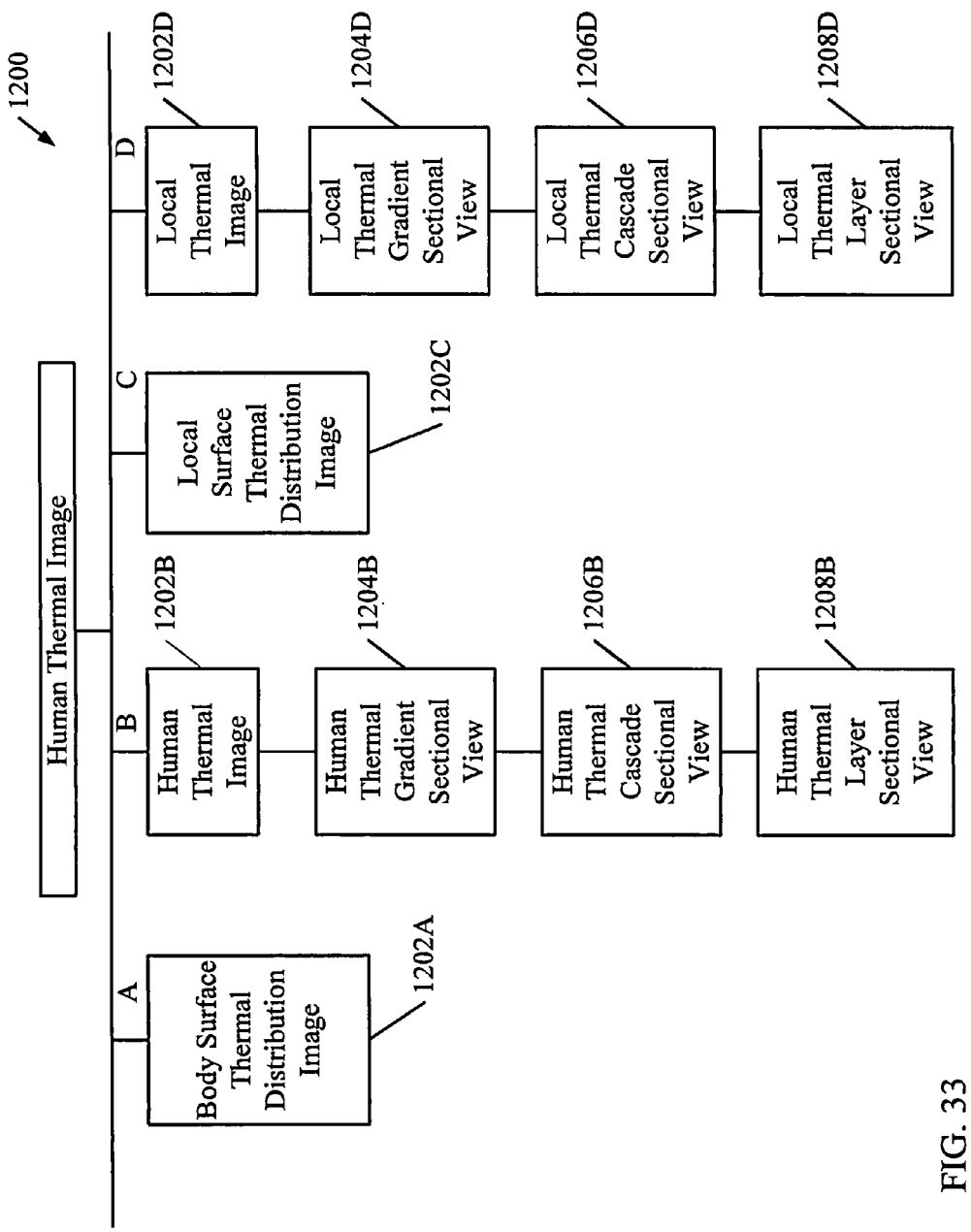
FIG. 33 illustrates a block diagram of a thermal image mapping process.

FIG. 33 illustrates a block diagram of a thermal image mapping process 1200, which has four paths identified as four parallel lines: A, B, C, and D. At block 1202A, initially the body surface thermal distribution image is first taken. This initial, unmodified thermal image is known as a static or passive thermal image. An example of a body surface thermal distribution image is shown in FIG. 13A.

Figure 40A:
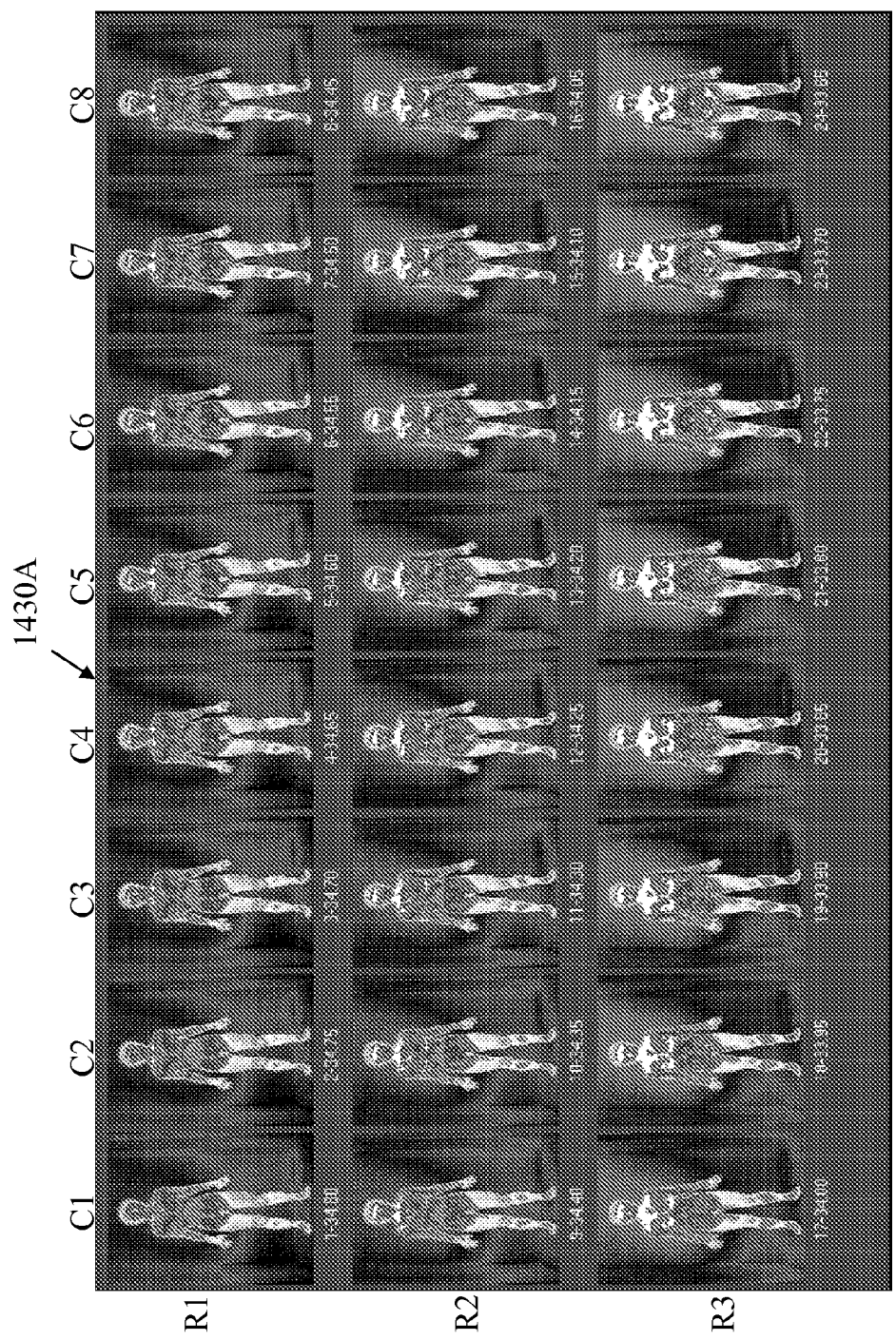
FIGS. 40A, 40B, and 40C illustrate a representation of sectional views from the cascade chromatography process.
Figure 40B:
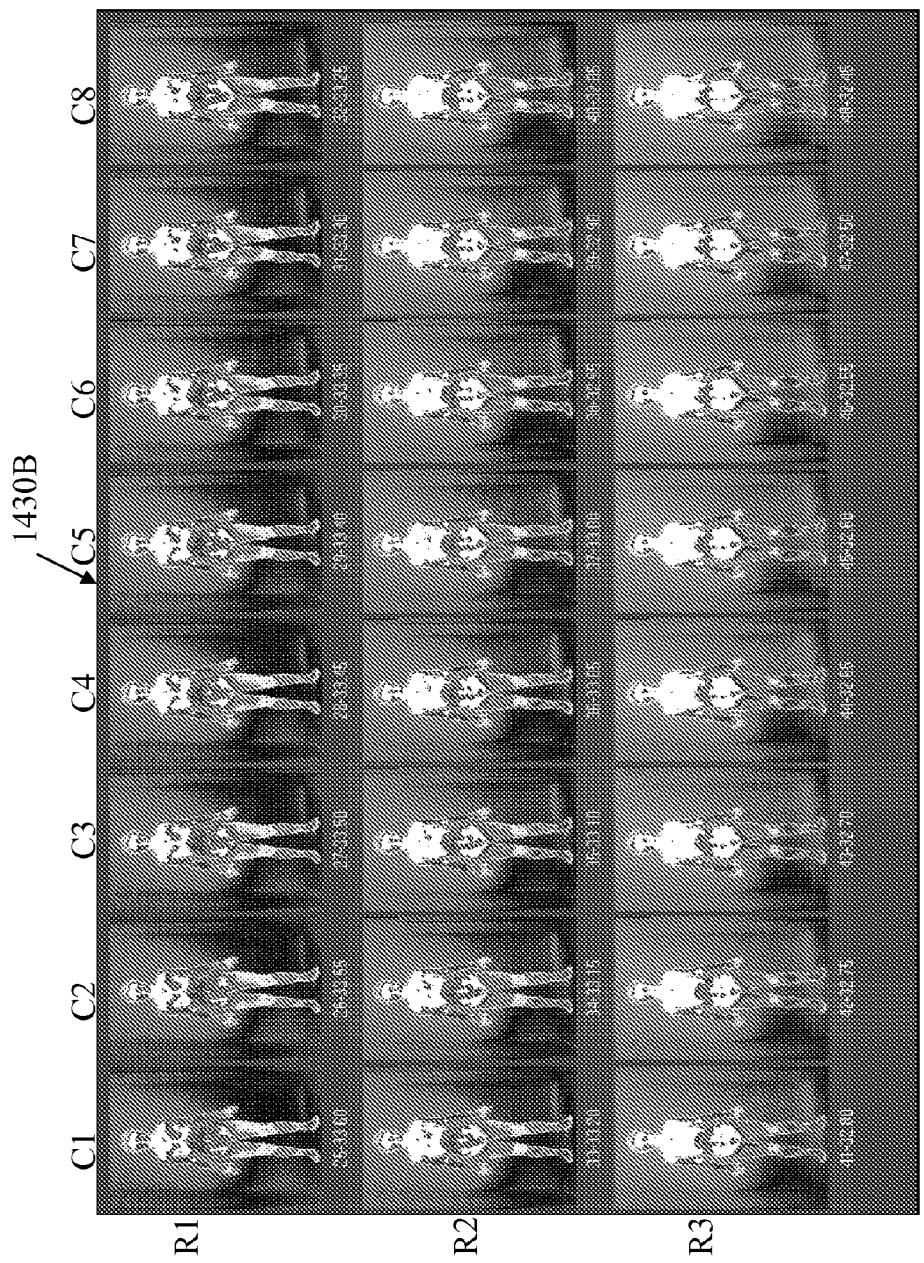
Figure 40C:
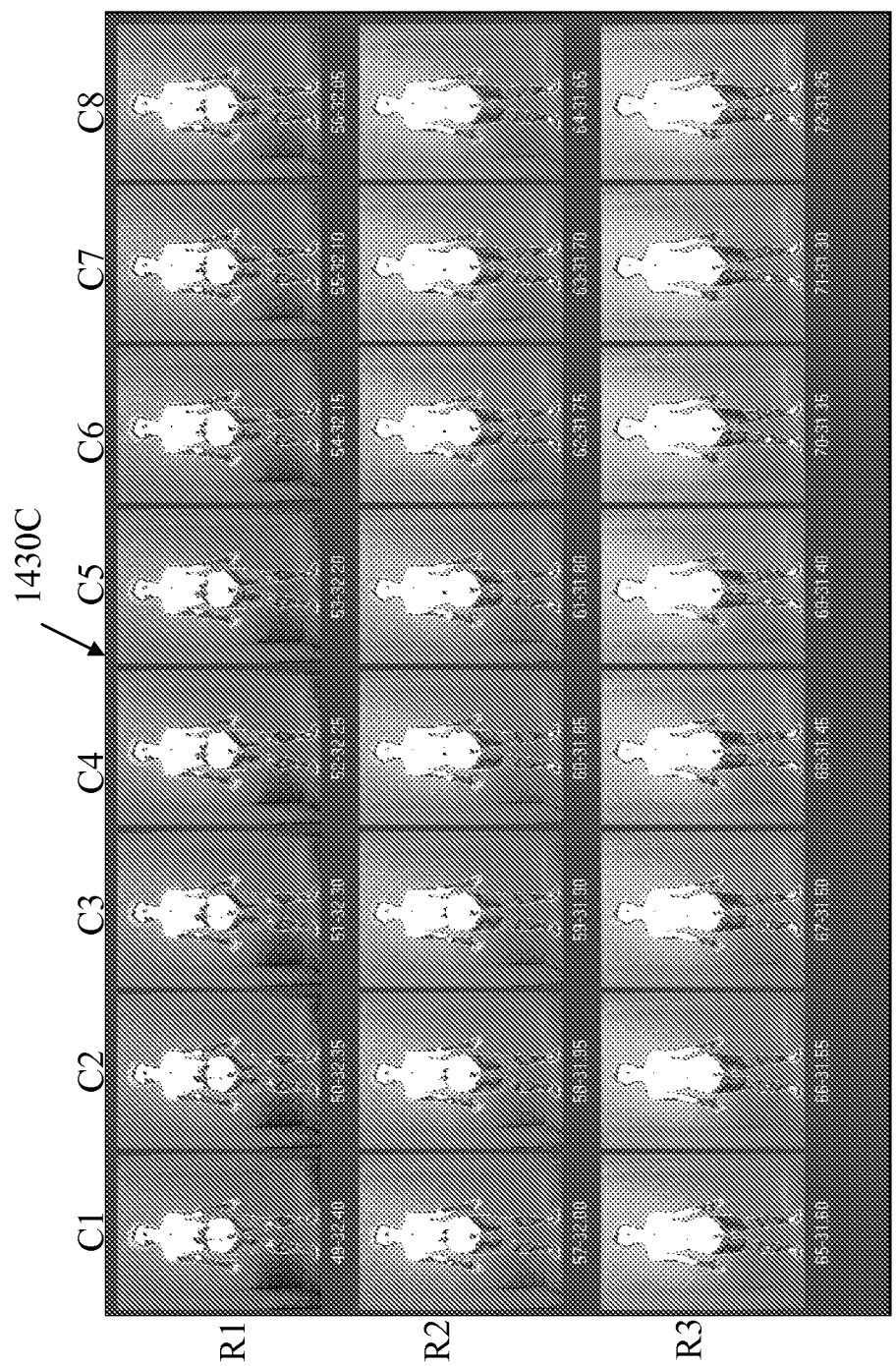

At path B, once a human thermal image at block 1202B is obtained, a human thermal gradient sectional view is generated at block 1204B (shown in FIGS. 40A, 40B, and 40C). After that, a human thermal cascade sectional view is generated at block 1206B. Here the image is processed with vectorization to remove the background, as seen in FIG. 13C. The human thermal cascade sectional view at block 1206B is the image processed with cascade chromatography to determine areas of abnormal temperature.

In the cascade chromatography process, each thermal image is composed of a plurality of pixels (such as, 320×240), where every pixel contains temperature data and positional data. The temperature data in the pixel is represented in the image by a corresponding color. The user defines which colors represent which temperatures. The positional data positions the pixel at a particular point on the body. In FIGS. 40A, 40B, and 40C, a series of dynamic thermal images is shown. The cascade chromatography process begins the analysis at the highest temperature detected in the body. In FIG. 40A, the highest temperature is set at 34.80 degrees Celsius, as shown in the image at row R1, column C1. Therefore, 34.80 degrees Celsius is the first reference temperature used for the analysis. The cascade chromatography process begins by organizing the pixels from highest temperature to lowest temperature. All pixels that contain temperature data equal to or greater than the reference temperature (34.80 degrees Celsius in image R1, C1) are compared. In one embodiment, these pixels are compared to pixels with symmetric positional data. The human body is generally symmetric. Therefore, pixels at symmetric positions of the body should have equal temperature data. For example, the pixel at the tip of the index finger in the right hand should have equal temperature data as the pixel at the tip of the index finger in the left hand. The symmetries are defined by preset zones in the program. If the temperature variation $\Delta T$ is 0, then there is no abnormality, and the pixels being compared are changed to white (or whatever color is defined by the user for the highest temperature). Otherwise, the pixels are left unaltered. Then the reference temperature decreases by a user-defined amount. For example, in FIGS. 40A, 40B, and 40C, the temperature decreases by 0.05 degrees. The system then compares the set of pixels with the next highest temperature data in the same manner. The analysis continues until every pixel within the body in the thermal image is scanned.

As FIG. 33 illustrates, the human thermal layer sectional view at block 1208B occurs once the human thermal cascade section view at block 1206B is complete. Once areas of abnormalities have been identified, the human thermal layer section view at block 1208B utilizes a depth algorithm to determine the level at which the temperature abnormality exists within the patient's body. For example, an abnormal temperature on the surface can indicate a skin condition, while an abnormal temperature deeper in the body can indicate a problem with an organ.

At path C, a local surface thermal distribution image at block 1202C is obtained only for a specific anatomic zone to be analyzed. Thus, the analysis is localized.

At path D, the local thermal image at block 1202D is obtained only for a specific anatomic zone to be analyzed. Block 1202D is followed by block 1204D where a local thermal gradient view is generated. At block 1204D, only the specific anatomic zone is vectorized. At block 1206D, a local thermal cascade sectional view is generated and only the specific anatomic zone is compared. Block 1206D is followed by block 1208D where a local thermal layer sectional view is generated if there is an abnormality in the specific anatomic zone. Health evaluation system 40 (shown in FIG. 3) also determines whether the abnormality is on the surface or internal. Path D creates the same views as path B. However, the vectorization and cascade chromatography is performed only for a specific zone or location.

When doing depth analysis, system 40 generates a three-dimensional analysis of a two-dimensional thermal image, as seen in FIGS. 41A, 41B, 42A, 42B, 43A, and 43B. These thermal images are composed of TMT maps. The term "micro" refers to a specific anatomic zone during the thermal image analysis. The term "texture" is defined, as is used in computer graphics, as an array of pixel data, either in two or three dimensions, where each pixel can contain color, luminance, or other information.

Figure 34:
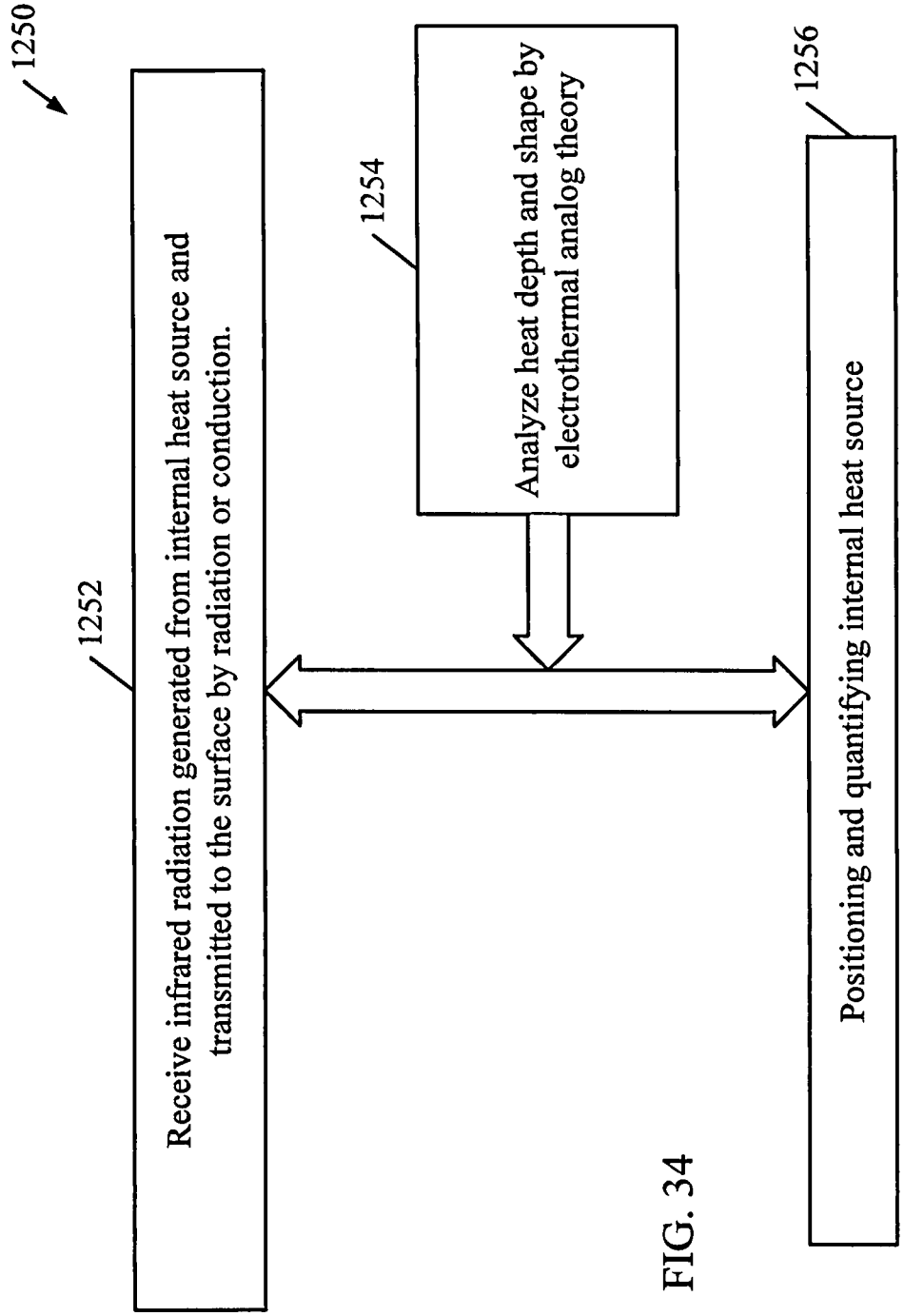
FIG. 34 illustrates an example of a block diagram of an auto-analysis with heat depth evaluation.

FIG. 34 illustrates an example of a block diagram of an auto-analysis 1250 with heat depth evaluation. Auto-analysis 1250 with heat depth evaluation begins at block 1252 where infrared radiation is received from an internal heat source and transmitted to the surface by radiation or conduction. Block 1254 analyzes the heat depth and shape by electrothermal analog theory. At block 1256, the internal heat source is positioned and quantified.

Figure 35:
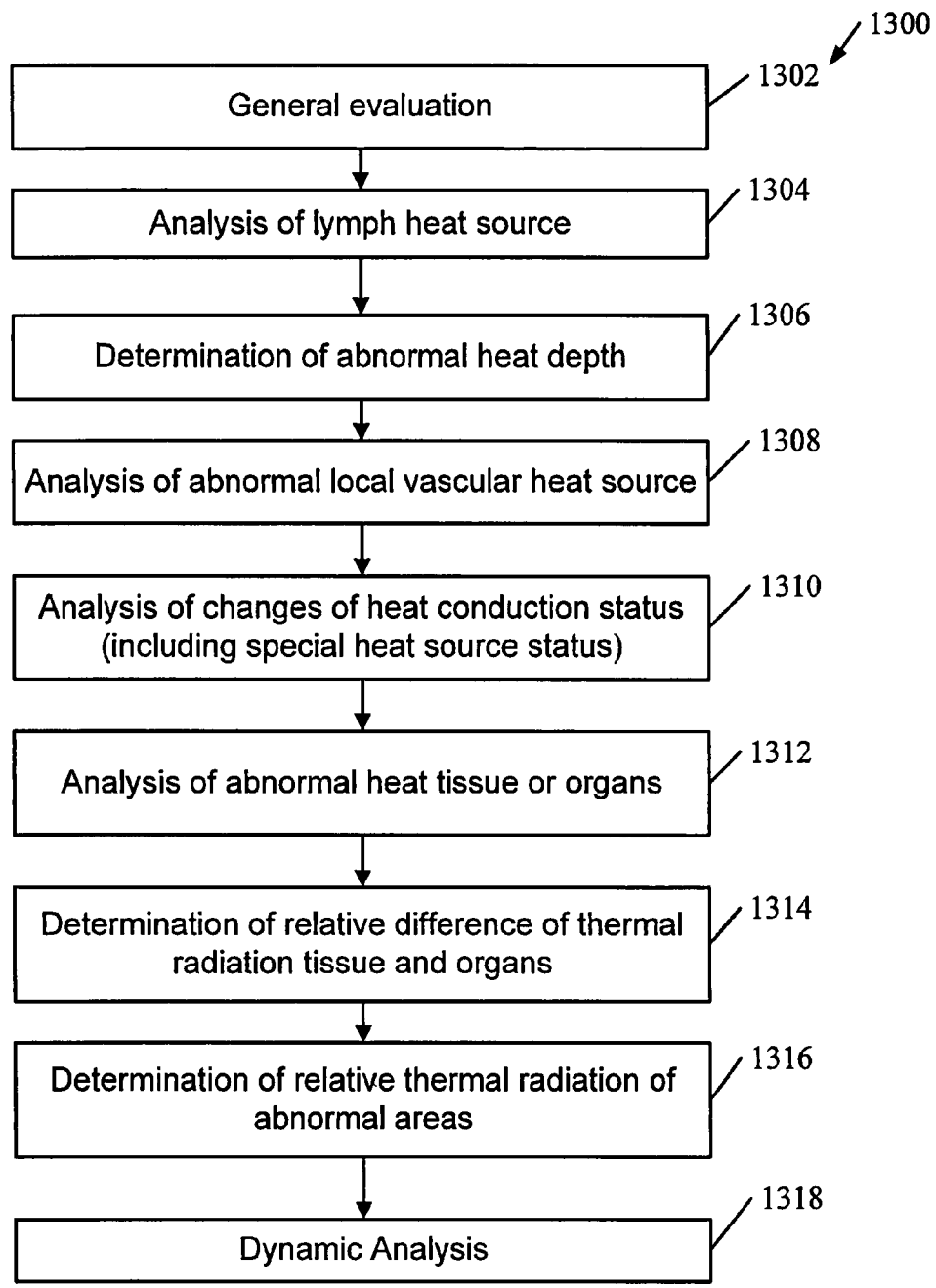
FIG. 35 illustrates a flowchart of one embodiment of an auto-analysis.

FIG. 35 illustrates a flowchart of one embodiment of an auto-analysis 1300. Auto-analysis 1300 begins with a general evaluation at block 1302 of the thermal image or mapping. Block 1302 is followed by block 1304 where analysis of a lymph heat source takes place. Block 1304 is followed by block 1306 where a determination of abnormal heat depth is made. Block 1306 is followed by block 1308 where an analysis of abnormal local vascular heat source is performed. Block 1308 is followed by block 1310 where an analysis of changes of heat conduction status (including special heat source status) is made. Block 1310 is followed by block 1312 where an analysis of abnormal heat of tissues organs is made. Block 1312 is followed by block 1314 where a determination of relative difference of thermal radiation of tissues and organs is made. Block 1314 is followed by block 1316 where a determination of the relative thermal radiation of abnormal areas is made. Block 1316 is followed by block 1318 where a dynamic analysis is performed. In various configurations, the flowchart blocks above are performed in the depicted order, or these blocks or portions thereof may be performed contemporaneously, in parallel, or in a different order. Furthermore, one or more of the blocks may be omitted for a particular evaluation and analysis depending on the type of the analysis desired.

Health evaluation system 40 (shown in FIG. 3) is designed to capture and detect, among other sources, metabolic heat sources of normal cells, tissues and organs; metabolic heat sources of inflammatory tissues and organs; metabolic heat sources of benign tumor tissues; metabolic heat sources of hyperplastic cell tissues; metabolic heat sources of cancerous cells; metabolic heat sources of allergic tissues; metabolic heat sources of functional status; and metabolic heat sources of tissues resulting from other external factors.

Health evaluation system 40 is also designed to detect surface heat sources, superficial heat sources, deep heat sources, non-planar internal heat sources, tubular heat sources, hollow heat sources, heat sources under hairs, special heat sources, and other heat sources.

Figure 36:
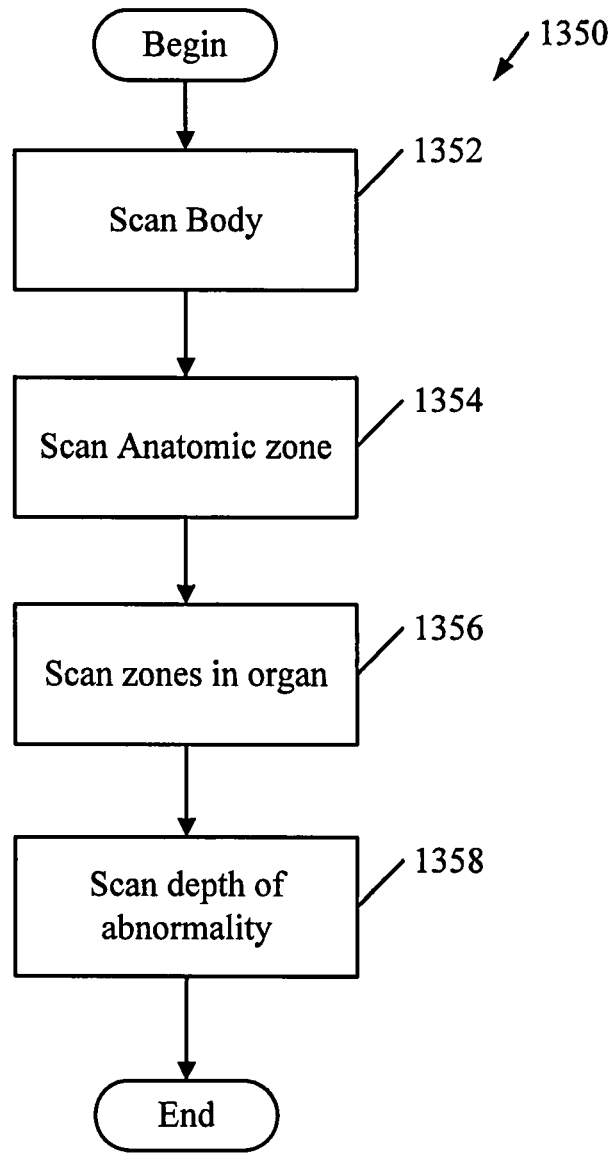
FIG. 36 illustrates a general flowchart of image processing process.

FIG. 36 illustrates a general flowchart of image processing process 1350 utilized by health evaluation system 40 (shown in FIG. 3). One or more of the steps may be omitted as needed. Process 1350 begins at block 1352 where the body is scanned or an image is captured. Block 1352 is followed by block 1354 where a sub-anatomic zone is scanned. Block 1354 is followed by block 1356 where zones in an organ are scanned. Block 1356 is followed by block 1358 where depth of an abnormality is scanned.

In one embodiment, health evaluation system 40 (shown in FIG. 3) is utilized to analyze an anatomic system (digestive system, circulatory system, etc). This analysis cannot rely on symmetry to determine temperature abnormalities since organs are not necessarily symmetric. When analyzing organs, health evaluation system 40 relies on the energy efficiency of cells to determine whether there are abnormalities. For example, a healthy cell takes organic compounds and metabolizes them, turning the compounds into energy and waste. A healthy cell typically operates around 40% efficiency, with 60% of the energy in the process being output as waste. A cancerous cell, however, has a much lower efficiency, typically around 8-9%, with the rest of the energy in the process being wasted. Cancerous cells thus output more heat than a healthy cell, and cancerous growths appear as areas with abnormally high temperatures.

At block 1352, health evaluation system 40 (shown in FIG. 3) initially captures the static thermal image (human thermal image). Health evaluation system 40 then analyzes general anatomic zones (chest, upper abdomen, lower abdomen arms, legs, head, and so on) within the patient's body. Some general anatomic zones are naturally hotter or cooler than others. If the average temperature data of the pixels for an anatomic zone in a thermal image is higher than the average temperature data of the pixels for another anatomic zone that is naturally hotter, there is an abnormality. For example, the head is the hottest anatomic zone, and the chest and feet are some of the coolest zones. If the chest or feet zone is hotter than the head zone, then the chest or feet zones are exhibiting abnormalities.

If an abnormality is detected, health evaluation system 40 (shown in FIG. 3) analyzes the organs within the general anatomic zone containing the abnormality at block 1356. Organs also naturally exhibit hotter or cooler temperatures relative to the other organs within the general anatomic zone. This is because each organ in a general anatomic zone is composed of a different type of cell, each with different pathological functions. The different pathological functions result in each cell type producing a different amount of heat output. Within that general anatomic zone, system 40 compares and analyzes the organs and if an organ is exhibiting abnormal temperatures, system 40 focuses on that particular organ. Each organ is pre-divided into specific zones such as shown in FIGS. 17A, 17B, 18, 19A, 19B, and 19C, and the temperatures of each zone are compared against the average overall temperature of the entire organ. If there is a temperature variation ($\Delta T$) greater than zero, there is potentially an abnormality. If an abnormality is detected, then system 40 performs a thermal depth analysis at block 1358 to determine whether the abnormality is at the surface of the body or below the surface of the body. If the abnormality is at the surface of the body, a skin abnormality is indicated and not an organ abnormality. If the abnormality is below the surface of the body, the organ has the abnormality, which requires further clinical evaluation.

FIGS. 37A and 37B illustrate thermal images 1400A and 1400B of a healthy woman. The heat mappings in the image breast area in images 1400A and 1400B and the heat wrapping in the abdomen area of 1400B demonstrate that the heat distribution of the woman is symmetric, which indicates that there are no apparent abnormalities.

FIG. 38A illustrates a representation of a vectorized thermal image 1410. Vectorized thermal image 1410 is a conventional thermal image that has been vectorized to remove the background image, as described above and shown in FIGS. 13A-13C. On the other hand, FIG. 38B illustrates a representation of an analyzed thermal image 1415 produced by health evaluation system 40 (shown in FIG. 3) after analyzing vectorized thermal image 1410 during the auto-analysis block 20 of FIG. 2. Both images are representative of a patient's whole body. The body is in a position facing towards the camera with the patient's arms at the side. Analyzed thermal image 1415 graphically illustrates problem or suspect areas 1416, 1417, and 1418 identified by health evaluation system 40 as having abnormal temperatures. Abnormal temperatures are generally indicative of a health problem. Health evaluation system 40 performs the auto-analysis at block 20 (shown in FIG. 2) by using a depth algorithm.

FIG. 39A illustrates a representation of a vectorized thermal image 1420. Vectorized thermal image 1420 is a conventional thermal image that has been vectorized to remove the background image, as described above and shown in FIGS. 13A-13C. On the other hand, FIG. 39B illustrates a representation of an analyzed thermal image 1425 produced by health evaluation system 40 (shown in FIG. 3) after analyzing the vectorized thermal image 1420 during the auto-analysis block 20 of FIG. 2. Images 39A and 39B are images of the back of the patient's body. The images of the back allow portions of the body, not visible by viewing the front of the patient, to be analyzed.

FIGS. 40A, 40B, and 40C illustrate a representation of sectional views from the cascade chromatography process. In FIGS. 40A-40C, sectional view images 1430A, 1430B, and 1430C are generated from the cascade chromatography process (FIG. 10) where the pixel color is assigned either black or white. Sectional view images 1430A begin with a captured thermal image in row R1, column C1, which are views of the front whole body. The sectional view images are in order from left to right and then top to bottom. Row R1, column C1, contains the first image, while Row R1, column C2, contains the second image, and so forth. FIG. 40B depicts the continued pixel color change in sectional view images 1430B for rows R1, R2, and R3. As can be seen from one image of the series to the next adjacent image, some of the pixels are turned white or black. FIG. 40C depicts the continued pixel color change in images 1430C for rows R1, R2, and R3. The progression of individual sectional view images demonstrates the active change at each step of the cascade chromatography process, and therefore these images are known as dynamic thermal images.

In this embodiment, there are three rows in FIGS. 40A, 40B, and 40C. However, more or less rows and columns may be utilized. Each row has a series of eight sectional view images. Sectional view images 1430A are progressive modifications of the images according to the flowchart of FIG. 10. Health evaluation system 40 (shown in FIG. 3) records the temperature of each pixel in one image respectively, and organizes the pixels by highest to lowest temperature into a list of pixels. Health evaluation system 40 then compares each pixel to the corresponding pre-programmed anatomical position. If the pixel is at a normal temperature, the pixel color is changed to white. Otherwise, the pixel is left unaltered or changed to a non-white pixel (for example, the color black). The next pixel in the list of pixels is then compared. This continues until the list of pixels is exhausted.

Figures 41A, 41B:
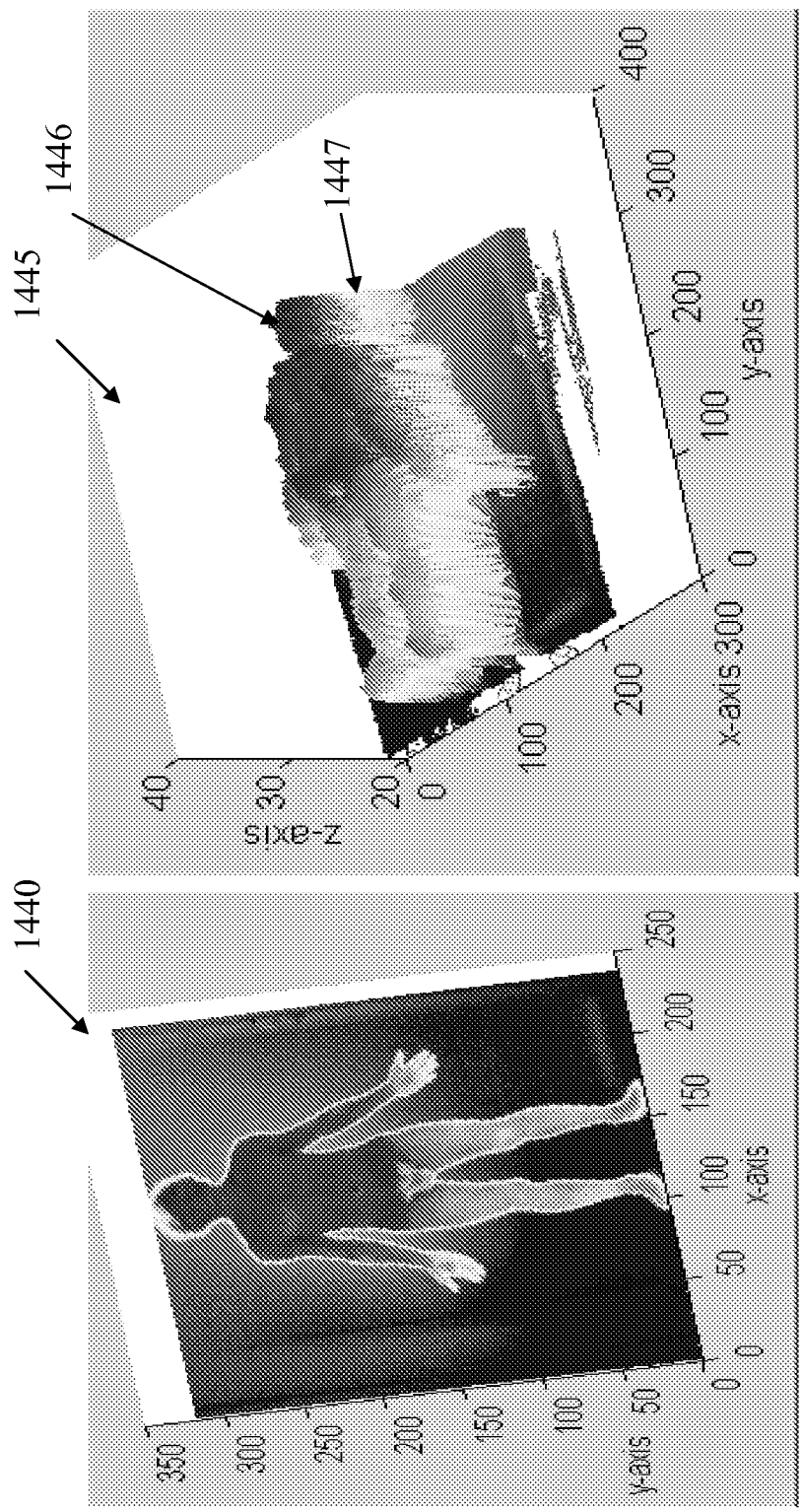
FIG. 41A illustrates a representation of a normal thermal image in two-dimensions.
FIG. 41B illustrates a representation of a three-dimensional analyzed thermal image created from the thermal image of FIG. 41A.

FIG. 41A illustrates a representation of a normal thermal image 1440 in two-dimensions. The term normal in this context is used to denote a non-vectorized thermal image. FIG. 41B illustrates a representation of a three-dimensional analyzed thermal image 1445 created from thermal image 1440 (shown in FIG. 41A). Image 1445 is created during the auto-analysis block 20 (shown in FIG. 2). Image 1445 demonstrates the three-dimensional computations that health evaluation system 40 (shown in FIG. 3) undergoes when analyzing a thermal image. Thermal image 1440 is placed upon an x and y-axis. Image 1440 is then analyzed in three-dimensions for abnormalities as depicted in image 1445. Image 1445 is a representation of the heat output by a patient's body, where each x and y-axis intersection point represents a position in a patient's body. The z-axis represents the temperature at a given depth within the patient's body. Note that at a higher z-axis point 1446 the color is darker, signifying a cooler temperature, and at a lower z-axis point 1447 the colors grow lighter, indicating a warmer temperature. This serves to demonstrate increasing temperature when moving from the surface of the body to the inside of the body. Calculations of the body temperature are performed using three-dimensional mathematical formulae. Additionally, as a consequence of viewing the heat output in three dimensions, the contours of the body are discernable in image 1445.

Figures 42A, 42B:
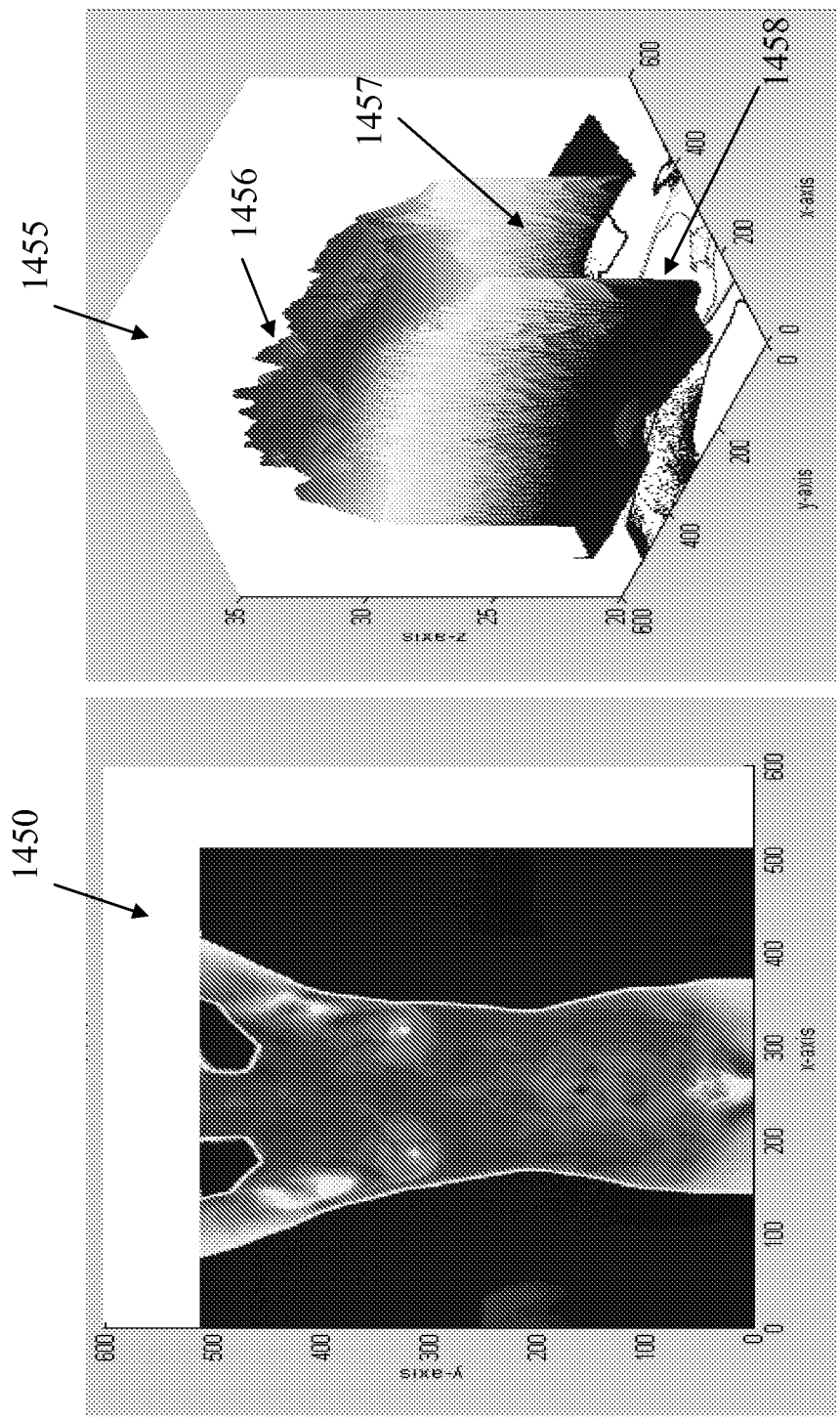
FIG. 42A illustrates a representation of a vectorized thermal image in two-dimensions.
FIG. 42B illustrates a representation of a three-dimensional analyzed thermal image created from the vectorized thermal image of FIG. 42A.

FIG. 42A illustrates a representation of a vectorized thermal image 1450 in two-dimensions. FIG. 42B illustrates a representation of image 1455 created from vectorized thermal image 1450 (shown in FIG. 42A). Image 1455 is created by health evaluation system 40 during the auto-analysis block 20 (shown in FIG. 2). Vectorized thermal image 1450 depicts a thermal scan (captured thermal image) of the chest and abdomen area of a patient. Image 1455 (shown in FIG. 42B) is a three-dimensional section of only the abdomen instead of the chest and abdomen (shown in FIG. 42A). The three-dimensional section of the abdomen demonstrates a more detailed view of the various temperatures at different depths 1456 and 1457 within the patient's abdomen. A black area 1458 indicates a depth at which no thermal readings were recorded.

Figures 43A, 43B:
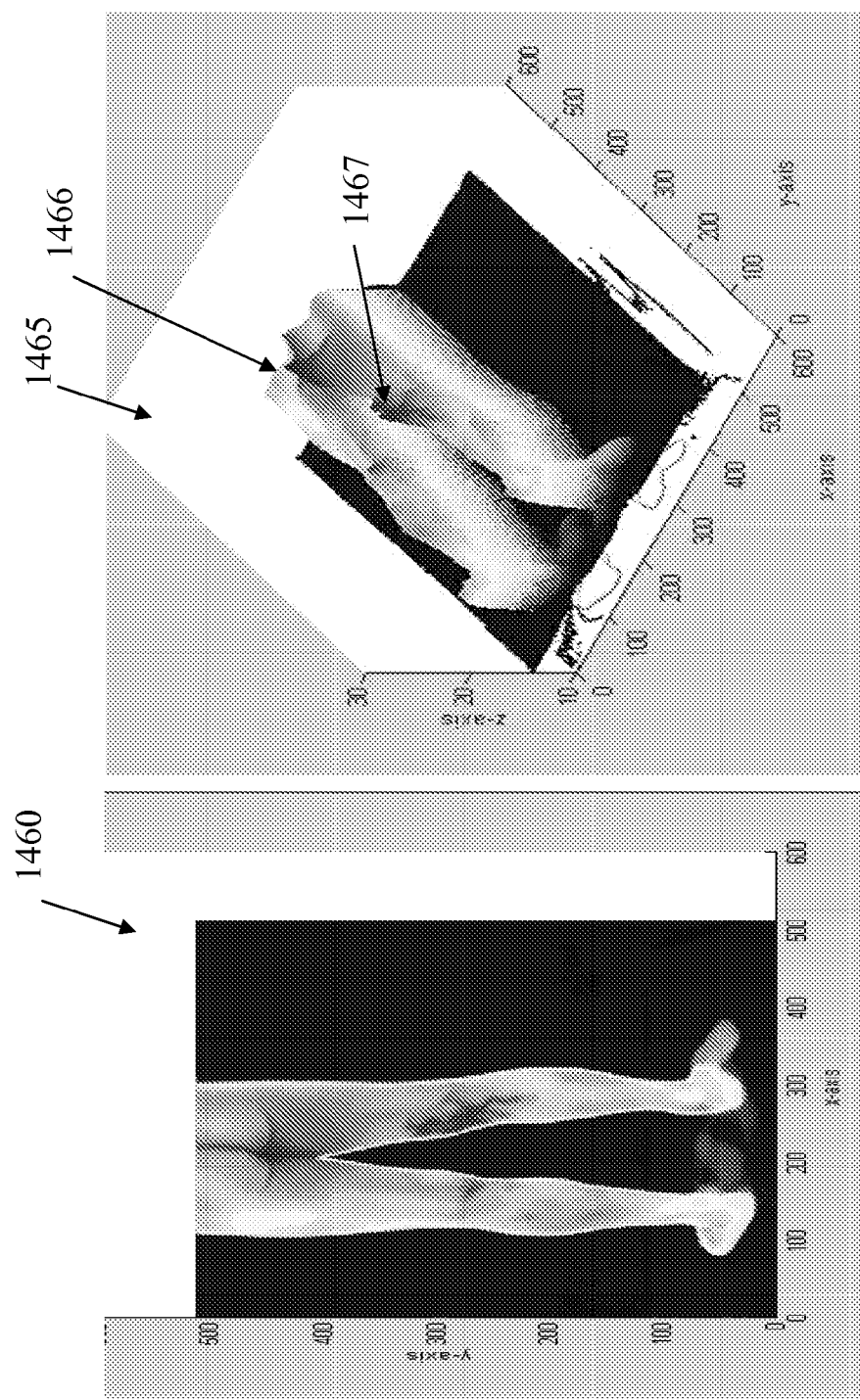
FIG. 43A illustrates a representation of a vectorized thermal image in two-dimensions.
FIG. 43B illustrates a representation of a three-dimensional analyzed thermal image created from the vectorized thermal image of FIG. 43A.

FIG. 43A illustrates a representation of a vectorized thermal image 1460 in two-dimensions. FIG. 43B illustrates a representation of a three-dimensional analyzed thermal image 1465 created from vectorized thermal image 1460 (shown in FIG. 43A). Image 1465 is created by health evaluation system 40 during the auto-analysis block at 20 (shown in FIG. 2). Image 1465 is created in a similar manner as described above in relation to FIG. 41B. Image 1460 depicts a back view of the lower half of a patient's body. The patient's right leg has a large black area 1467 (shown in FIG. 43B). Large black area 1467 appears in both FIGS. 43A and 43B and is darker than the surrounding leg area, indicating a temperature difference that health evaluation system 40 (shown in FIG. 3) identifies as abnormal. Health evaluation system 40 then analyzes large black area 1467 to determine whether or not the area is injured using change in temperature ($\Delta T$) calculations. In FIG. 43B, the depth of large black area 1467 or area 1466 (represented by black peaks) is mapped in the z-axis, which helps determine the depth. When performing depth analysis, health evaluation system 40 (shown in FIG. 3) generates a three-dimensional analyzed thermal image from either a two-dimensional normal thermal image or vectorized thermal image.

FIGS. 22-29 are examples of the GUI to enable the user to customize and create scans. FIG. 30 illustrates one embodiment of a patient report printout 1000. The GUIs described below contain a database of patient files with numerous information fields. Through these options, the user can create new patient files, edit patient files, take IR thermal images of patients, analyze the thermal images, and print a report of the analysis by activating a corresponding GUI described below, which is overlaid upon the main GUI.

Figure 22:
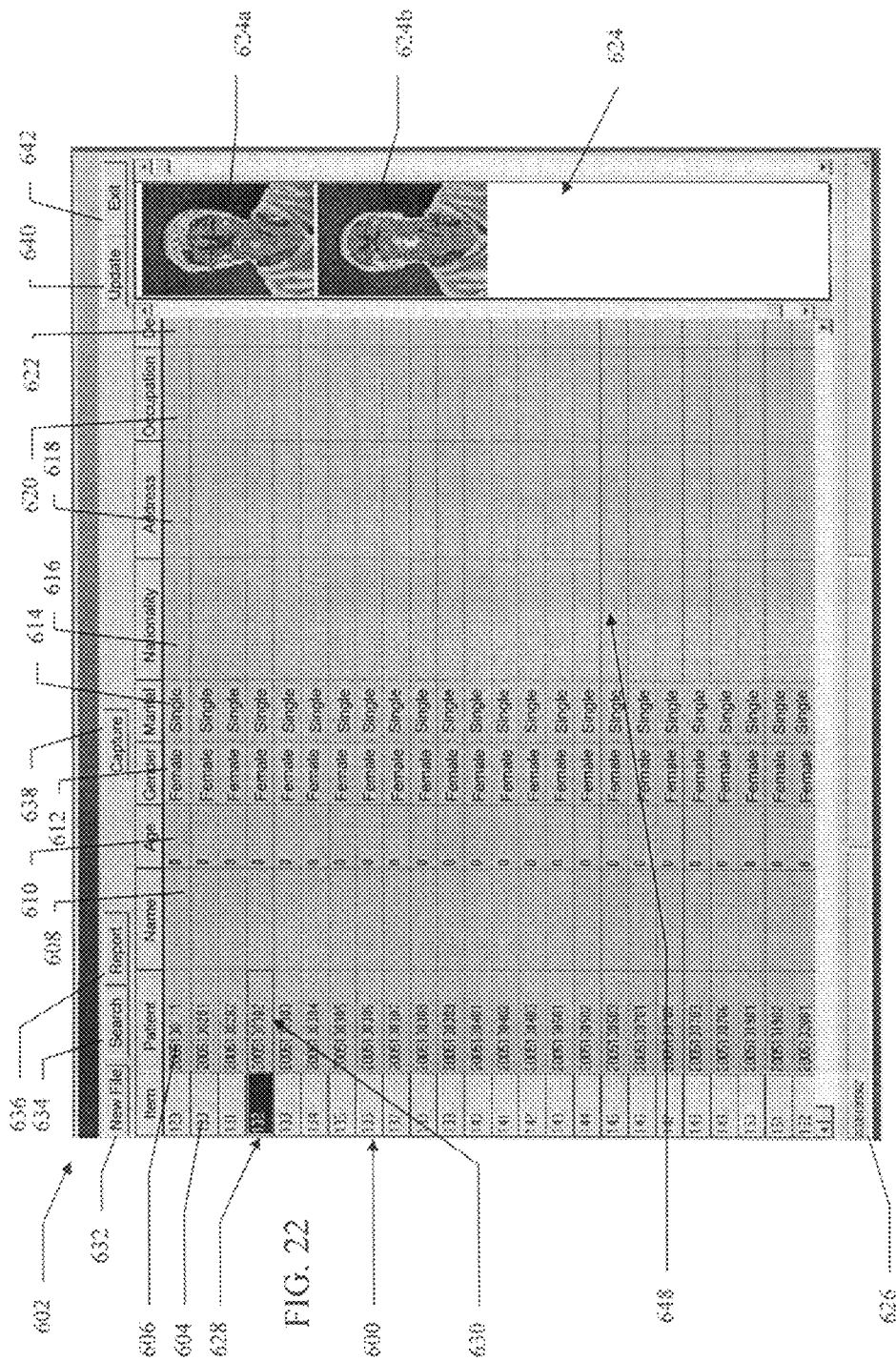
FIG. 22 illustrates one embodiment of a main patient database graphical user interface (GUI)

In one embodiment, there are two methods of retrieving the patient file editing GUI, either by right clicking a patient file and selecting the third drop down option (FIG. 24), or by clicking an edit button in the main GUI (FIG. 22).

The software enables a user to remotely take photographs of a patient with an infrared (IR) camera. The GUIs provides the user an automatic determination of the colors of a thermal image and automatic analysis of the thermal image to detect abnormalities.

FIGS. 23 through 29 are overlaid on a depiction of the main GUI (FIG. 22).

FIG. 22 illustrates one embodiment of a main patient database GUI 602 depicting a patient file 600 within one embodiment of a database 648. File 600 contains a database item number 604 corresponding to the position of file 600 within the database. File 600 also contains a patient serial number 606, a patient's name 608, a patient's age 610, a patient's gender 612, a patient's marital status 614, a nationality of the patient 616, a patient's address 618, a patient's occupation 620, and a patient's description 622. File 600 also contains a set of thermal images of a patient undergoing evaluation. In one embodiment, the thermal images in file 600 are displayed in an area 624 as depicted in thermal images 624*a* and 624*b*. The user can select a particular patient file (highlighted number 132) 628 by clicking on fields 604 through 622. Clicking on fields 606, 608, 610, 612, 614, 616, 618, 620, and 622 highlights a database item number 604 as depicted in a selected item number 628, and selects a field as depicted in a selected field 630.

Figure 23:
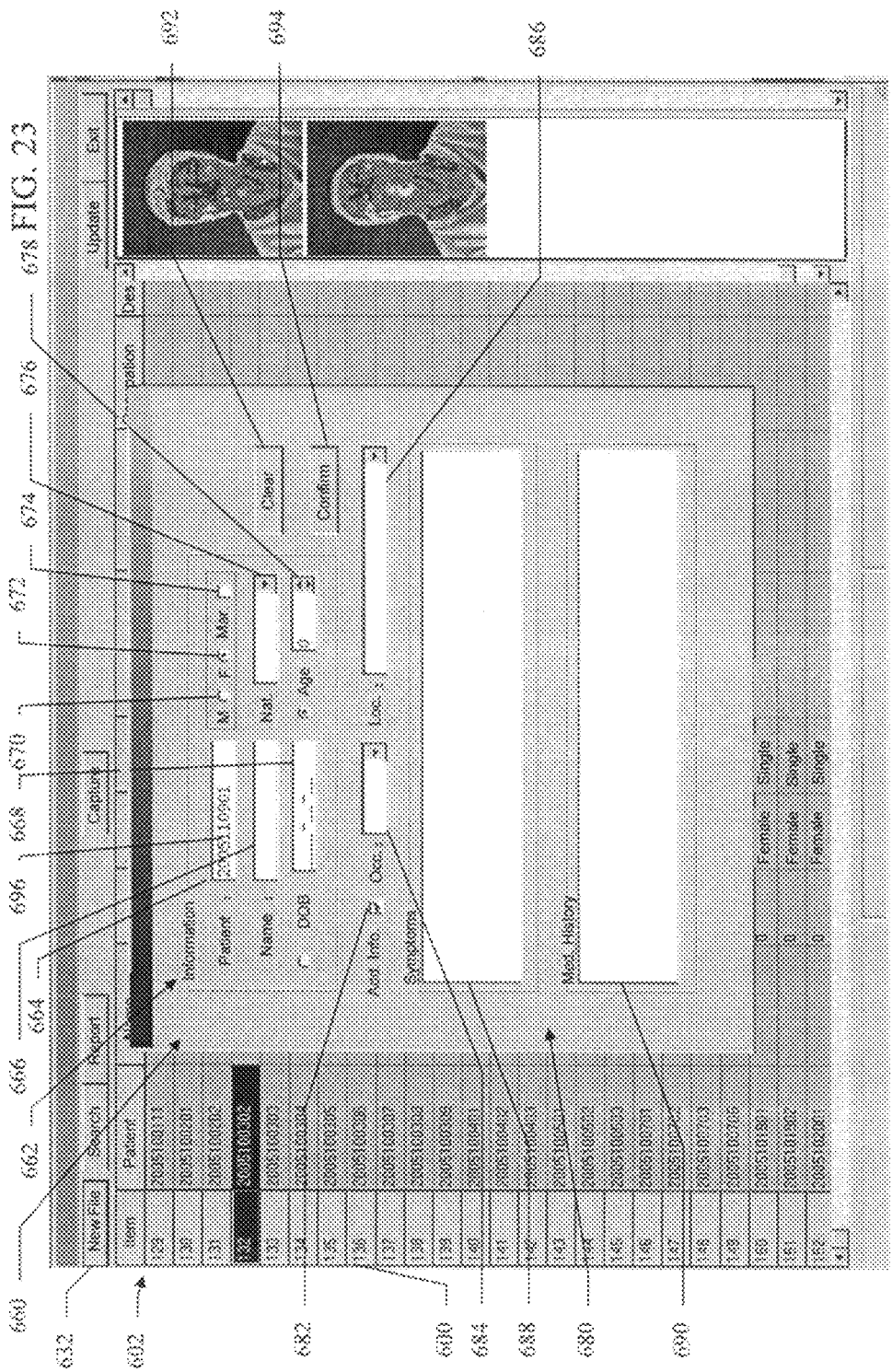
FIG. 23 illustrates an embodiment of a new patient file creation GUI.
Figure 24:
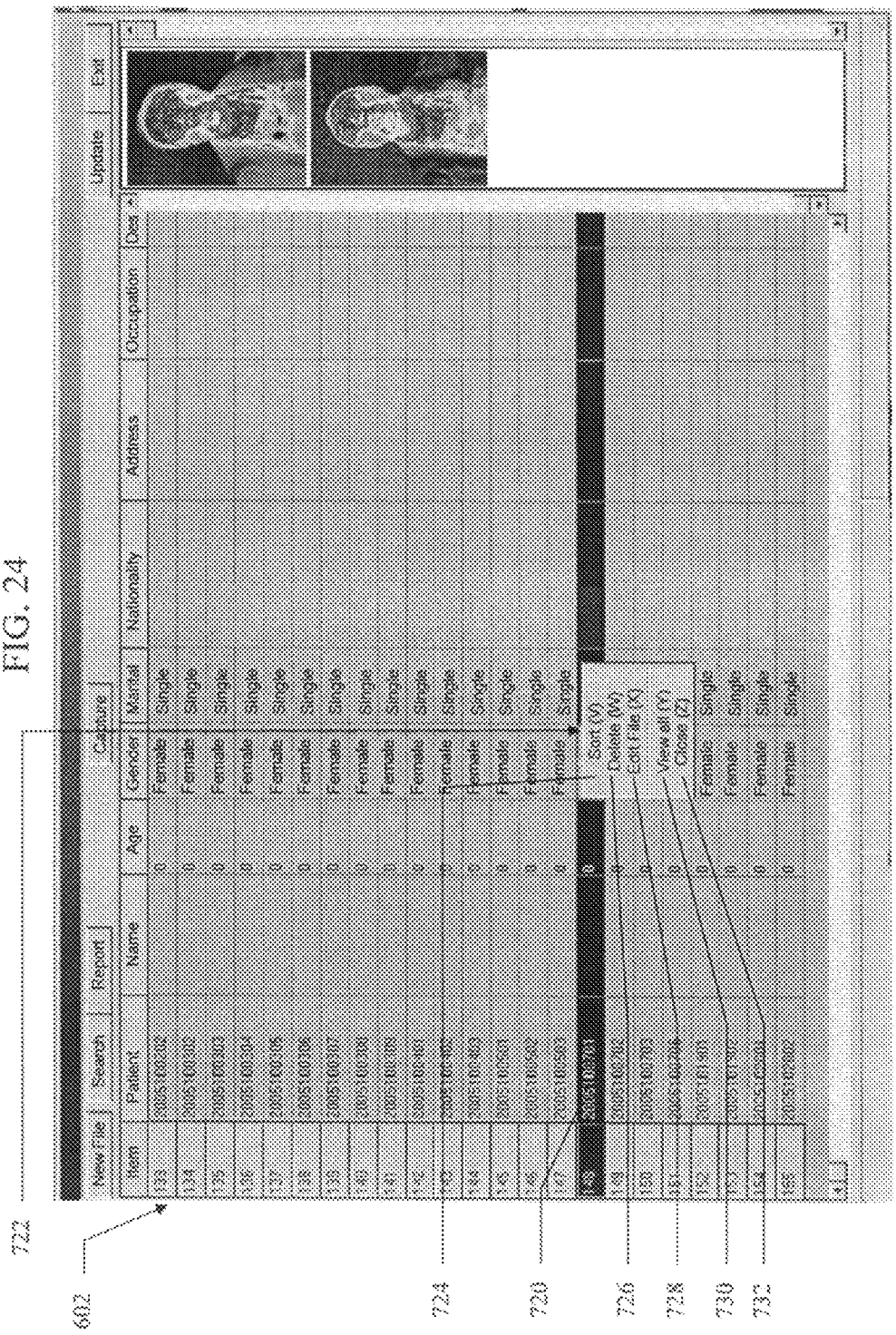
FIG. 24 illustrates an embodiment of a new patient file sub-menu.

Clicking on database item number 604 selects the entire line, as depicted in an entire patient line selection 720 (shown in FIG. 24). Clicking on a field does not otherwise perform any action because database 648 is read-only. When file 600 is selected, patient serial number 606 is displayed in the lower left hand corner of the screen 626 and thermal images in area 624 are updated to correspond to data that is stored in file 600. With or without selecting file 600, a user can create another patient file by left-clicking a new patient file button 632, which opens a patient file creation GUI as depicted in one embodiment of a new patient file creation GUI 660 (shown in FIG. 23). In addition, with or without selecting file 600, a user can left-click an update patient file button 640 which updates database 648 with any changes that were made. Moreover, with or without selecting a file 600, a user can left-click an exit button 642 which exits main patient database GUI 602. After selecting file 600, a user can left-click a patient file search button 634, a patient report button 636, or an IR image taking button 638. Without first selecting file 600, buttons 634 through 638 are inoperable.

Figure 25:
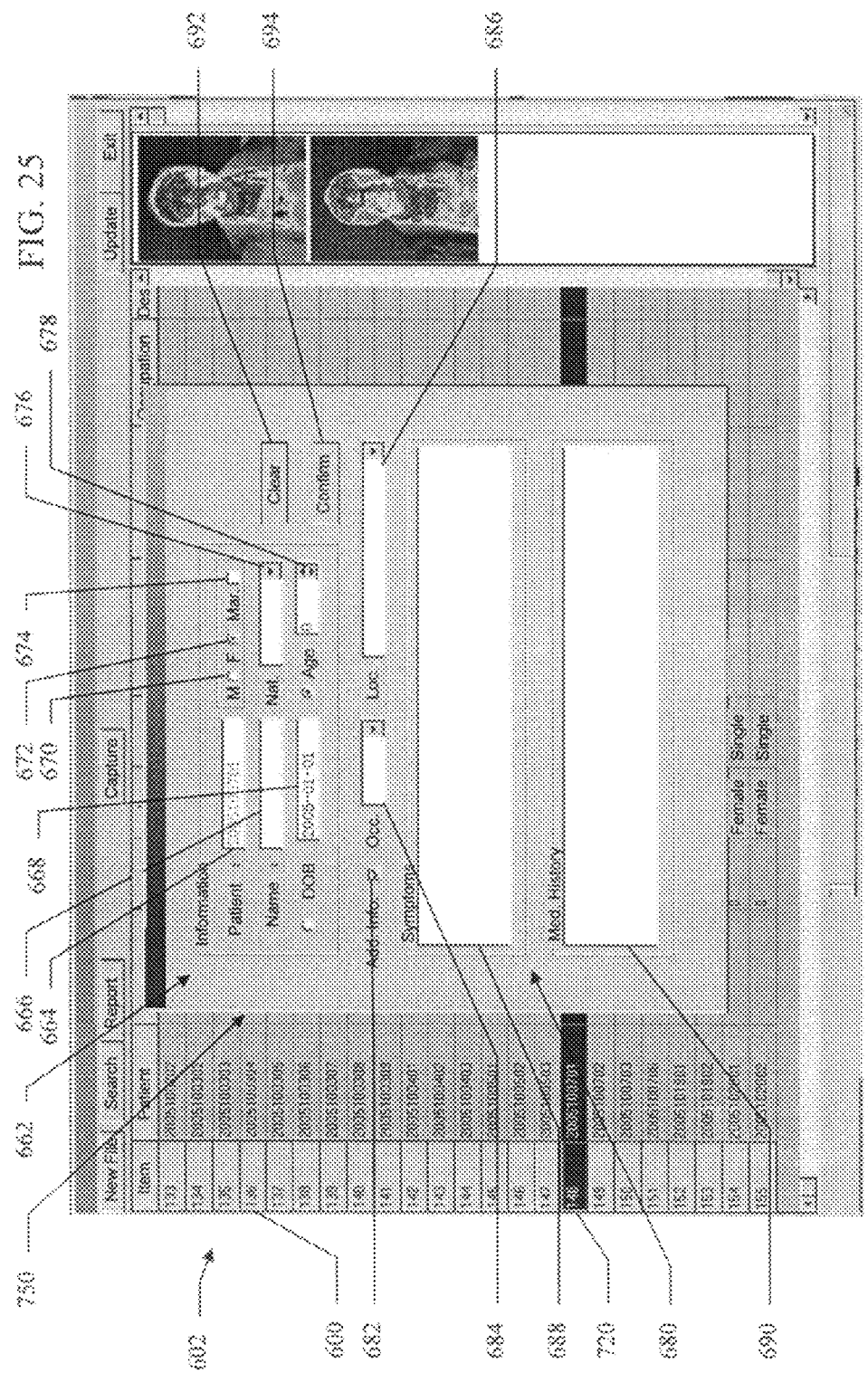
FIG. 25 illustrates an embodiment of patient file editing GUI.
Figure 26:
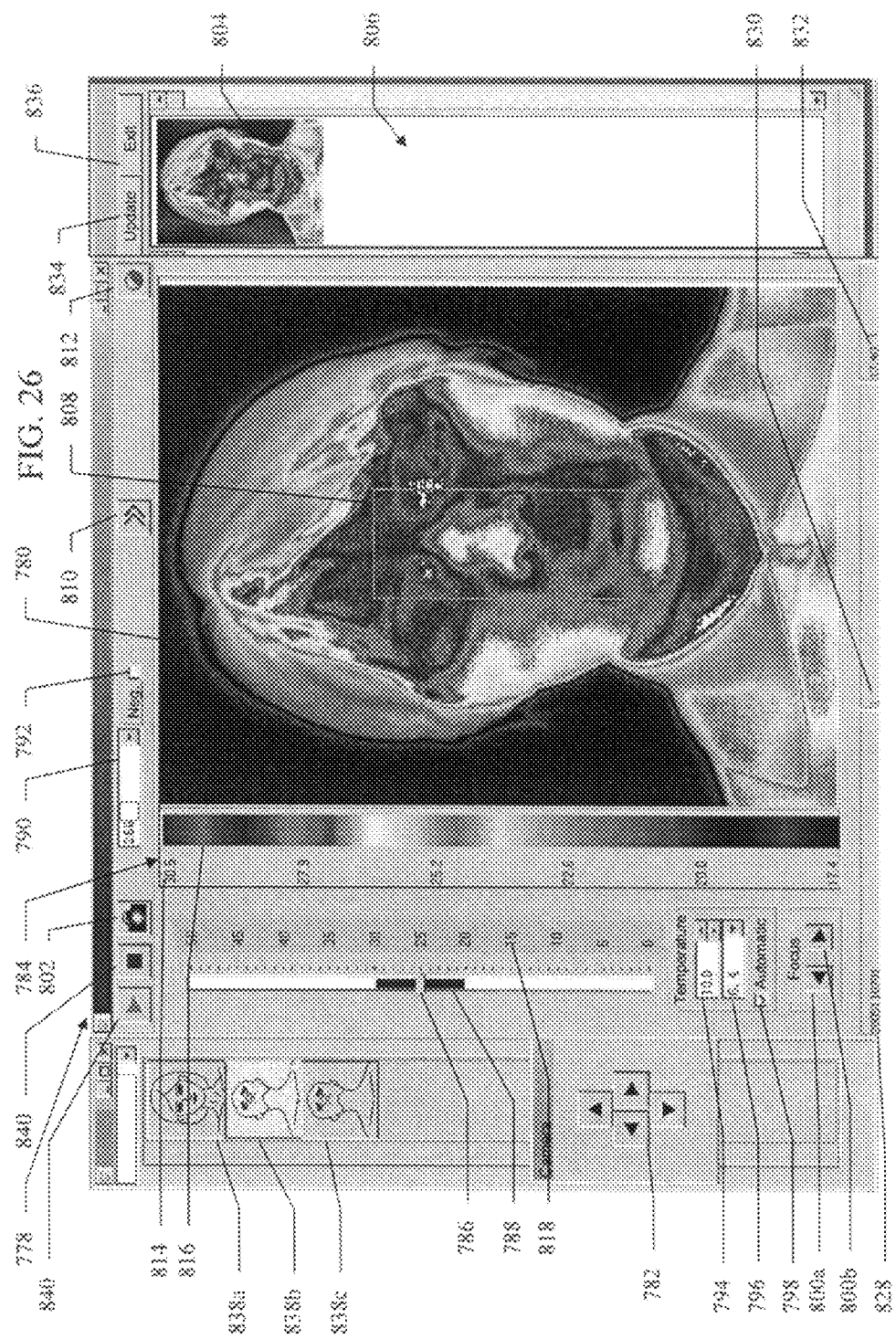
FIG. 26 illustrates an embodiment of an IR thermal image capture GUI.

Once file 600 is selected, a user can left-click button 634 to edit file 600, which opens a patient file GUI that is editable as depicted in one embodiment of a patient file GUI 750 (shown in FIG. 25). In addition, once file 600 is selected, a user can right-click on GUI 602, which opens a menu as depicted in one embodiment of a new patient file sub-menu 722 (shown in FIG. 24). Furthermore, once file 600 is selected, a user can left-click the patient report button 636 to view a preview of a patient report, which opens a patient report preview GUI as depicted in one embodiment of a thermal image analysis GUI 890 (shown in FIG. 28). Moreover, once file 600 is selected, a user can also left-click the IR image capture button 638 to add thermal images to file 600, which displays a thermal image capture GUI as depicted in FIG. 26. In one embodiment, when any of GUI buttons 632, 634, 636, and 638 are left-clicked the resulting displayed GUI is overlaid upon GUI 602.

FIG. 23 illustrates one embodiment of a new patient file creation GUI 660. GUI 660 creates new file 600 and stores the information in database 648. GUI 660 appears when button 632 is selected, regardless of whether file 600 is selected. GUI 660 appears overlaid upon GUI 602 (shown in FIG. 22). GUI 660 contains both a basic information area 662 and an additional information area 680. All information for both areas 662 and 680 is manually entered by the user. Area 662 contains a patient serial number field 664, a name field 666, a date of birth field 668, a male radio button 670, a female radio button 672, a marital status checkbox 674, a nationality field 676 and an age field 678. Clicking serial number field 664 allows a user to enter the serial number of the patient. In addition, clicking name field 666 allows a user to enter the name of the patient. Moreover, clicking a date of birth field 668 allows a user to enter the date of birth of the patient. In one embodiment of the date of birth field, the date of birth is entered as the year followed by the month and then the day. The user can select either a male or female gender by selecting either field 670 or field 672.

To indicate whether a patient is married, a user can left-click a marital status checkbox 674. Clicking checkbox 674 indicates that the patient is married. Furthermore, left-clicking nationality field 676 displays a drop down menu with a list of preset nationalities. Left-clicking one of the nationalities in the list enters the selection into field 676. Clicking age field 678 allows a user to enter the age of the patient. Moreover, left-clicking on the arrows in field 678 either increases or decreases the number in field 678 by 1. Additional information area 680 contains an additional information checkbox 682, an occupation field 684, a location field 686, a patient symptoms field 688, and a patient medical history field 690. To enter additional information beyond the basic information, a user selects checkbox 682 by left-clicking it whereby field 684 displays a preset list of occupations. Left-clicking one of the occupations in the list enters the selection into field 684. Additionally, left-clicking field 686 displays a preset list of locations. Left-clicking one of the locations in the list enters the selection into field 686. Additionally, selecting field 688 allows the user to enter information about the patient's symptoms. Moreover, selecting patient field 690 allows the user to enter relevant medical history information. A clear button 692 allows the user to clear all entries. Once the user is finished entering patient information, the user left-clicks a confirm button 694, which confirms the data, closes GUI 660, and saves the entered information into file 600 in database 648. The user then returns to GUI 602 (shown in FIG. 22).

FIG. 24 illustrates an embodiment of a new patient file sub-menu 722 overlaid on GUI 602 (shown in FIG. 22). Sub-menu 722 allows a user to select from several operations to be performed on a list of file 600 or a single file 600. Sub-menu 722 appears when a user right-clicks any file 600. Sub-menu 722 contains a patient file sort option 724, a delete file option 726, and an edit file option 728. When a user left-clicks option 724, the list of file 600 is sorted according to patients' serial numbers. In one embodiment, files 600 are sorted in ascending order. When a user left-clicks option 726, the information within selected field 630, within the file 600, is deleted. When a user left-clicks option 728, GUI 750 (shown in FIG. 25) is displayed.

Another embodiment of sub-menu 722 contains additional options depicted by a view all option 730 and a close all option 732. When selected, option 730 displays all records for the patient at once. When selected, option 732 closes all records opened by option 730.

FIG. 25 illustrates one embodiment of GUI 750. GUI 750 allows a user to edit file 600. GUI 750 is another embodiment of GUI 660 (shown in FIG. 23), with certain limitations. Fields 662 through 690 in GUI 750 are similar to those of GUI 660, with the exception of patient serial number field 664. In order to prevent inadvertent deletion of a patient file, patient serial number 664 in GUI 750 is read-only, and therefore cannot be changed from the originally assigned number.

FIG. 26 illustrates an embodiment of an IR thermal image capture GUI 778. GUI 778 allows the user to capture thermal images of a patient. GUI 778 is connected to an IR camera. The IR camera transmits a thermal image 780 to GUI 778. The IR camera can be operated remotely by camera movement buttons 782. Buttons 782 operate the camera in the up, down, left, and right directions when the corresponding arrow is left-clicked. The IR camera moves along a plane, remaining parallel to the patient. The user utilizes camera focus buttons 800*a* and 800*b* to focus the IR camera. A thermal image color scheme area 784 is composed of a Celsius temperature scale 814 and a thermal color scale 816. The colors in scale 816 correspond to the temperature values in Celsius temperature scale 814. In one embodiment, scale 816 is composed of the color black representing the lowest temperature on scale 814, changing to the color white at the highest temperature on scale 814. In one embodiment, two methods of changing thermal image color scheme 784, manually and automatically, are utilized.

One embodiment of a method for manually changing the color scheme for thermal image 780 is depicted by a temperature setting arrow 786. Scale 814 can be modified by a sliding arrow 786 up and down a Celsius temperature scale 818. The upper and lower limits relative to arrow 786 are displayed by a temperature limit bar 788. Bar 788 displays the range of temperatures, relative to arrow 786, which appear in area 784. Bar 788 can be modified by changing the value in a temperature range field 794. Clicking on a field 794 allows a user to enter information into the field. Additionally, clicking on the buttons in field 794 correspondingly increases or decreases the displayed range value in field 794. A user can also modify the rate at which the colors change in scale 816 by changing the value in a thermal color rate change field 796. Left-clicking on field 796 displays a drop-down list of preset rate change values. Left-clicking on one of the preset rate change values changes the rate of change of colors in scale 816. Thermal image color scheme 784 can be changed by clicking a color preset field 790. Field 790 contains a set of 256 colors for use in thermal image 780. A different preset is selected according to the thermal imaging standards of various countries.

Another embodiment of a thermal image color scheme utilizes computer generated algorithms to automatically determine the proper temperature color settings. Manually adjusting color temperature scheme 784 is a cumbersome and inexact process. To determine the color scheme automatically, a user activates the automatic color selection feature by left-clicking an automatic temperature measurement checkbox 798. By left-clicking checkbox 798, arrow 786, field 794, and field 796 are disabled. The user cannot edit or input information using these fields or arrows.

Clicking a thermal image negative checkbox 792 causes a negative of a camera image to appear in GUI 778 instead of thermal image 780. Clicking checkbox 792 again returns the camera image to the image's non-negative state. To begin the thermal imaging process, the user clicks an image capturing button 802. Once button 802 is pressed, an IR camera captures a series of thermal images, which are viewable as smaller preview thermal images 804 in a thermal image preview area 806. A user clicks image advancement button 810 to change thermal image 780 to the next captured thermal image. Once a user decides to pick a particular image, the user can left-click a save button 834. When button 834 is left-clicked, GUI 778 closes and a thermal image preview/save GUI 860 opens.

In one embodiment of an automatic method of capturing IR thermal images, depicted by GUI 778, the patient's eyes, nose, and mouth must be within a camera alignment rectangle 808. GUI 778 automatically creates a thermal zone based on the position of the patient's eyes, nose, and mouth in rectangle 808. The infrared image is processed into mathematical data such that the image can be compared against a standard template and mapped into zones. To accomplish this, the thermal image is vectorized. Once the image is vectorized, an algorithm determines the location of characteristic reference points. These characteristic reference points are based on the position of the eyes, nose, and mouth of the patient that are within rectangle 808. Once the characteristic reference points are found, GUI 602 (shown in FIG. 22) retrieves a standard zoning template corresponding to the position code of the infrared image. GUI 602 scales the standard template zones to match the infrared image using the characteristic reference points. Once the standard template zones are matched, GUI 602 divides the infrared image into mapped zones. Such mapped zones represent key interest areas for which thermal data may be interpreted and analyzed.

In an embodiment of a manual method of capturing IR thermal images, depicted by GUI 778, patient position icons 838*a*, 838*b*, and 838*c* are used instead of an automatic zoning system. When icon 838*a* is clicked, thermal image 780 is stored in file 600 under icon 838*a*. When icon 838*b* is clicked, thermal image 780 is stored in file 600 under icon 838*b*. When icon 838*c* is clicked, thermal image 780 is stored in file 600 under icon 838*c*.

The user can exit GUI 778 by clicking an exit button 836 or a stop button 840. Clicking button 836 closes GUI 778 and opens GUI 860. Before GUI 860 is opened, thermal image 780 is vectorized and the background image is removed. Removing the background enables GUI 890 to analyze thermal image 780. Stop button 840 performs similarly to exit button 836. A circle button 812 enables the user to change the contrast of the picture. A play button 840 captures thermal image 780. The patient's serial number 828 is displayed in the lower left hand corner of GUI 778. The position of thermal image 780 in relation to the total set of thermal images for the patient is displayed as a thermal image position number 830. A lower and upper temperature limit 832 is displayed in the lower right hand corner of GUI 778.

Figure 27:
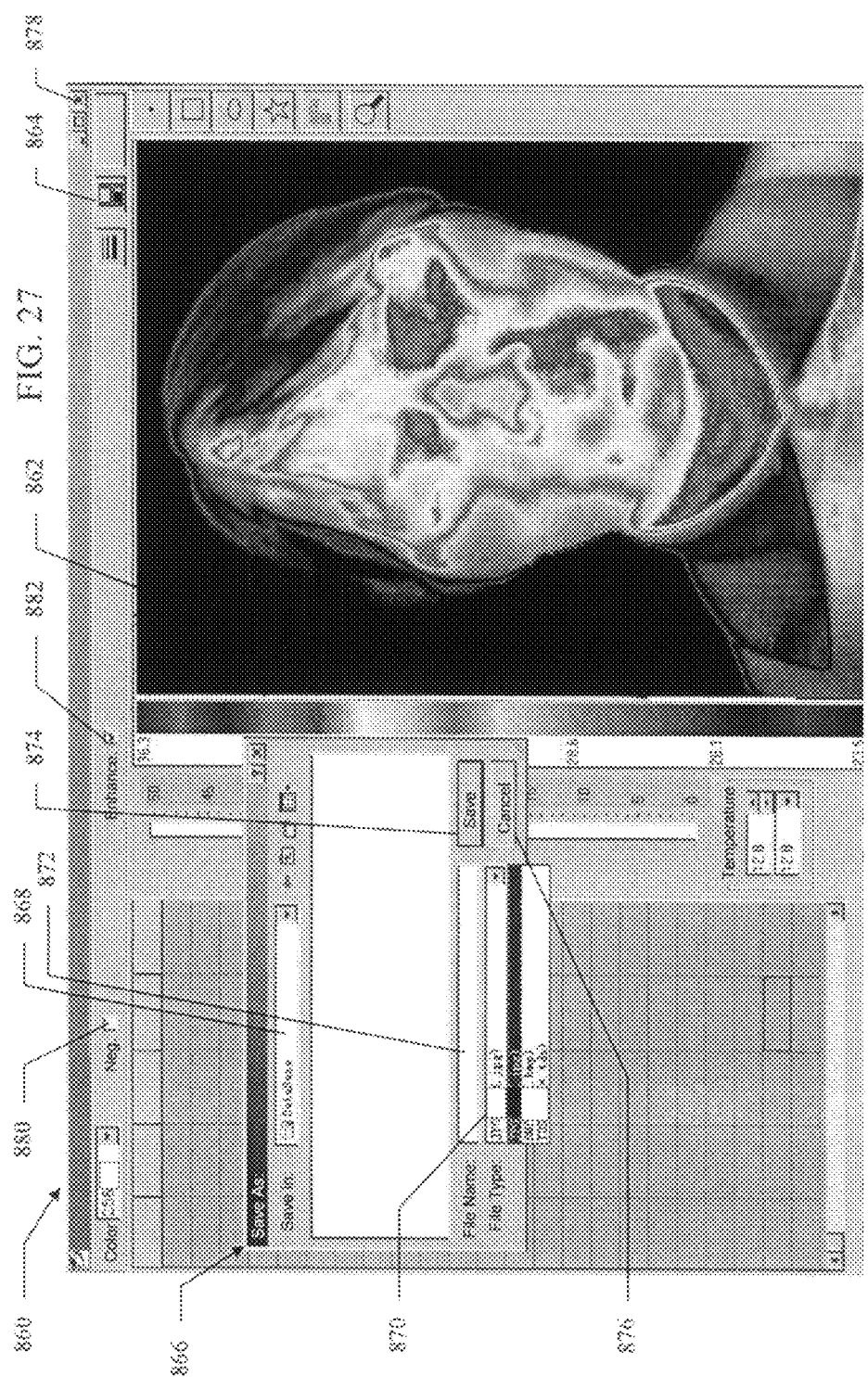
FIG. 27 illustrates an embodiment of thermal image preview and save GUI.

FIG. 27 illustrates an embodiment of GUI 860. GUI 860 displays a vectorized thermal image 862, a thermal image save prompt 866, and a save button 864.

In one embodiment, image 862 can be saved by utilizing prompt 866 to a selected folder 868 within a storage device. Left-clicking button 864 displays prompt 866. Image 862 can be saved as a .jpg, .bmp, or .tds file using file type field 870 with a user-defined file name 872. A user can left-click button 874 to save image 862 that uses file type 870 and user-defined file name 872. A user can left-click a cancel button 876 to abort the save procedure. GUI 860 also contains a thermal image negative checkbox 880, which performs similarly to checkbox 792 (shown in FIG. 26). Furthermore, GUI 860 contains a thermal image enhancement checkbox 882. Left-clicking checkbox 882 enhances the resolution of image 862 by smoothing out any rough edges. Left-clicking checkbox 882 again undoes the process. Left-clicking a close button 878 closes GUI 860 and then opens GUI 602 (shown in FIG. 22).

FIG. 28 illustrates an embodiment of GUI 890. GUI 890 includes an abnormality analysis area 902, a TMT analysis area 926, and a patient notes area 928. TMT analysis area 926 contains a forehead region condition field 892, an eye region condition 894, a nose region condition 896, a mouth region condition 898, and a thorax region condition 900. Each of the fields 892 through 900 contains either a (+) or a (−) indicating whether a person's temperature in the region is abnormal or not. In one embodiment, a (−) indicates a normal condition, while a (+) indicates an abnormal condition. Based on the values indicated in fields 892 through 900, health evaluation system 40 performs an analysis and identifies if the patient has an abnormal upper respiratory condition, and if so, what is the specific condition of the patient. The system generates and displays the output in area 902. Area 928 contains the average temperature of the patient's upper respiratory system 904, condition of a location of the patient 906, whole body condition of the patient 908, physical appearance of the patient's body 910, and an epidemiology report 912. Average temperature 904 is the average temperature of the patient based on the thermal images in file 600. Information in fields 906 through 912 is entered by a user. Condition of a location of the patient 906 describes whether a particular region of the patient's body has abnormalities based on thermal analysis. Whole body condition of the patient 908 describes whether the patient's body as a whole has abnormalities based on thermal analysis. Physical appearance of the patient's body 910 describes any physical symptoms the patient exhibits (for example, rashes, lesions, bloating, or being overweight). Epidemiology report 912 describes where the patient has been, who has come into contact with the patient, and other medical history of the patient. When a user is finished entering information, the user can click a save button 914. Clicking button 914 saves the information displayed into file 600. For a user to enter comments into fields 906 through 912, the user must click a comments button 916. Clicking button 916 opens up a new interface where comments can be entered into the fields for 906 through 912. When the new interface is closed, the comments are saved and displayed in fields 906 through 912. The information entered is later displayed in a patient report comments field 956 (shown in FIG. 29). Clicking a visual report tab 920 displays a patient report preview GUI 950 (shown in FIG. 29). Clicking a close button 930 closes GUI 890 and opens GUI 602 (shown in FIG. 22).

One embodiment of a thermal analysis chart 922*a* is displayed in GUI 890. Chart 922*a* plots the patient's temperature in Celsius 922*b* against the metabolic energy output of the patient 922*c* for each body region reported in TMT analysis area 926.

FIG. 29 illustrates an embodiment of GUI 950. GUI 950 is automatically displayed in the event that GUI 890 (shown in FIG. 28) is closed. GUI 950 allows a user to preview a patient report 952 before printing. One embodiment of thermal images for patient report 952, which are retrieved from file 600 (shown in FIG. 22), are depicted by thermal images 954*a* and 954*b*. In addition, patient report 952 includes a field 956, which contains information from fields 906 through 912 (shown in FIG. 28). Field 956 also contains information on any abnormal readings detected by the system, in addition to a description of each body region analyzed and abnormalities, if any, in each body region. Field 956 also displays a number of plus symbols denoting the number of regions that have abnormalities detected. Furthermore, patient report 952 contains a patient serial number field 958, a patient name field 960, a gender field 962, an age field 964, and an occupation field 966. Fields 958 through 966 display the information stored in respective fields 606, 608, 610, 612, and 620 (shown in FIG. 22) stored in file 600. For example, patient name field 960 displays field 608 (shown in FIG. 22) stored in file 600. Patient report 952 contains medical reference pictures that a user can compare to the patient's thermal images. A color preset field 972 allows a user to change the color scheme of thermal images 954*a* and 954*b* similarly to color preset field 790 (shown in FIG. 26). A thermal image negative button 974 allows a user to view the negative of thermal images 954*a* and 954*b* similarly to thermal image negative button 792 (shown in FIG. 26). A user can left-click a thermal image enhancement checkbox 976 to smooth out the rough edges of thermal images 954*a* and 954*b*. Checkbox 976 is similar to thermal image enhancement checkbox 882 (shown in FIG. 27). Left-clicking an image background removal checkbox 978 removes any background thermal readings from thermal images 954*a* and 954*b*. Left-clicking a thermal color editing checkbox 980 enables a user to change the color scheme of thermal images 954*a* and 954*b*. Left-clicking checkbox 980 again disables the ability to change the color scheme of thermal images 954*a* and 954*b*. While checkbox 980 is checked, a user can use a temperature setting arrow and temperature limit bar in area 980 similarly to the temperature setting arrow 786 (shown in FIG. 26) and the temperature limit bar 788. While checkbox 980 is checked, a user can also change a temperature range field 984, which performs similarly to the temperature range field 794. While checkbox 980 is checked, a user can also change the colors of the thermal image using a thermal color rate change field 986 similarly to thermal color rate change field 796. When the user is satisfied with the results, the user can left-click a print button 988, which prints out a hard copy of patient report 952, depicted as a patient report printout 1000 (shown in FIG. 30). The user can also left-click a save button 990 which saves the report to file 600. The user can left-click tab 918 to switch to GUI 890 (shown in FIG. 28).

One embodiment of standard medical reference pictures is depicted by reference pictures 968*a*, 968*b*, and 968*c* for the upper respiratory system. The user can utilize reference pictures 968*a*, 968*b*, and 968*c* to analyze vectorized thermal images 954*a* and 954*b* of a specific patient.

In one embodiment, a user may select a specific part of a patient's body being analyzed by utilizing a body region selection field 970 (shown in FIG. 29). Field 970 allows a user to view a different report for each region of the body. Left-clicking field 970 displays a preset list of body regions. Left-clicking a selection from the preset list changes what is displayed in patient report 952 to the corresponding body region.

FIG. 30 illustrates an embodiment of patient report printout 1000. Printout 1000 depicts a resulting hard copy that is the output generated by health evaluation system 40 when print button 988 (shown in FIG. 29) is pressed by a user. All fields in printout 1000 correspond to the respectively numbered fields in GUI 950 (FIG. 29).

Figure 31:
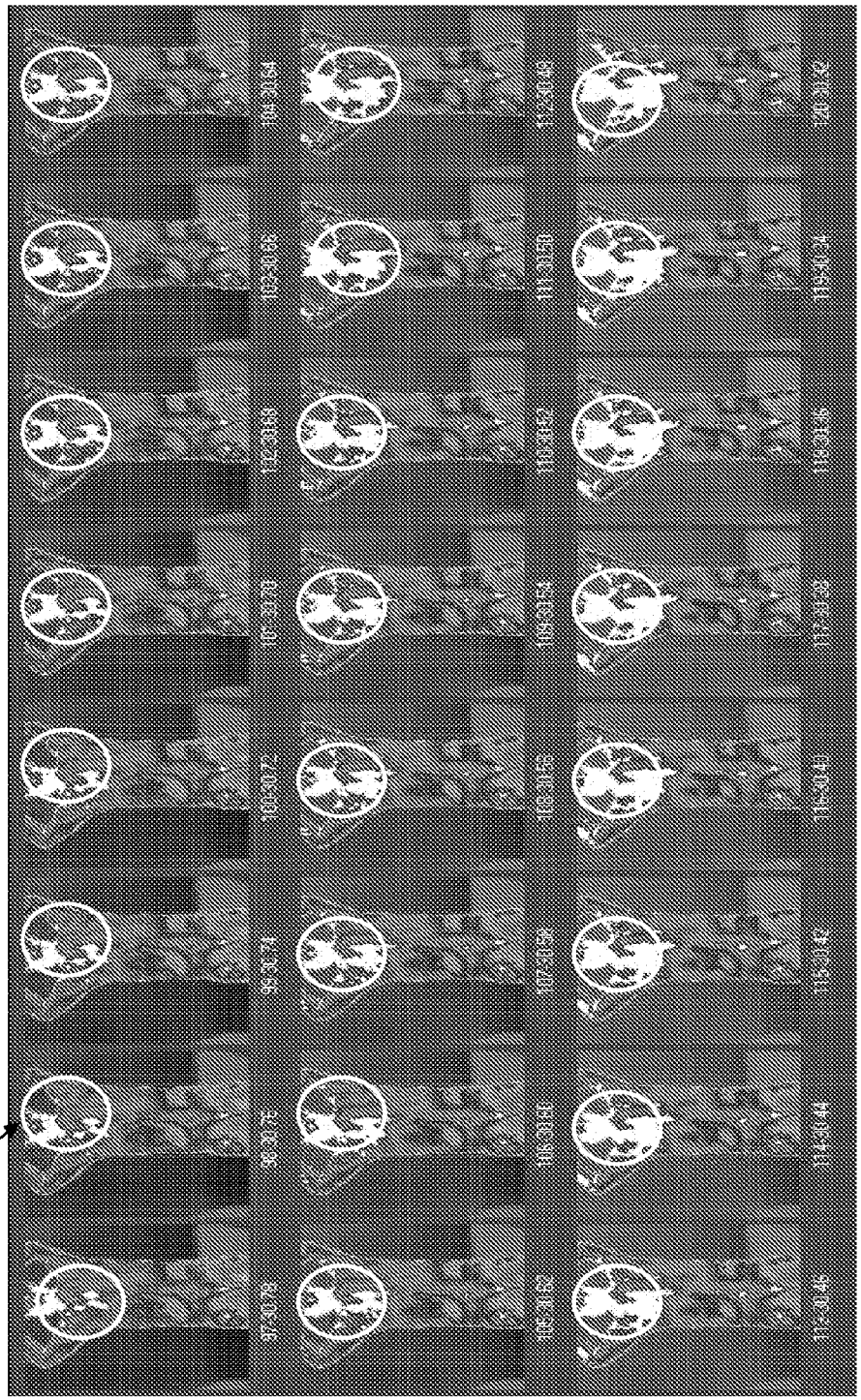
FIGS. 31 and 32 represent partial sectional reports of thermal images.
Figure 32:
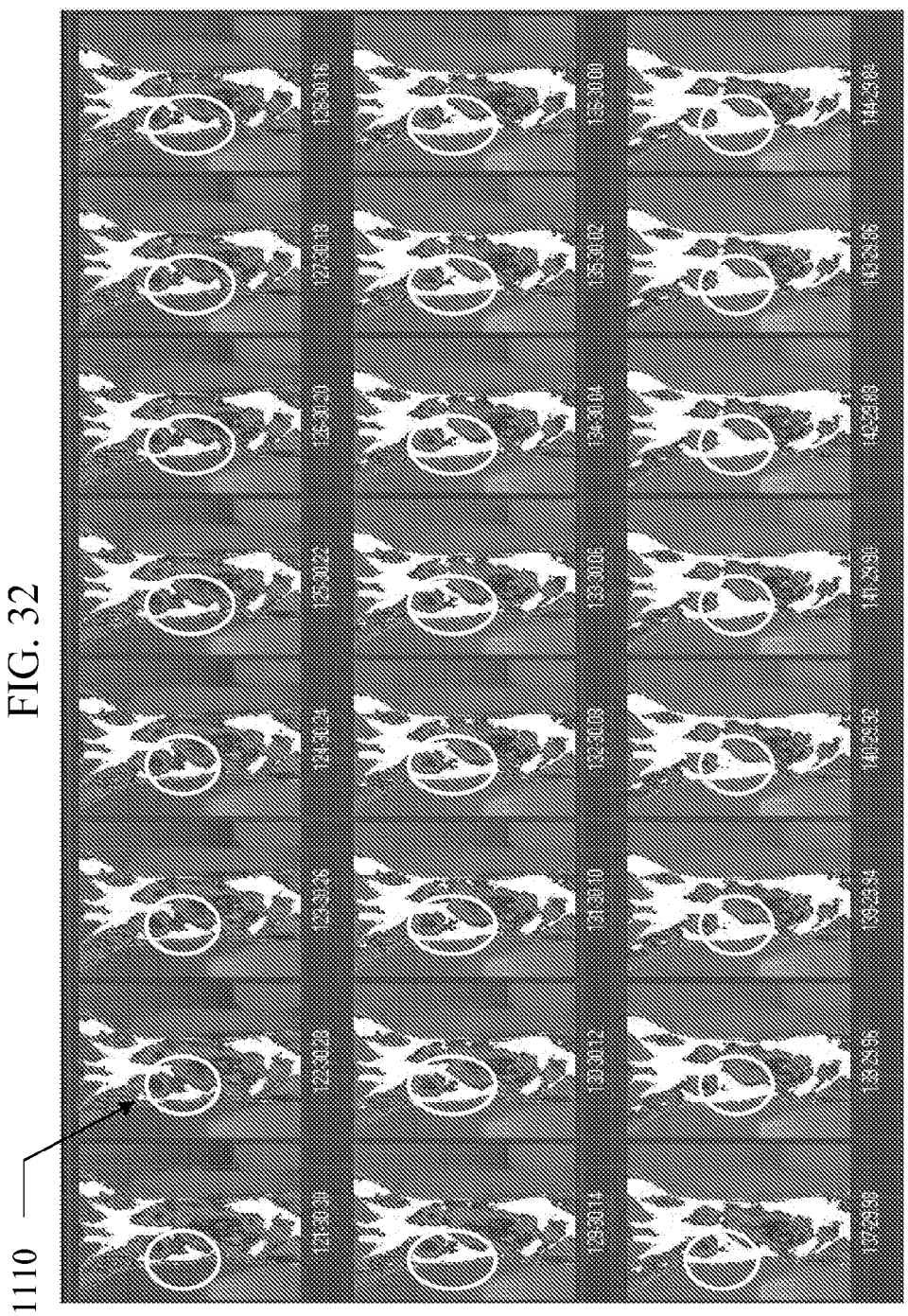

FIGS. 31 and 32 are examples of a partial sectional report of thermal images created by health evaluation system 40 (shown in FIG. 3). Health evaluation system 40 is capable of scanning more than the body's surface area. It can pinpoint and analyze deep heat sources that emanate from the body. Health evaluation system 40 is capable of identifying and locating abnormal internal heat sources from tissues and organs in the body, including the stomach, pancreas, gallbladder, liver, lymph nodes, heart, lungs, brain, blood vessels, and even heat sources under the hair. Health evaluation system 40 is further capable of mapping all the major areas of a body, including the head, spine, arms, legs, hands, and feet.

FIG. 31 is an example of a partial sectional report and a series of thermal mappings of a male. Auto-analysis of the thermal image notes a suspect area which is in circle 1100. The auto-analysis of the thermal mapping suggests at least one of a primary carcinoma of liver; and/or liver cirrhosis (decompensation period). The thermal mapping indicates an abnormal distribution of thermal field at the neck and back, asymmetrical at the two sides, with thermal radiation obviously higher at the left neck, ear, and back than at the right. The abnormal distribution suggests high metabolism problems (e.g. carcinoma) of the hepatic bile. There are pathological changes of the lung, pleura, left neck, and retroauricular lymph node.

Referring now to FIG. 32, a series of thermal mappings of a male. Auto-analysis of the thermal image notes a suspect area which is circled in circle 1110. The auto-analysis of the thermal mapping suggests at least one of a primary carcinoma of liver; and/or liver cirrhosis (decompensation period). The thermal mapping indicates an abnormal distribution of the thermal field at the surface level of the back side of the patient, asymmetrical at the two sides, and thermal radiation at right hypochondria obviously higher than at the left. The report also indicates an increased thermal radiation at the upper chest, left axilla, and lower left abdomen. There is indication of a high metabolism problems (e.g. carcinoma) of the hepatic bile. The analysis does not rule out pathological changes of the lung and pleura, and the left axillary lymph node. The analysis also does not rule out pathological changes of the colon and left iliac fossa.

The TMT system's design presents the body's internal heat temperature details in digital data and colored images on a GUI. Different colors that appear in the images correspond to different temperatures throughout the body. The image data produced is three-dimensional (shown in FIGS. 41B, 42B, and 43B), unlike traditional or current thermal imaging technology which utilizes two-dimensional images.

In one embodiment, health evaluation system 40 (shown in FIG. 3) receives metabolic thermal radiation status and functional imaging of cells, tissues, organs and the body as a whole, and makes qualitative and quantitative analysis and evaluation of the following: 1) texture imaging; 2) tissue status imaging with changes of tissue texture; 3) tissue status/function imaging with changes of tissue texture and functions; 4) function imaging; and 5) function/status imaging with changes of functions and status.

Health evaluation system 40 (shown in FIG. 3) evaluates the thermal intensity of cell, organ, and patient's system metabolism. The human body has a natural thermal balance according to the thermally balanced entity-balance principle. The human body is an entity symmetrical along the central axis according to the central axis-symmetry principle. Thus, basic standards based on the normal positions of body parts and these principles of relative difference may be used. Metabolism changes under external intervention and is dynamic.

Health evaluation system 40 (shown in FIG. 3) provides real-time dynamic prediction, prevention, early warning, and clinical treatment monitoring. Health evaluation system 40 is safe, reliable, efficient, easy to operate, cost-effective, and capable of detecting most abnormalities. Health evaluation system 40 utilizes digital medical imaging technology featuring compact memory and large information volume. Health evaluation system is capable of evaluating a human respiratory system abnormalities, otorhinolaryngological abnormalities, cardiovascular system abnormalities, reproductive system abnormalities, respiratory system abnormalities, digestive system abnormalities, urinary system abnormalities, endocrine system abnormalities, and lymphatic system abnormalities.

Figure 44:
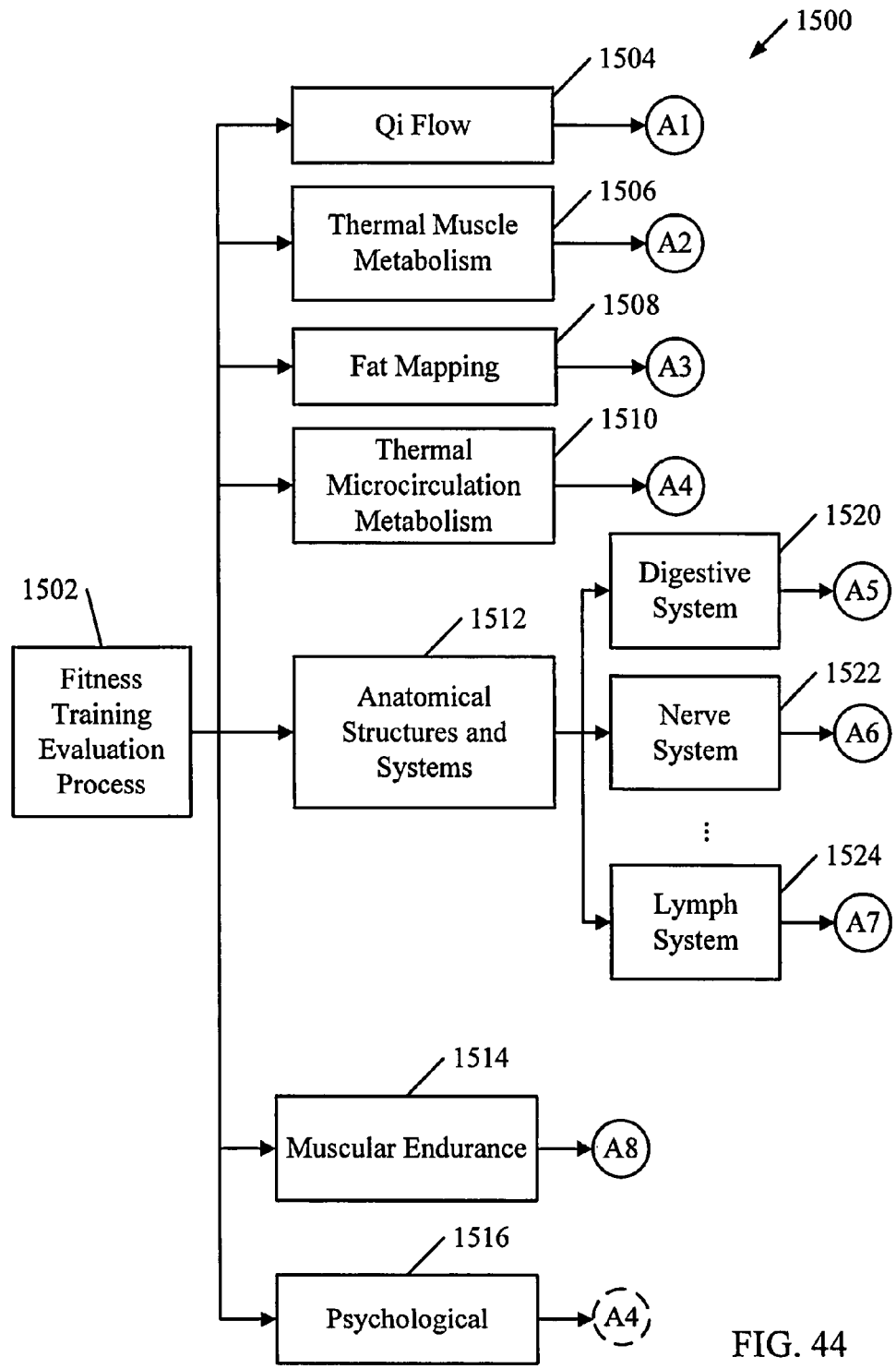
FIG. 44 illustrates a general flow diagram for fitness evaluation process by the TMT health evaluation system.

FIG. 44 is an embodiment of a flow diagram for a fitness evaluation process 1500 that is implemented utilizing health evaluation system 40 (shown in FIG. 3). Fitness evaluation process 1500 has the ability to make determinations as to the anatomy of the human body. Process 1500 is used to analyze the effectiveness of various fitness processes, including fitness training (shown in FIG. 47A), muscle metabolism, body fat content (shown in FIG. 48A), human microcirculation system and/or human vascular system (shown in FIG. 49A), muscle endurance, muscle regeneration, and mental stress. As is seen from the description below, process 1500 may be utilized in the area of sports medicine, physical training, physical therapy, etc.

FIG. 44 illustrates that process 1500 begins once block 1502 is selected. Block 1502 is followed by one of the following processes: a Qi (flow) evaluation process at block 1504, a thermal muscle metabolism evaluation process at block 1506, a fat mapping process at block 1508, a thermal microcirculation metabolism evaluation process at block 1510, an anatomical structures and systems evaluation process at block 1512, a muscle endurance evaluation process at block 1514, or a psychological evaluation process at block 1516. As can be appreciated, fitness evaluation process 1500 may perform some or all of the above processes.

Figure 52A:
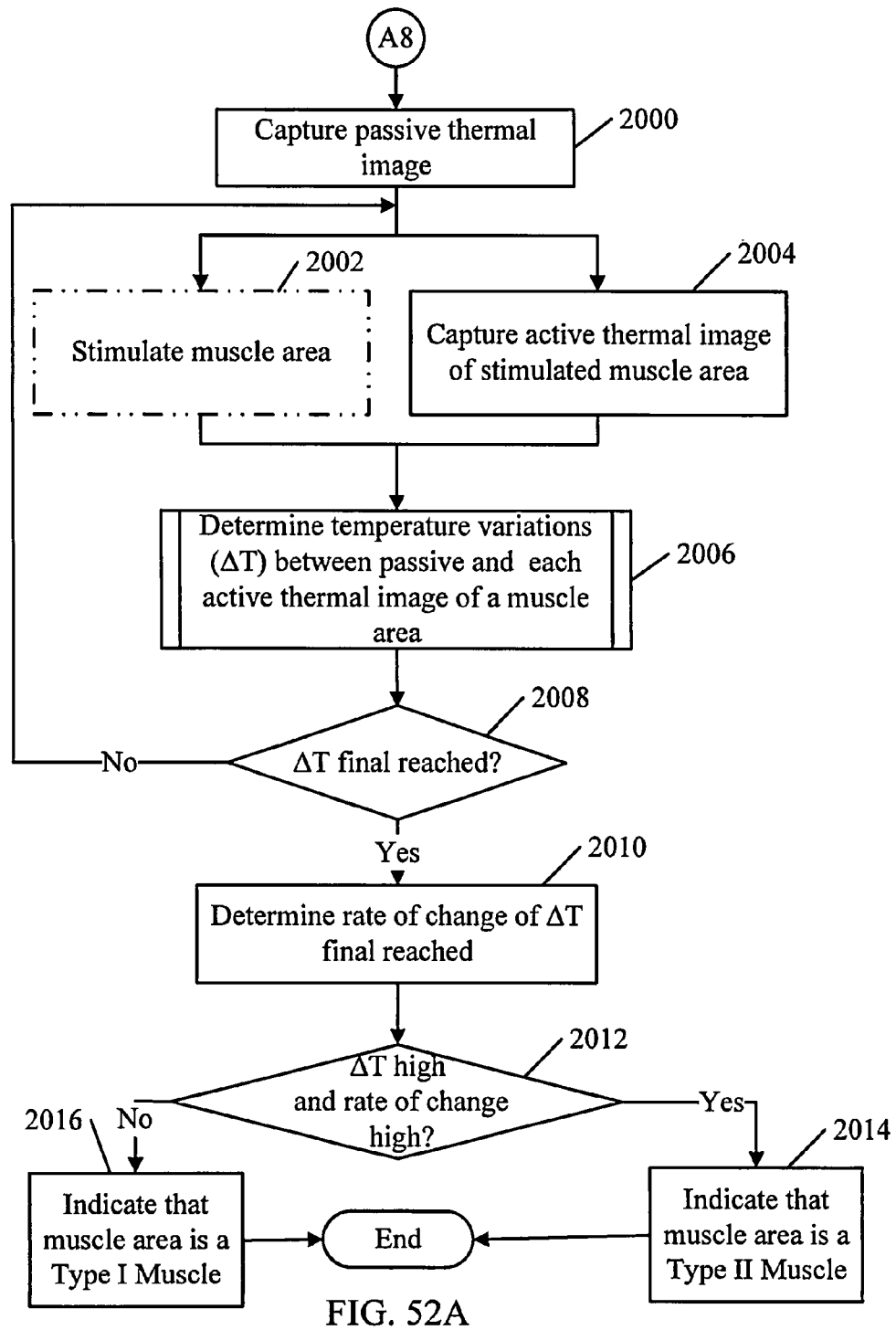
FIG. 52A illustrates a flowchart for a muscle endurance evaluation process.

Anatomical structures and systems evaluation process at block 1512 is selectively followed by one of block 1520 for the digestive system, block 1522 for the nervous system, or block 1524 for the lymphatic system. Block 1512 for anatomical structures and systems evaluation process may be followed by other blocks in addition to blocks 1520, 1522, and 1524. Block 1514 for muscle endurance is also followed by block 2000 as shown in FIG. 52A.

Figure 45A:
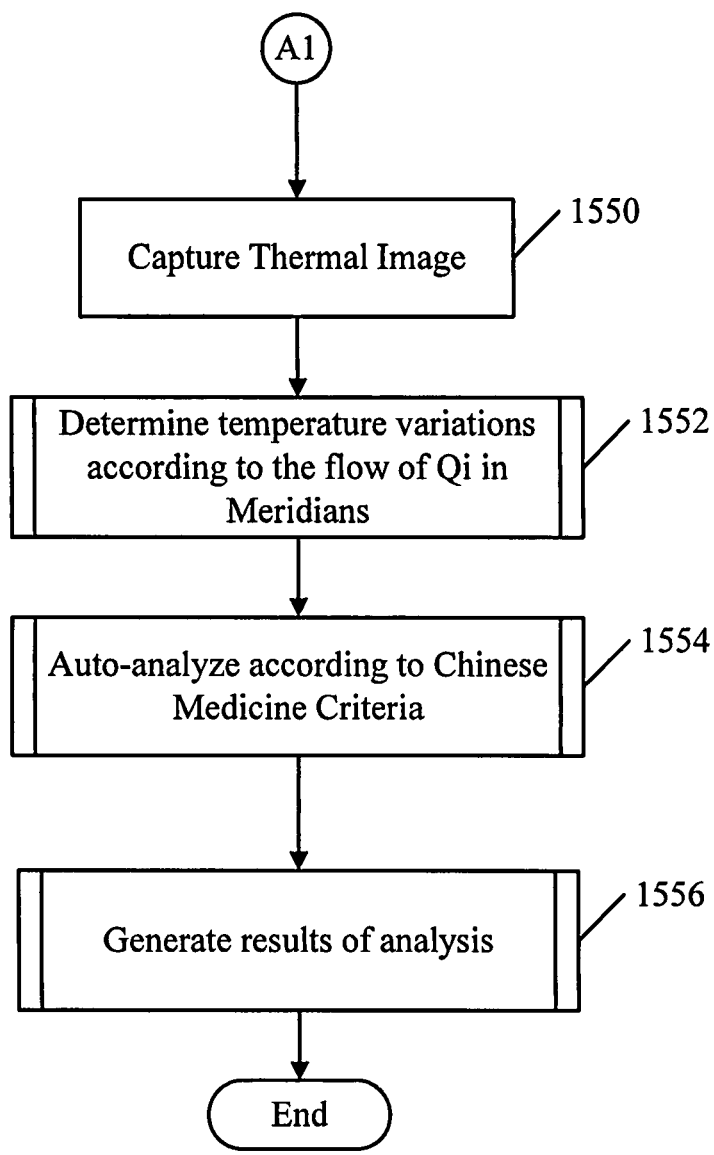
FIG. 45A illustrates a flowchart for a Qi evaluation process.

FIG. 45A illustrates a flowchart for the Qi evaluation process at block 1504. The process requires a thermal image to be captured at block 1550. Once the image is captured, temperature variations are determined according to the flow of Qi in meridians. Block 1552 is followed by block 1554 where the temperature variations are auto-analyzed (such as at block 20 shown in FIG. 2) according to Chinese medicine criteria. Block 1554 is followed by block 1556 where the results of the analysis are generated (such as at block 22 shown in FIG. 2). By way of example, the results may be displayed on a monitor or printed in the form of a report.

FIG. 45B illustrates a human Qi channel diagram template 1570 for use in traditional Chinese medicinal evaluation. Template 1570 is generally used for the zone template. The human Qi channel diagram template 1570 comprises a series of paths "Jingluo" (represented by template lines 1572) in the human body used in Chinese Medicine. Lines 1572, which are called the meridians, represent the flow of blood and "Qi" (pronounced "Chi") within the human body. Qi is a body's vital energy that flows through the meridians. However, one embodiment of a thermal imaging system is used to record thermal images that correspond to the flow of Qi in meridians that can be used in traditional Chinese medicine analysis. When an abnormality in an otherwise healthy body blocks the flow of Qi, such blockage causes an area of the body to become very hot or very cold, which can be measured and reported by health evaluation system 40 (shown in FIG. 3).

FIG. 45C illustrates a thermal image 1575 corresponding to the flow of Qi. In this embodiment, for illustrative purposes, thermal image 1575 is abnormal and is hereinafter referenced as an "abnormal thermal image 1575." Abnormal thermal image 1575 indicates increased temperatures in certain areas, which indicate abnormalities. Abnormal thermal image 1575 contains increased temperature in a head 1576, indicating an abnormality. Moreover, abnormal thermal image 1575 contains elevated temperatures in right chest area 1577 (left part of the chest in the picture), which likely indicates abnormality of the lungs. The abnormality in head 1576 combined with the abnormality in right chest area 1577, denoted by abnormal thermal image, signifies that the patient is suffering from an upper respiratory condition. The findings also suggest an abnormality in a pelvic area 1578 denoted by abnormal thermal image in that area indicating an elevated temperature. However, this may not be because of an abnormality; it may be because the subject is either wearing underpants, or has just recently removed them.

FIGS. 46A and 46B each illustrate an embodiment of front and back anatomy reference images 1590 and 1595, respectively. The front anatomy reference image 1590 is an embodiment of one position in which patient stands. The patient in the front anatomy reference image 1590 is required to stand in front of and facing a thermal camera with his or her arms at the side. Similarly, the patient in the back anatomy reference image 1595 is required to have his or her back towards the camera, with arms at the side. The front anatomy reference image 1590 and back anatomy reference image 1595 are used as a reference to demonstrate how a healthy muscular system should be symmetric. The images also demonstrate how muscular structures are coordinated.

Figure 47A:
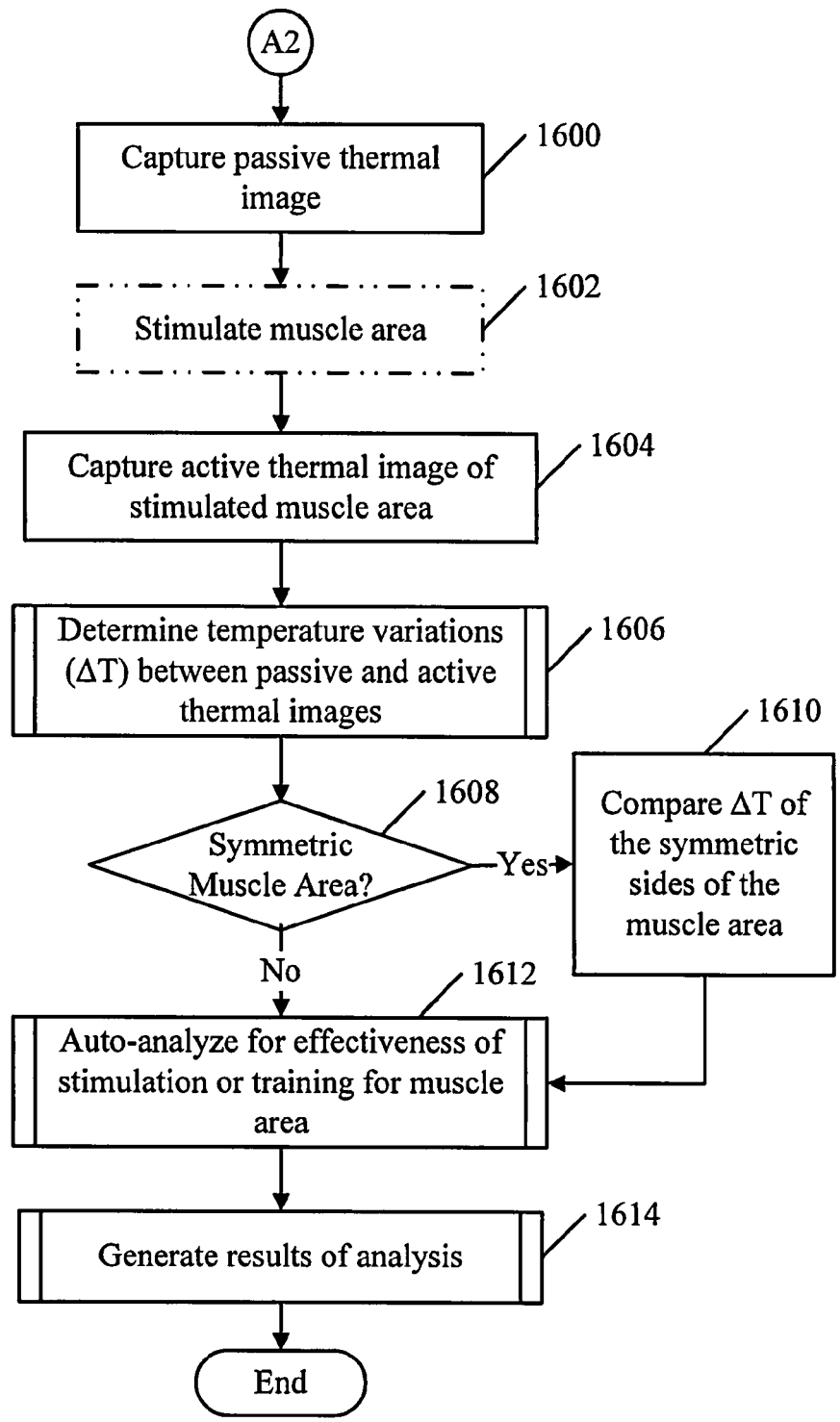
FIG. 47A illustrates a flowchart for the thermal muscle metabolism evaluation process.

FIG. 47A illustrates a flowchart of the thermal muscle metabolism evaluation process at block 1506. The process of FIG. 47A is described in combination with FIGS. 47B and 47C. FIGS. 47B and 47C illustrate a front anatomy image 1690 and a back anatomy image 1695 similar to reference images 1590 and 1595. The thermal muscle metabolism evaluation process identifies user selected muscles and compares their growth in order to determine whether or not a training regimen is effective, and/or what needs to be changed, if necessary.

In one embodiment of the thermal muscle metabolism evaluation process, the patient is first required to stand nude, and still in front of the camera (or thermal imaging device) for approximately fifteen minutes. Then at the end of the fifteen minute-period, a thermal image is taken (the "passive image") at block 1600. At this time the muscles are not stimulated. Block 1600 is followed by block 1602 (shown in phantom) to stimulate a selected muscle area. The stimulation may be achieved by performing exercise that stimulates the selected muscle area. Other types of muscle stimulation may be used such as applying electrical or other stimuli. Block 1602 is followed by block 1604 where a second subsequent thermal image of the stimulated muscle area is taken (the "active thermal image").

By way of example, a patient may be directed to do crunches or sit-ups for the abdominal area, or push-ups for pectoral areas 1692A and 1692B (shown in FIG. 47B). The patient may be directed to perform exercise that stimulates the chest area when comparing the muscle areas 1692A and 1692B (shown in FIG. 47B). The patient may also be directed to perform exercises that stimulate the gluteus area when comparing muscle areas 1697A and 1697B (shown in FIG. 47C). After such stimulation, the active thermal image of the stimulated or exercised muscle area is captured at block 1604.

Referring back to FIG. 47A, block 1604 is followed by block 1606 where temperature variations ($\Delta T$) between the passive and active thermal images in the muscle areas (1692A and 1692B or 1697A and 1697B) are compared. Block 1606 is followed by block 1608 where a determination is made whether the muscle area is symmetric. If the determination at block 1608 is "Yes," block 1608 is followed by block 1610. If the determination is "No," block 1608 is followed by block 1612. Block 1608 is optional if only symmetrical muscles areas are evaluated. Nevertheless, block 1608 allows each muscle to be evaluated independently, if desired by the user.

At block 1610, the temperature variations ($\Delta T$) of the symmetric sides of the muscle area are compared. Block 1610 is followed by block 1612 where the effectiveness of the stimulation or training (exercise) of the muscle area is auto-analyzed. The results of the analysis are generated at block 1614. Thus, muscle area 1692A is compared to 1692B. Muscles are composed of cells. When cells are active, they consume energy and generate heat. A stronger muscle area has more muscle cells, while a weaker muscle area has fewer muscle cells. Therefore, a weaker muscle area generates less heat than a stronger muscle area. The difference in heat, and therefore temperature, can be calculated as the temperature variation $\Delta T$ (Block 1606). The temperature variation $\Delta T$ is the absolute value of the difference of the temperatures of the muscle areas being compared. The $\Delta T$ is calculated comparing the right pectoral box (muscle area 1692A) in the passive image against the right pectoral box (muscle area 1692A) in the active image. Similarly, the temperature variation $\Delta T$ is calculated comparing the left pectoral box (muscle area 1692B) in the passive image against the left pectoral box (muscle area 1692B) in the active image. The process (shown in FIG. 47A) then computes the absolute value of the difference between the temperature variation $\Delta T$ of right pectoral box (muscle area 1692A) and the temperature variation $\Delta T$ of the left pectoral box (muscle area 1692B).

Since the human body is symmetric, the muscle areas should generate the same amount of heat, and the temperature variation $\Delta T$ of the muscle areas should be zero. If the result is greater than zero, the muscle masses are not symmetric and an abnormality exists. The process (shown in FIG. 47A) then compares the right pectoral box to the left pectoral box in the active image. The muscle area with the lower temperature indicates a weaker muscle mass. A physical trainer or physical therapist may interpret the results to find that the smaller muscle area needs more exercise to develop the area more quickly, and can adjust the fitness training or physical therapy regimen accordingly.

The above process may be performed on other muscle areas including symmetrical muscle areas.

Figure 48A:
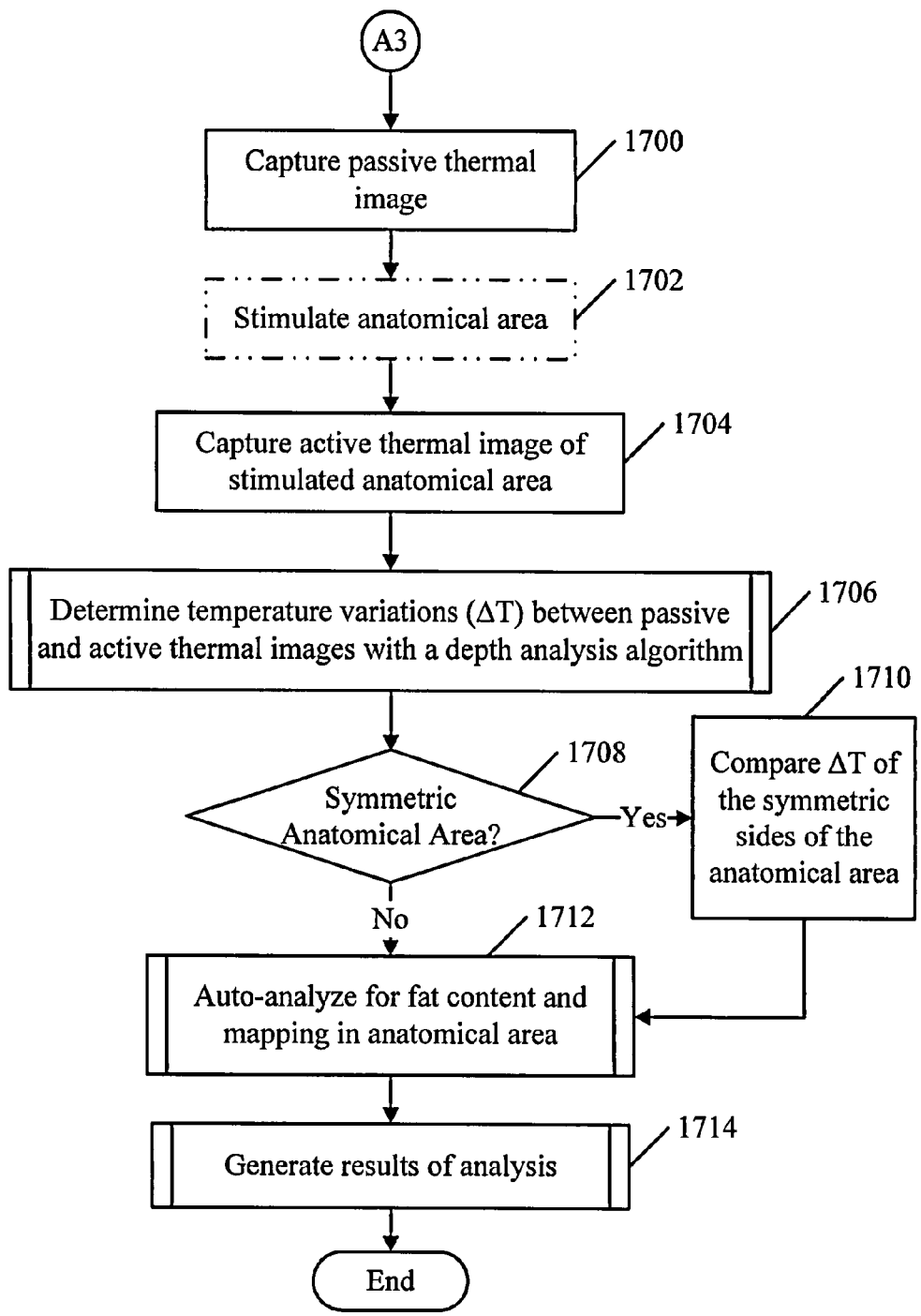
FIG. 48A illustrates a flowchart for the fat mapping evaluation process.

FIG. 48A illustrates a flowchart for the fat mapping evaluation process at block 1508. The process of FIG. 48A is described in combination with FIGS. 48B and 48C. FIGS. 48B and 48C illustrate a front anatomy image 1790 and a back anatomy image 1795 similar to images 1590 and 1595 (shown in FIGS. 46A and 46B). The fat mapping evaluation process determines and compares the fat content of certain areas. Fat is located closer than muscle to the skin surface of a person's body. Fat also has more heat resistance than muscle, and tends to absorb more heat than muscle. Therefore, an area that outputs less heat than the corresponding symmetric area has more fat and less muscle. The fat mapping evaluation process at block 1508 (shown in FIG. 44) analyzes front anatomy image 1790 and back anatomy image 1795 by utilizing a depth analysis algorithm to identify heat at a shallower depth.

Block 1508 (shown in FIG. 44) is followed by block 1700 (shown in FIG. 48A) wherein a passive thermal image is captured. Block 1700 is followed by block 1702 (shown in phantom) to stimulate a selected anatomical area which may contain muscle and fat. The stimulation may be achieved by performing exercise that stimulates the selected anatomical area. Other types of stimulation may also be used such as applying electrical or other stimuli to stimulate the anatomical area (1792A and 1792B or 1797A and 1797B). Block 1702 is followed by block 1704 where a second subsequent thermal image of the stimulated anatomical area is captured (hereinafter referred to as the "active thermal image").

Block 1704 is followed by block 1706 where temperature variations ($\Delta T$) between the passive and active thermal images in the anatomical areas (1792A and 1792B shown in FIG. 48B, or 1797A and 1797B shown in FIG. 48C) are determined. The temperature variations ($\Delta T$) are determined utilizing a three-dimensional thermal image depth analysis described above.

Block 1706 is followed by block 1708 where a determination is made whether the anatomical area is symmetric. If the determination at block 1708 is "Yes," block 1708 is followed by block 1710. If the determination is "No," block 1708 is followed by block 1712. Block 1708 is optional if only symmetrical anatomical areas are evaluated. Nevertheless, block 1708 does permit one area to be evaluated independently, away from any other area.

At block 1710, the temperature variations (ΔT) of the symmetric sides of the anatomical area are compared. Block 1710 is followed by block 1712 where the temperatures variations are auto-analyzed (such as in block 20 as shown in FIG. 2) for fat content and mapping in the anatomical area at block 1712. Block 1712 is followed by block 1714 where the results of the analysis are generated (such as in block 22 as shown in FIG. 2).

Figure 49A:
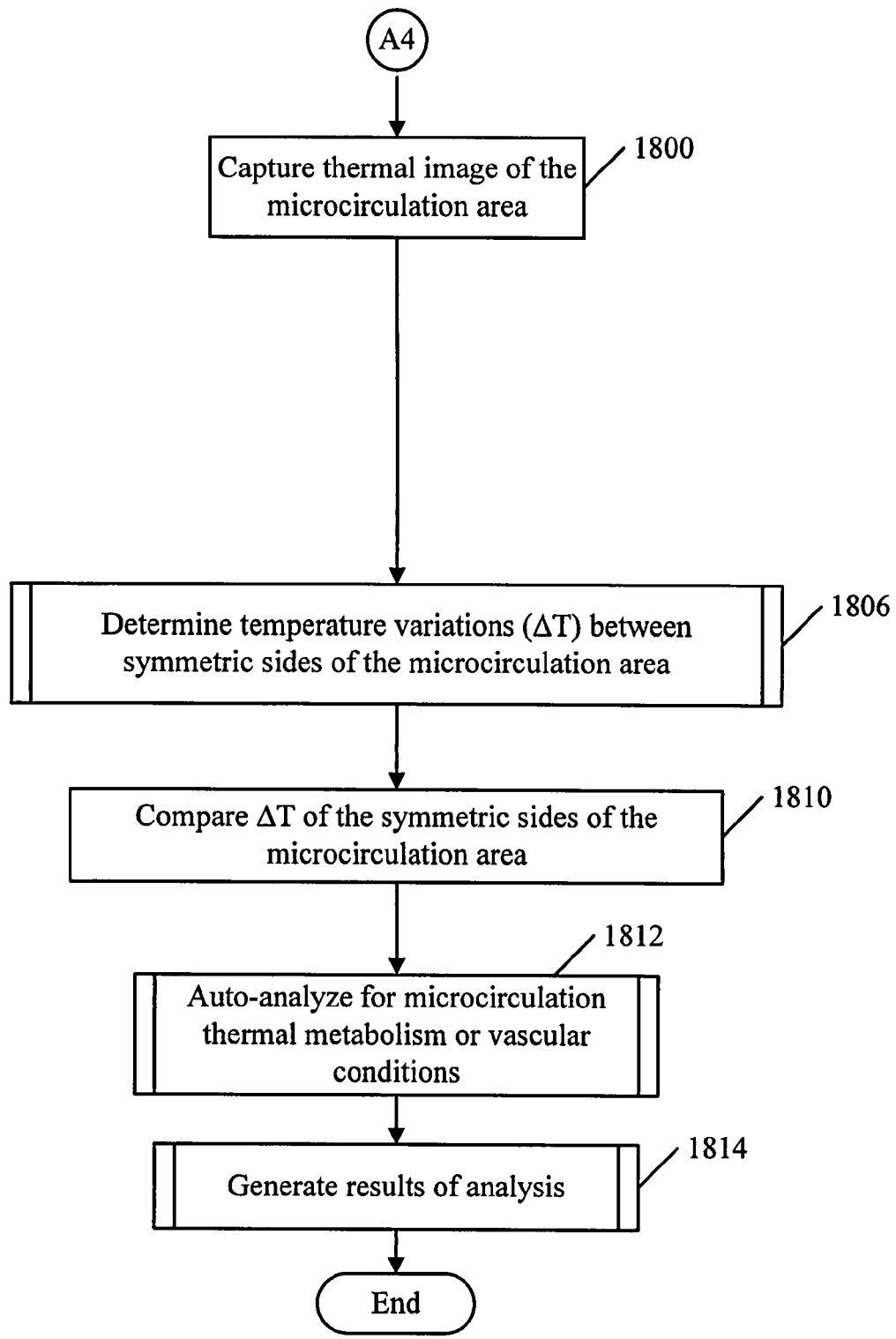
FIG. 49A illustrates a flowchart for the thermal microcirculation metabolism evaluation process.

FIG. 49A illustrates a flowchart for the thermal microcirculation metabolism evaluation process at block 1510 (shown in FIG. 44). The process of FIG. 49A is described in combination with FIGS. 49B and 49C. FIGS. 49B and 49C illustrate a human arterial system image 1890 and a human venous system image 1895 with the microcirculation areas denoted by blocks 1892A, 1892B, 1893, 1894, and 1897A, 1897B, 1898, and 1899. The microcirculation areas, denoted by blocks 1892A and 1892B, correspond to right and left hands. As a frame of reference, the right hand is on the left side of the page. Microcirculation areas 1893 of FIGS. 49B and 1898 of FIG. 49C correspond to the head. Microcirculation areas 1894 of FIGS. 49B and 1899 of FIG. 49C correspond to the feet.

The thermal microcirculation metabolism evaluation process at block 1510 (shown in FIG. 44) determines whether a patient has an abnormal vascular condition based upon analysis of the micro-capillary or microcirculation system in a patient's hands and feet (1892A, 1892B, 1897A, 1897B, 1894, and 1899). Problems in a person's vascular system often appear initially in the micro-capillary or microcirculation system of a patient's hands and feet. When blood first enters the small capillaries in the hands and feet, the blood flows at a normal rate. A healthy vascular system has an even heat distribution throughout the (micro-capillary) microcirculation system. Additionally, veins and arteries do not distinguish themselves in the thermal scan unless there is blockage or infection. Differences in heat distribution are used to determine the types of problems that a patient is suffering from.

For example, in the case of a diabetic condition, the patient generally has an elevated blood sugar level, which can cause an infection in the (micro-capillary) microcirculation system. When the body responds to the infection, the heat in the infected area rises. Therefore, a higher heat in a particular point in the micro-capillary system indicates that the point is inflamed or infected. In another case, blockages in the blood may be determined. If the blood in the (micro-capillary) microcirculation system is blocked, the flow of blood is disrupted and the slower flow of blood generates less heat. On the other hand, the area, in which the blood flow is blocked, increases in temperature. If the circulation in the head is normal, normal heat mappings are viewed in the captured thermal image.

Returning again to FIG. 49A, block 1510 (shown in FIG. 44) is followed by block 1800 in FIG. 49A. At block 1800, a thermal image of the microcirculation system is captured. Block 1800 is followed by block 1806 where the temperature variations are determined for the microcirculation system. Here, the symmetric sides are compared with each other. For example, as shown in FIG. 49B, hand 1892A is compared to hand 1892B. In FIG. 49C, hand 1897A is compared to hand 1897B. In FIG. 49B, box 1894 includes both the left and right feet. Thus, the right and left feet in area 1894 or 1899 are compared with each other. The right and left sides of the head/brain in areas 1893 or 1898 are compared. Block 1806 is followed by block 1810 where the temperature variations (ΔT) are compared for the symmetric microcirculation areas. Block 1810 is followed by block 1812 where the results are auto-analyzed (such as in block 20 as shown in FIG. 2) for thermal microcirculation metabolism or vascular conditions. Block 1812 is followed by block 1814 where the results of the analysis are generated (such as in block 22 in FIG. 2).

The microcirculation metabolism evaluation process calculates and compares the temperature variations ΔT similarly to the thermal muscle metabolism evaluation process. However, the evaluation usually focuses on the hands, feet, and head areas. Evaluation of thermal microcirculation metabolism relies on the natural symmetry of the body to compare a right hand against a left hand, and a left foot against a right foot. When higher or lower points of heat appear in right hand (1892A) and not in left hand (1892B), the process described under FIG. 49A detects an abnormality. Similarly, if there is temperature differentiations in the left foot compared to the right foot, health evaluation system 40 (shown in FIG. 3) detects and identifies abnormalities.

Figure 54A:
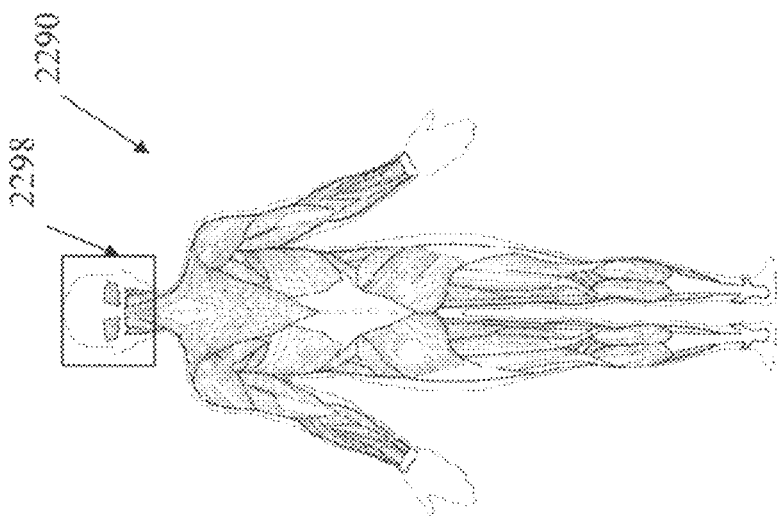
FIG. 54A illustrates a psychological reference image for use in the psychological evaluation process.

FIG. 54A illustrates a physiological reference image 2290 for use in the psychological evaluation process at block 1516 (shown in FIG. 44). Generally, abnormalities in different sections of the brain result in different psychological conditions. Stress and certain psychological conditions cause different parts of the brain to be more active, which, in turn, increases the metabolic rate of cells in the stressed part of the brain, which then increases the temperature of the stressed brain area. The process at block 1516 is essentially the same as that of the process described under FIG. 49A. The right and left sides of the brain images in block 2298 are captured and evaluated. While, in FIG. 49A, the auto-analysis is run for microcirculation or vascular conditions, whereas in the psychological evaluation process at block 1516, the auto-analysis at block 1812 is for areas of abnormal temperature, which indicates potential psychological conditions.

Figure 54B:
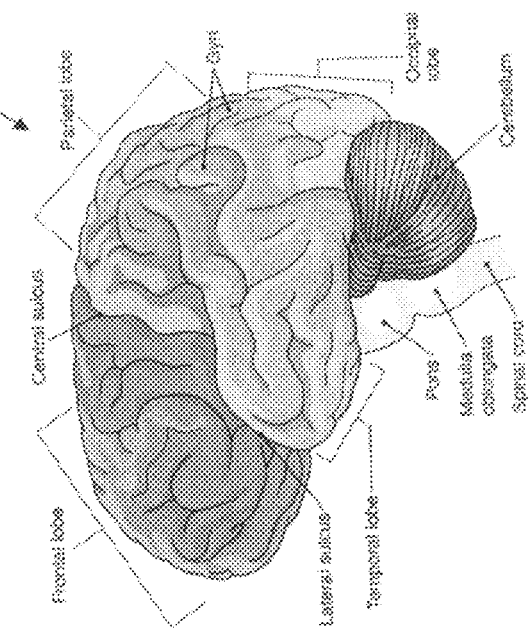
FIG. 54B illustrates a brain diagram template.

Human beings use different parts of their brain when contemplating different functions. When a human being utilizes the brain, the portions of the brain generates heat beyond the normal heat level of the brain. This heat takes approximately eight hours to travel through the bone of the skull, which is easily detectable by thermal imaging. If a person is experiencing stress, the stress may be attributed to excessively concentrating on a particular part of the brain. A thermal image reveals abnormal levels of heat in a particular area of the brain. The brain areas that are evaluated correspond to one of the areas in a brain diagram template 2295 (shown in FIG. 54B). The process calculates the temperature changes (ΔT) between the left side and right side of the brain. If there is any ΔT greater than zero, an abnormality in that brain area is determined and reported.

FIG. 50A illustrates a digestive system reference image 1900. FIG. 50B illustrates a nervous system reference image 1910. FIG. 50C illustrates a lymphatic system reference image 1920. The anatomical structures and system evaluation process of block 1512 (shown in FIG. 44) evaluates the human digestive system at block 1520, the nervous system at block 1522, and the lymphatic system at block 1524. As can be determined from the description below, other systems may be evaluated as well.

Figure 51A:
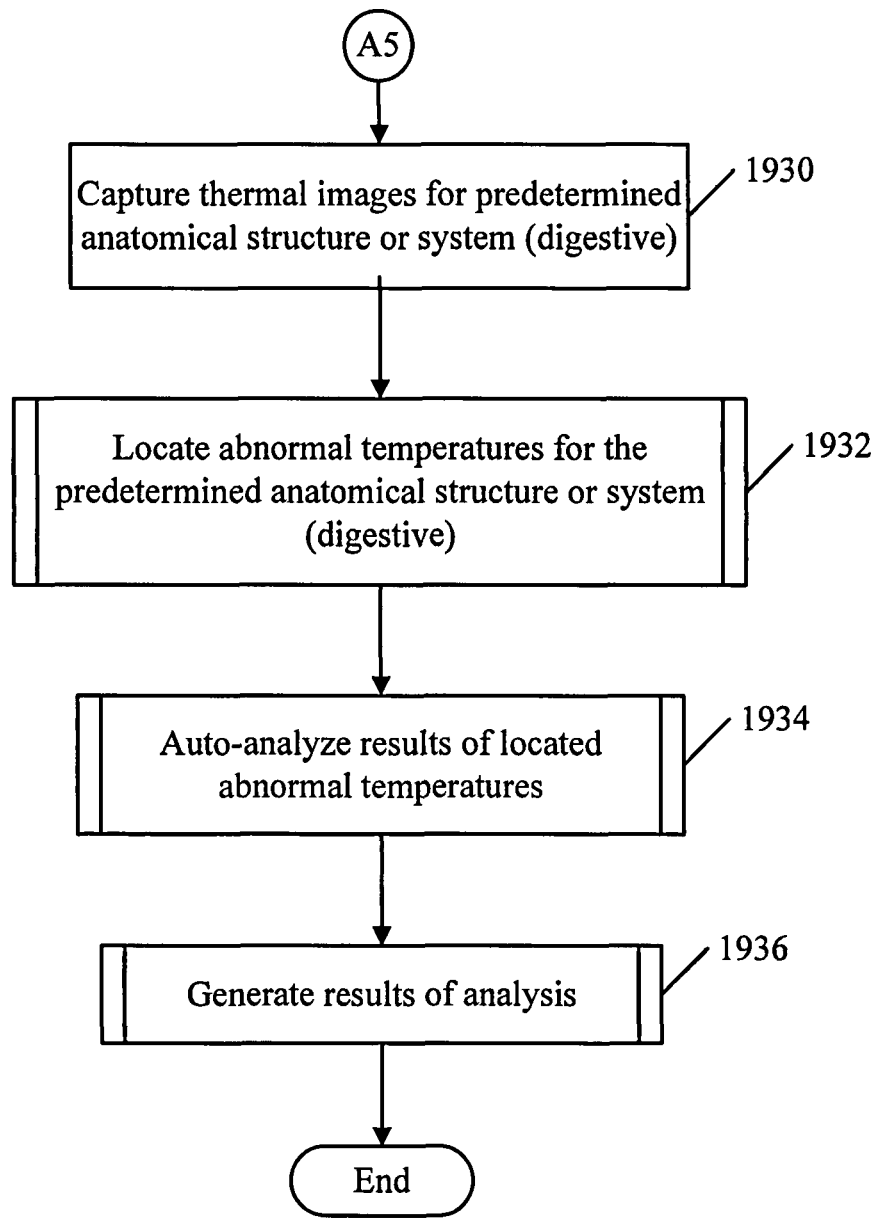
FIG. 51A illustrates a flowchart for an anatomical structure or system evaluation process for the digestive system.

FIG. 51A illustrates a flowchart for an anatomical structure evaluation process for the digestive system. Block 1520 (shown in FIG. 44) is followed by block 1930 where at least one thermal image is captured for a predetermined anatomical structure, such as the digestive system, according to digestive system reference image 1900. A different position (shown in FIG. 50A) is adopted for analysis of the digestive system. For this analysis, the patient's body faces the camera, while the person's head is turned to one side, as depicted in digestive system reference image 1900 (shown in FIG. 50A). Block 1930 is followed by block 1932 where abnormally high temperatures that correspond to the position of digestive system are located in digestive system reference image 1900. Block 1932 is followed by block 1934 where the results of block 1932 are auto-analyzed (such as in block 20 in FIG. 2). Block 1934 is followed by block 1936 where the results of the auto-analysis are generated. (such as in block 22 in FIG. 2)

Figure 51B:
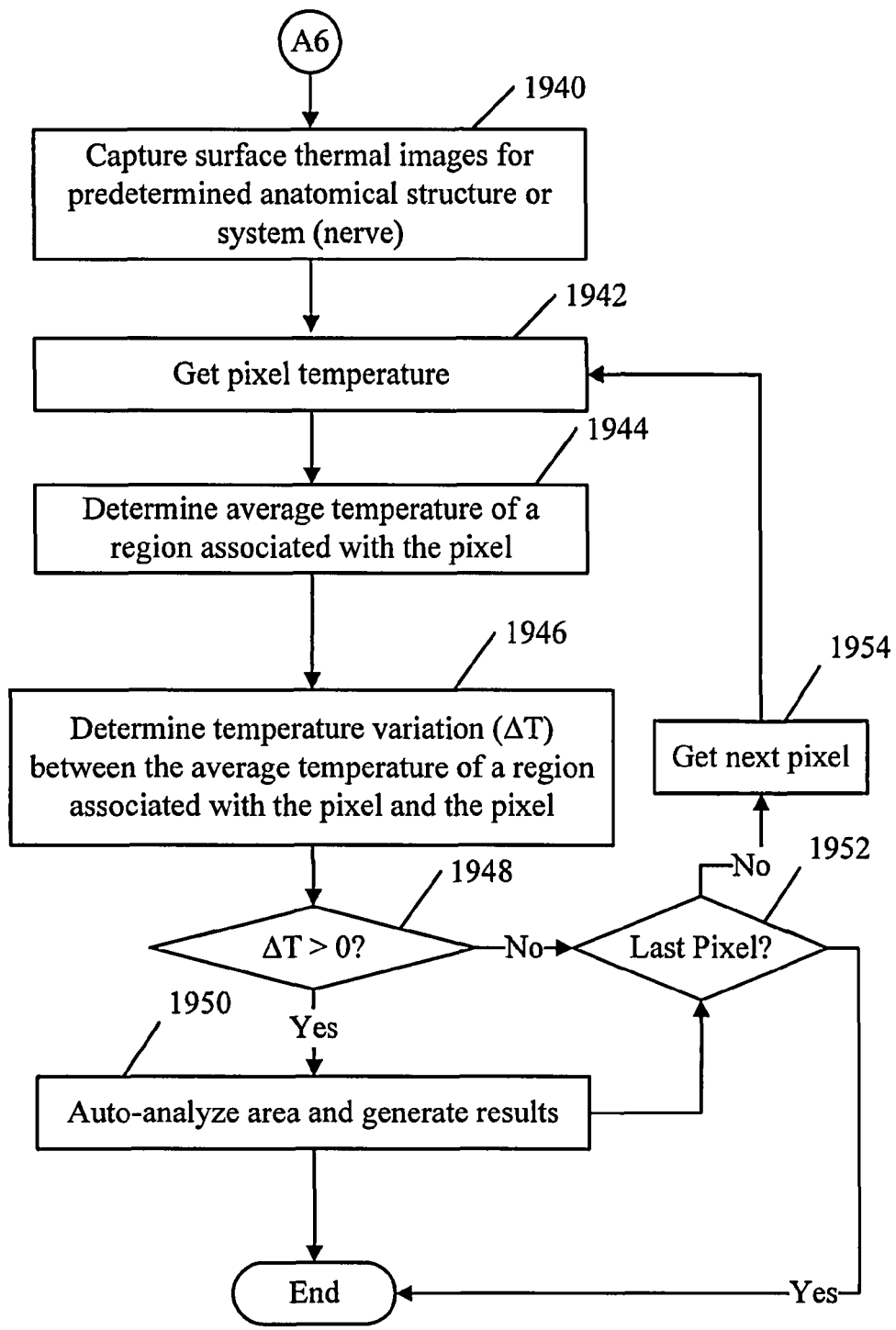
FIG. 51B illustrates a flowchart for an anatomical structure or system evaluation process for the nervous system.

FIG. 51B illustrates a flowchart for an anatomical structure evaluation process for the nervous system. Block 1522 (shown in FIG. 44) is followed by block 1940, where a surface thermal image of the patient's nervous system is captured. A normally functioning nervous system does not display any temperature discrepancies. However, a damaged nerve is inflamed, and therefore generates more heat, and appears as a hot point in the thermal scan. Block 1940 is followed by block 1942 where a pixel and its corresponding temperature in the image are obtained. Block 1942 is followed by block 1944 where an average temperature of a region associated with the pixel is determined. Block 1944 is followed by block 1946 where the temperature variation ΔT between each pixel in the thermal image and a particular region of the body associated with the pixel is determined. If the temperature variation ΔT is greater than zero, as determined at block 1948, then the area associated with the pixel is auto-analyzed (such as in block 20 as shown in FIG. 2) for abnormalities and the results are generated (such as in block 22 as shown in FIG. 2). Block 1950 is followed by block 1952 where a determination is made whether the pixel analyzed is the last pixel. If the determination is "Yes," the process ends. However if the determination is "No", then block 1952 is followed by block 1954. At block 1954, the next pixel is obtained and the process loops back to block 1942. The process is complete when all pixels are evaluated based on nervous system reference image 1910 (shown in FIG. 50B). Returning again to block 1948, if the temperature variation ΔT is not greater than zero, as determined at block 1948 (i.e. determination is "No"), then block 1948 is followed by block 1952 and so on.

Figure 51C:
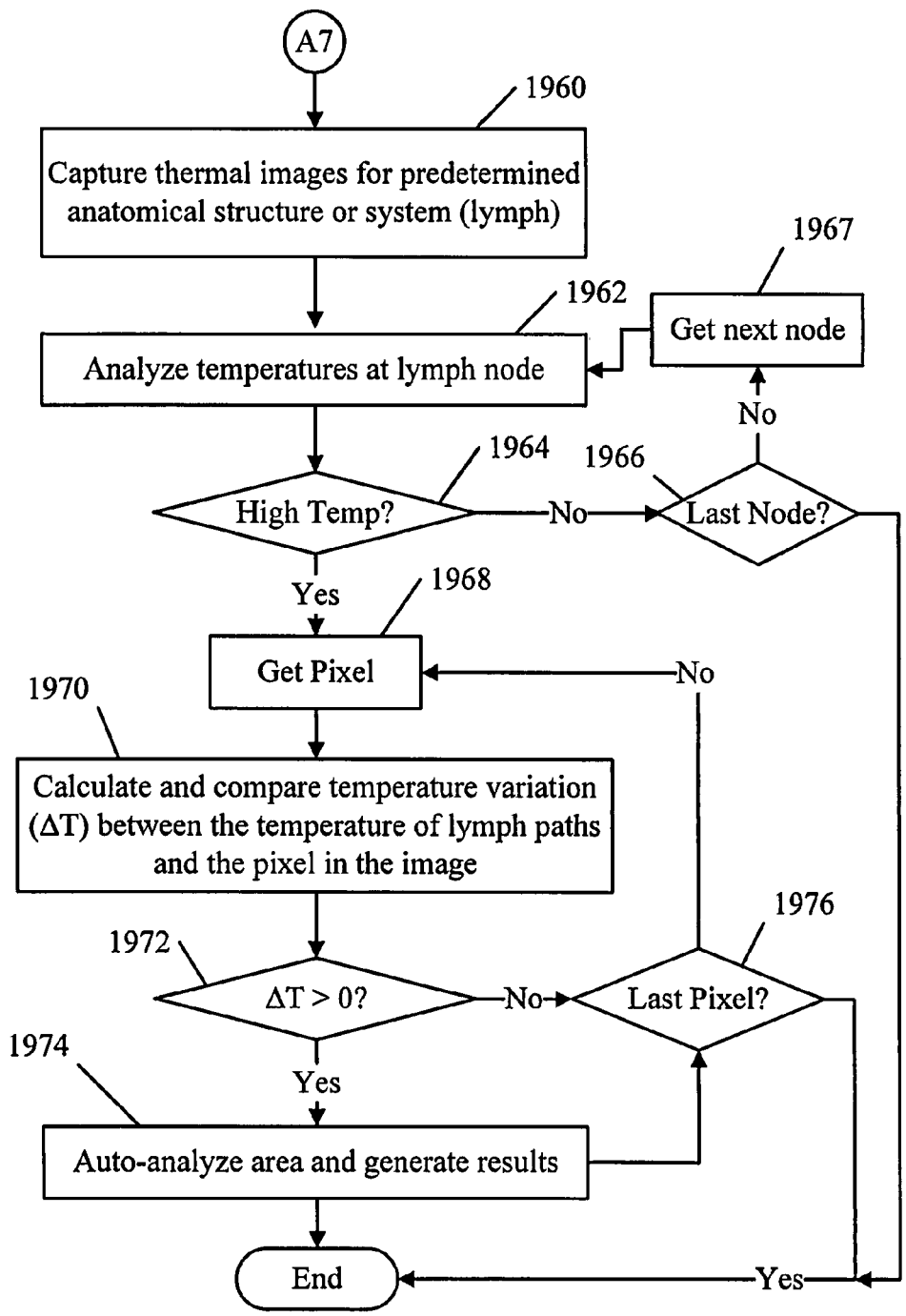
FIG. 51C illustrates a flowchart for an anatomical structure or system evaluation process for the lymphatic system.

FIG. 51C illustrates a flowchart for an anatomical structure evaluation process for the lymphatic system. Block 1524 (shown in FIG. 44) is followed by block 1960, where a thermal image of patient's lymphatic system is captured. The lymphatic system is composed of certain points called lymph nodes connected by lymph vessels, lymph capillaries, and lymph ducts. Infected or inflamed lymph nodes generate higher temperature, and are indications of problems in the lymphatic system. Block 1960 is followed by block 1962, where the lymphatic system, according to a lymphatic system reference image 1920 (shown in FIG. 50C), first identifies the temperature points at which lymph nodes exist. Block 1962 is followed by block 1964 where a determination is made whether a lymph node has a high temperature. If the determination at block 1964 is "No," then block 1964 is followed by block 1966 where a determination is made whether the last node is reached. If the determination at block 1966 is "Yes," the process ends. If the determination at block 1966 is "No," then block 1966 is followed by block 1967 where the next lymph node is obtained. Block 1967 returns to block 1962 until all lymph nodes are analyzed.

At block 1964, if the determination is "Yes," then a pixel and its corresponding temperature are obtained at block 1968. Block 1968 is followed by block 1970 where the temperature variation (ΔT) between the pixel(s) in the thermal image and temperatures of the paths according to the lymphatic system reference image 1920 are calculated and compared. Block 1970 is followed by block 1972. At block 1972, a determination is made whether temperature variation ΔT is greater than zero. If the determination is "No," block 1972 is followed by block 1976 where a determination is made whether the last pixel is reached. If the determination at block 1976 is "Yes," the process ends. However, if the determination at block 1976 is "No," block 1976 loops back to block 1968 to get the next pixel in the image. Returning again to block 1972, if the determination regarding the temperature variation ΔT is "Yes", then block 1972 is followed by block 1974. Block 1974 auto-analyzes and generates results. For example, an alert for an abnormality is generated, if necessary.

FIG. 52A illustrates a flowchart for a muscle endurance evaluation process at block 1514 (shown in FIG. 44). The muscle endurance evaluation process is described in combination with FIG. 52B. FIG. 52B illustrates a front anatomy reference image 2090. Block 1514 is followed by block 2000 where a passive thermal image is captured of the patient according to front anatomy reference image 2090. However, a back image may also be used alone or in combination with the front anatomy reference image 2090.

Block 2000 is followed by blocks 2002 and 2004 shown in parallel. At block 2002, the muscle area under evaluation, such as shown in boxes 2092A and 2092B, is stimulated. At block 2004, active thermal images are captured of the stimulated muscle area. Evaluation of the muscle endurance determines the endurance and fitness of different types of muscle areas. There are two types of muscles in the human body. Type I muscle is a slow oxidative, slow twitch, or red muscle. Type I muscle carries more oxygen and is used for sustained aerobic activities, such as long-distance running. Type II muscle is a fast twitch muscle, which generally contracts and expands more rapidly than Type I muscle, and is used for rapid anaerobic activities, such as sprinting. Evaluation of muscle endurance is used to gauge muscle growth in a patient, which gives a trainer or physical therapist an overview of the effectiveness of the training program or therapy.

In one embodiment, at block 2002, the patient is instructed to exercise for fifteen minutes. While the patient is performing exercise or the muscle area is stimulated through other means, thermal images of the patient are captured every few minutes ("active images") at block 2004. A separate set of images must be taken for each session. Blocks 2002 and 2004 are followed by block 2006 where the temperature variations (ΔT) between the passive and active images are determined. The system compares the temperature of each muscle area of the active images against each muscle area of the passive images to calculate the ΔT.

While the patient exercises or the patient's muscle area is stimulated by other means, the temperature variation (ΔT) from the muscles at rest increases until temperature variation (ΔT) reaches a constant value. The constant value once reached is maintained until the patient stops exercising. Block 2006 is followed by block 2008 where a determination is made whether the final ΔT is reached. If the determination is "No," block 2008 loops back to blocks 2002 and 2004 so that the exercise or stimulation continues, and active images continue to be captured. If the final ΔT is reached and the determination at block 2008 is "Yes," then block 2008 is followed by block 2010. At block 2010, the rate of change of the temperature variation (ΔT) is determined.

The temperature variation (ΔT) combined with the final ΔT maintained determines whether the muscle areas of a patient are composed of more Type I or Type II muscles. The rate of change in the temperature variation (ΔT) of the muscles demonstrates whether the muscles are burning energy quickly or slowly. A high rate of change in the temperature variation ($\Delta T$) of a patient, coupled with a higher final $\Delta T$ indicates that the muscles developed are more suited for quick activities that need to rapidly burn energy, which in turn, indicates a greater growth in Type II muscle. A slow rate of change in the temperature variation ($\Delta T$), coupled with a lower final $\Delta T$, indicates that the muscles developed are more suited for prolonged activities which use energy slowly and evenly, which in turn, indicates a greater growth of Type I muscle.

Block 2010 is followed by block 2012 where a determination is made whether the temperature variation ($\Delta T$) combined with the final $\Delta T$ maintained are both high. If the determination at block 2012 is "Yes," block 2012 is followed by block 2014 where the muscle area is indicated as a Type II muscle. However, if the determination at block 2012 is "No," then the muscle area is indicated as a Type I muscle at block 2016.

In one embodiment, the evaluation of the muscle endurance is repeated for several months, during which the trainer or physical therapist can evaluate whether the status of muscle growth against its intended purpose.

In FIG. 52B, only one set of symmetrical muscles is shown. However, other muscle areas are also evaluated. In FIG. 52B, the muscles in box 2092A include at least one of the pectoral muscle areas, and the biceps brachii located on the right upper arm. The muscles in box 2092B also include at least one of the pectoral muscle areas, and the biceps brachii located on the left upper arm. The gluteus area in FIG. 47C can also be evaluated as well as with other muscle areas.

The evaluation of muscle endurance can also be used to determine whether a patient's muscles are damaged. This evaluation, in turn, is useful for trainers or physical therapist to determine whether their regimen is overly intense. The process for evaluating damaged muscles is similar to the process described in FIG. 47A. However, in one embodiment, the active thermal image is taken approximately 12 hours after stimulation. Normally, after a person exercises or the person's muscles are stimulated, it takes approximately 12 hours for the muscles to return to their "at rest" temperature without any additional relaxants or therapies, such as hot showers and saunas. As can be appreciated, the amount of time necessary to return to "at rest" temperature may vary from individual to individual.

In one embodiment to evaluate damaged muscles, a passive thermal image of the patient "at rest" is first captured. Then, the muscle is stimulated through exercise or other means of stimulation for a predetermined time such as one hour. The patient returns the following day, approximately 12 hours later. An active image is captured of the patient after the patient is undressed. This active thermal image is then compared to the original passive image taken the previous day. By way of example, FIG. 53 illustrates a front anatomy reference image 2190 for muscle damage evaluation. In FIG. 53, the pectoral muscle area in boxes 2192A and 2192B are selected for evaluation.

Based on the evaluation utilizing the process depicted in FIG. 47A, a higher temperature for a muscle area in the more recent image (active image) indicates that the heat in the muscle area is dissipating more slowly than normal. If heat dissipates more slowly, or has not changed back to normal, it indicates that the muscle is likely damaged.

As can be readily seen from the above, health evaluation system 40 (shown in FIG. 3) utilizes TMT mapping technology capable of providing warnings and locating degenerative diseases. Health evaluation system 40 also provides an on-going monitoring of one's physical health. A core aspect of health evaluation system 40 is that it scans and analyzes below-the-surface areas of the head and body. A patient's fat, muscle distribution, and other functions are also analyzed utilizing the mapping technology. The positions and scope of an individual's pains and inflammations can also be observed.

Figure 55:
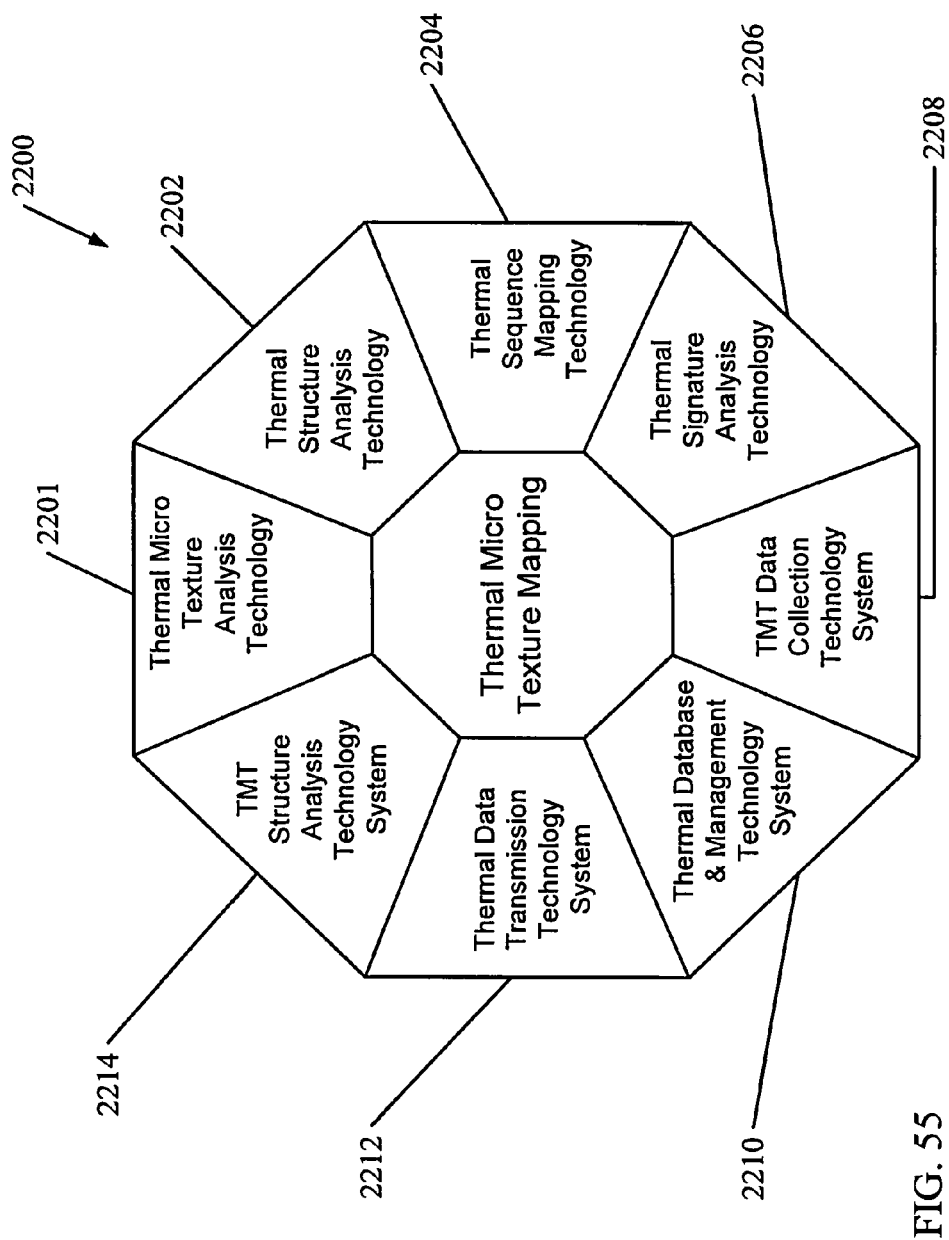
FIG. 55 illustrates an overview of the TMT mapping technology assembly.

FIG. 55 illustrates an overview of the TMT mapping technology assembly 2200 for use in health evaluation system 40 (shown in FIG. 3). TMT mapping technology assembly 2200 includes, in one embodiment, technologies that enable health evaluation system 40 to perform the functions described above. TMT mapping technology assembly 2200 includes a TMT analysis technology module 2201 constructed and arranged to analyze the texture of the thermal images. TMT mapping technology assembly 2200 further includes a thermal structure analysis technology module 2202, a thermal sequence mapping technology module 2204, and a thermal signature analysis technology module 2206. In the context herein, "structure" is actually the three-dimensional view of the thermal image, as shown in FIGS. 41B, 42B, and 43B, as used in the depth analysis. On the other hand, "signature" is the two-dimensional view of a thermal image, such as best seen in FIGS. 41A, 42A, and 43A. Thermal structure analysis technology module 2202 analyzes and processes three-dimensional views of thermal images for abnormalities. On the other hand, thermal signature analysis technology module 2206 analyzes and processes two-dimensional views of thermal images for abnormalities.

The thermal sequence mapping technology module 2204 includes a software, hardware and/or firmware to perform the cascade chromatography process. In general, the cascade chromatography process creates a series of thermal images that start with the small white area(s), and end with a larger white area, as shown in FIGS. 40A, 40B, and 40C. It is not uncommon to produce a sequence of 30 or more series of thermal images.

Module 2204 is part of sectional view module 90 that contains the depth analysis and also displays the sequence of thermal images of the cascade chromatography analysis to the user. This involves thermal sequence mapping technology, which generates the sequence or series of images with a small white spot and ends with a larger white spot.

While performing the cascade chromatography analysis, the longer the analysis takes (when more thermal images result from the cascade chromatography analysis), the deeper is the source of the heat. For example, if there are only 5 images before the cascade chromatography analysis is completed, the heat is shallower. Alternatively, if there are 50 images, the abnormal heat is coming from a deeper area of the body.

Areas of abnormally high temperature, as determined in the analysis, conform to general shapes. The shapes formed by the analysis are known as a "signature" and vary according to a particular anatomical area and the abnormality that exists within that anatomic area. In one embodiment of a signature, an illness within the vascular system would show abnormal temperatures in the thermal image. The pixels that correspond to abnormal temperatures in the vascular system would form a tube-like shape.

The TMT mapping technology assembly 2200 includes a TMT data collection technology module 2208, a thermal database and management technology system module 2210, a thermal data transmission technology module 2212, and a TMT structure analysis technology module 2214. Module 2208 allows users and operators to collect data for carrying out the processes described herein. Module 2210 develops and manages the database data and constructs. Module 2212 enables users and operators to transmit, receive, and retrieve data from remote sites. Module 2214 provides the hardware for carrying out the instructions from Module 2202.

Figure 56:
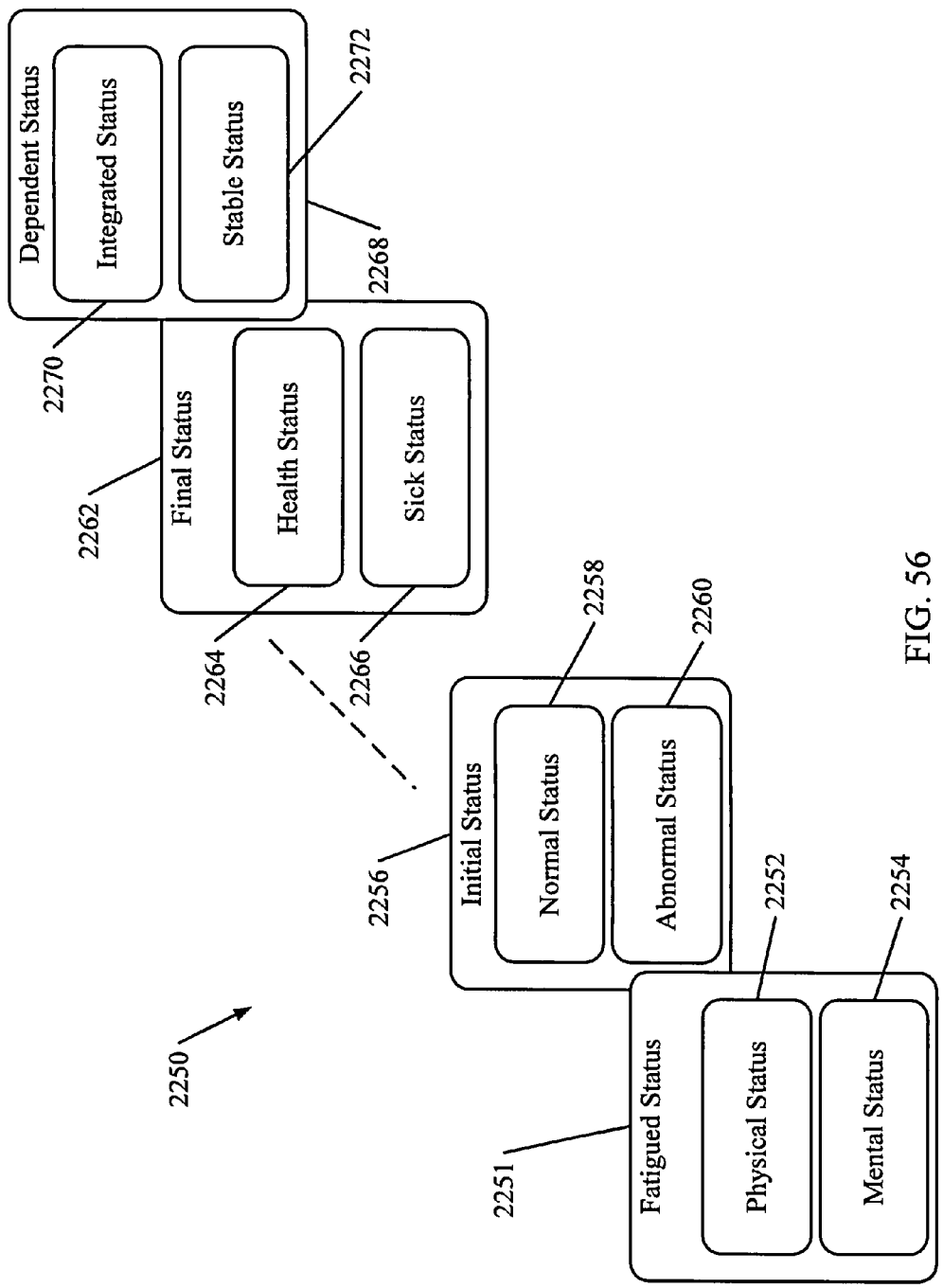
FIG. 56 illustrates preventive medicine treatment through treatment process.

FIG. 56 illustrates preventive medicine treatment through a treatment process 2250. Process 2250 begins with a fatigued status phase 2251, which involves a potentially ill or fatigued patient. The illness either stems from a physical status 2252 relating to physical abnormalities or illness, or a mental status 2254 which is related to psychological abnormalities or illness. A patient in fatigued status phase 2251 then seeks a diagnosis under an initial status phase 2256. Initial status phase 2256 indicates whether a patient is undergoing TMT scanning for the first time. Under initial status phase 2256, an initial thermal scan of the patient is captured. If no abnormalities are detected in the initial scan, the patient has a normal status 2258 and does not need further treatment or analysis. If abnormalities are detected, then the patient has an abnormal status 2260. After the initial scan, a patient under abnormal status 2260 is relaxed using various methods, such as a series of massages or saunas, or floating in a small pool of water. After relaxation, the patient then undergoes TMT scanning again.

If no abnormalities are detected, then the abnormalities were likely due to stress. Stress often causes psychological conditions, and can also induce actual or perceived physical illness. If there are any abnormalities after relaxation, then the abnormalities are most likely physical and the person may be admitted to a hospital or a clinic to be treated, and the patient proceeds to a final status phase 2262. The patient is then treated for any illness. If the treatment is successful, the patient is in a healthy status 2264 and needs no further treatment. If the initial treatment is not successful, then the patient is in a sick status 2266.

A patient in sick status 2266 then moves to the dependent status phase 2268. A patient in phase 2268 either has an integrated status 2270 or a stable status 2272. A patient with status 2270 undergoes constant treatment, involving periodic scans with TMT technology to determine the effectiveness of the treatment. One embodiment of a patient with status 2270 is a person who has cancer and is treated with chemotherapy or radiotherapy. The cancer is treated over a period of time and generally requires periodic TMT scans to determine the effectiveness of the treatment. A patient in status 2272 successfully undergoes further treatments, is now healthy, and needs no further treatment.

Figure 57:
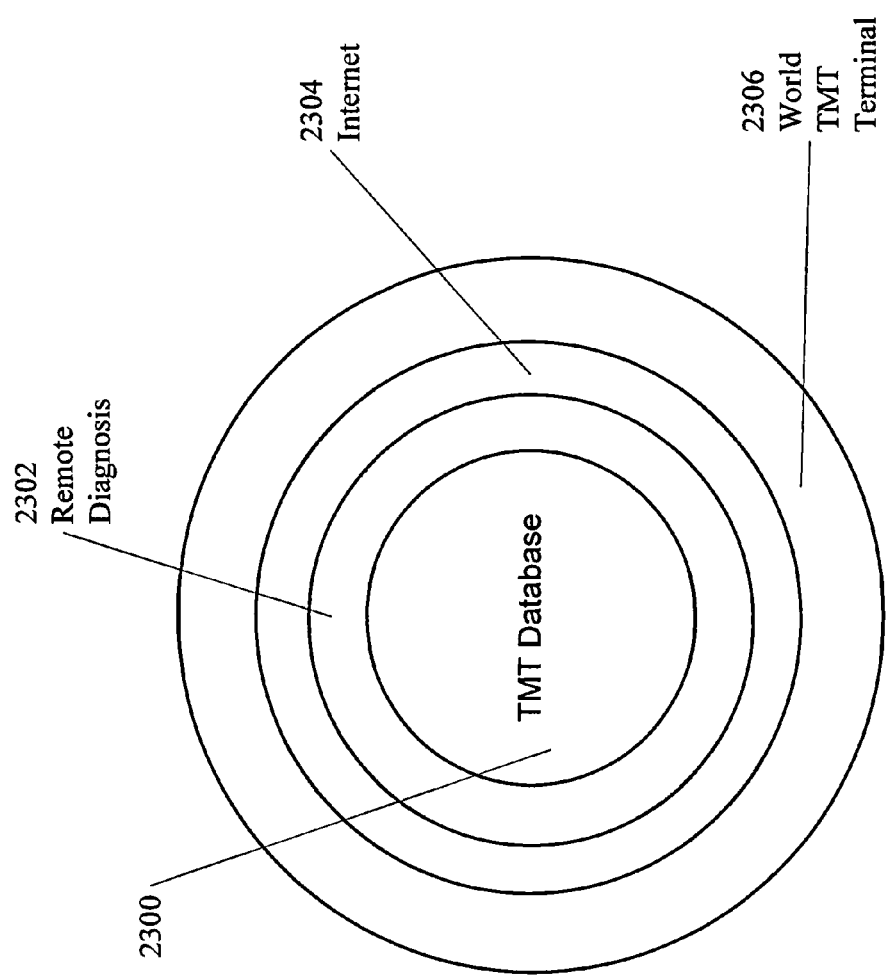
FIG. 57 illustrates a TMT database structure overview.

FIG. 57 illustrates a TMT database structure overview. A TMT database 2300 is in the center of a plurality of concentric rings. The concentric rings include a remote diagnosis ring 2302, an Internet ring 2304, and a world TMT terminal ring 2306. Each ring provides the database information and management for remote diagnosing, Internet communications, and TMT operations worldwide according to a variety of international medical standards. This provides the necessary information for the human anatomy based on race, color, age, environment, etc.

Figure 58:
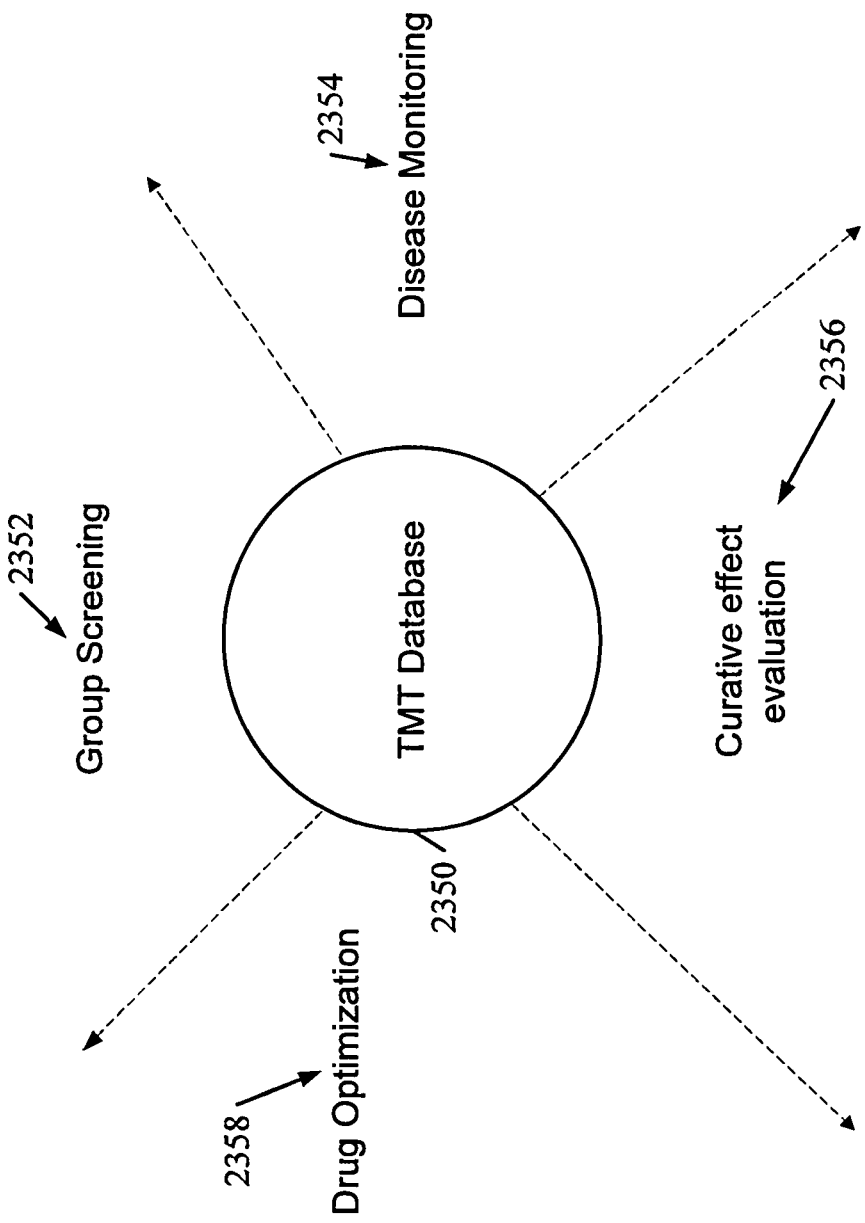
FIG. 58 illustrates a TMT database assembly.

FIG. 58 illustrates a TMT database assembly 2350. Assembly 2350 provides and archives information for tracking, monitoring and evaluation of various patients. Assembly 2350 is used in many processes, including but not limited to: a group screening 2352, a disease monitoring 2354, a curative effect evaluation 2356 and a drug optimization 2358. In one embodiment, group screening 2352 stores information pertaining to one or more patients' diseases and treatments in assembly 2350. The patient information in assembly 2350 is used in monitoring 2354, evaluation 2356, and optimization 2358. Monitoring 2354 is a process that enables a user to track a patient's diseases. Evaluation 2356 is a process that records the effect of different treatments on patients and stores the treatment information in assembly 2350. Optimization 2358 is a process that retrieves information pertaining to the effect of different treatments from assembly 2350 and determines which treatment is best for the patient.

Figure 59:
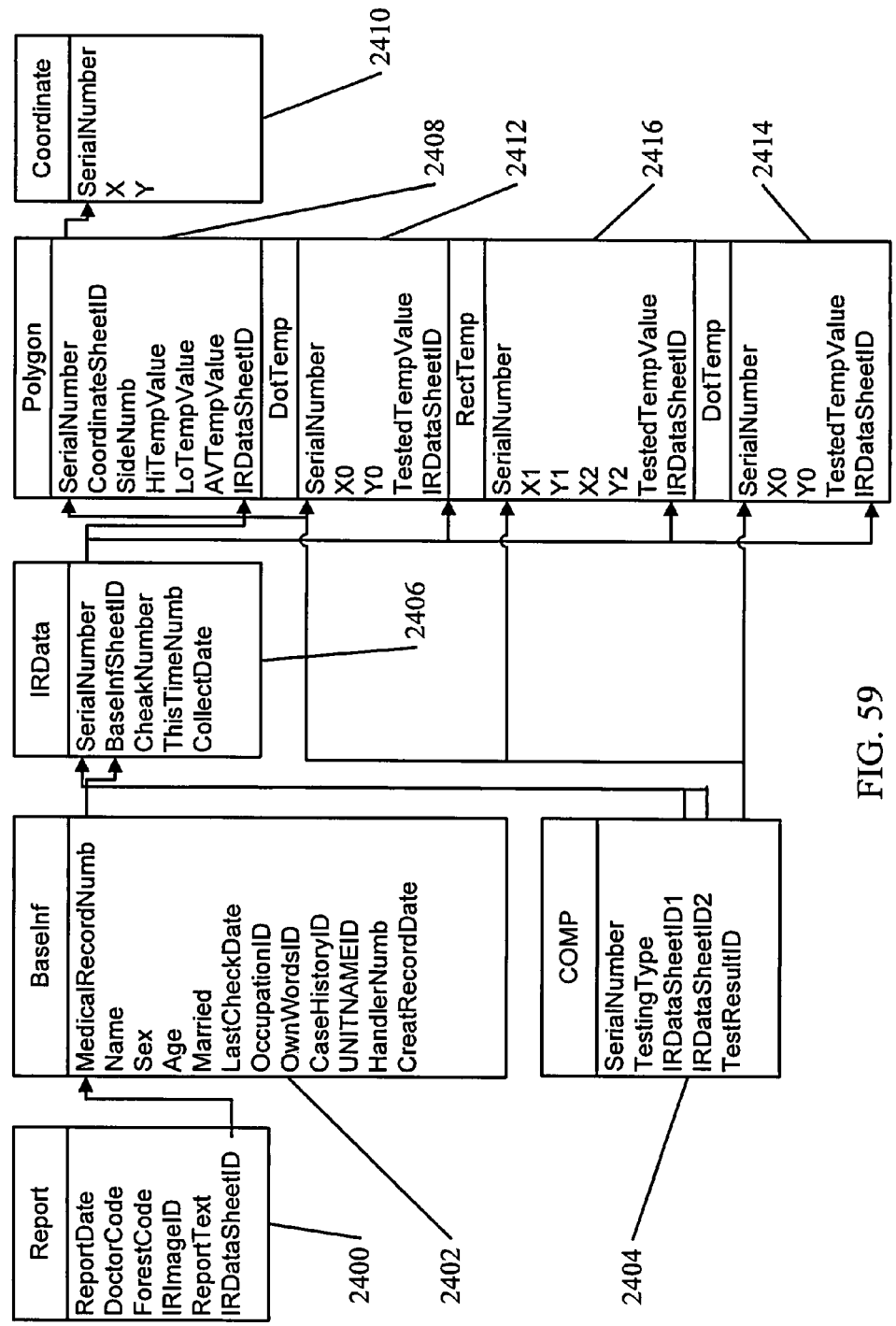
FIG. 59 illustrates a database structure relating to one of the components of the health evaluation system.

FIG. 59 illustrates a database structure relating to one of the components of system 40. A Report object 2400 contains fields that correspond to values and settings for the thermal image analysis report. A BaseInf object 2402 contains fields for information associated with a patient record. A Comp object 2404 contains fields for information regarding types of tests and comparisons. An IRData object 2406 contains information about the thermal image. A Polygon object 2408 contains information for the polygons contained in a three dimensional thermal image. A Coordinate object 2410 contains the x and y coordinates of a point within Polygon object 2408. DotTemp objects 2412 and 2414 contain information for the pixels in a thermal image. A RectTemp object 2416 contains information about a particular area within a thermal image defined by the two pairs of x and y coordinates.

Figure 60:
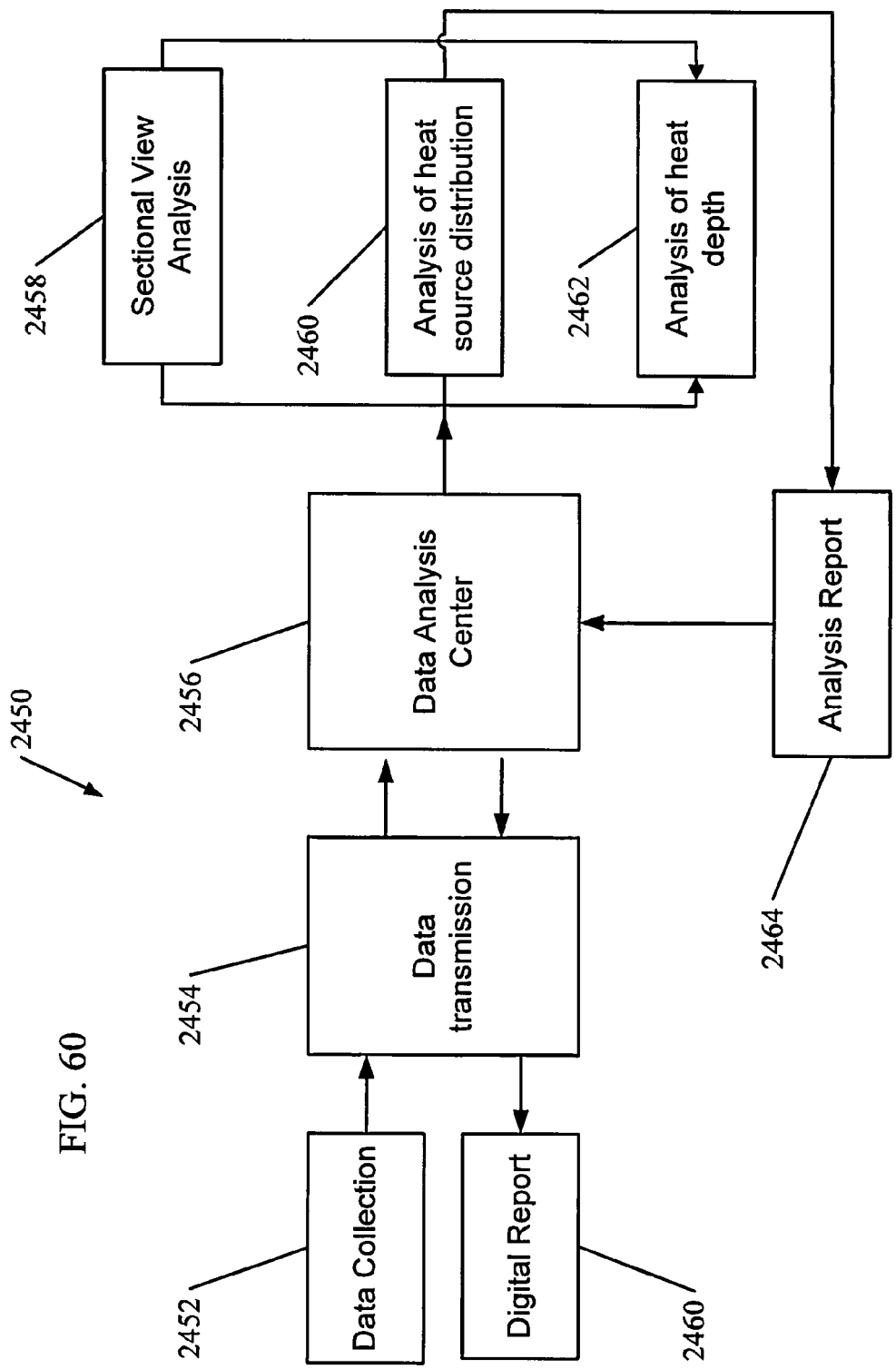
FIG. 60 illustrates a block diagram for a remote TMT analysis process.

FIG. 60 illustrates a block diagram for a remote TMT analysis process 2450. Process 2450 begins with data collection at block 2452. The collected data is transmitted via data transmission block 2454. Block 2454 is followed by a data analysis center block 2456. Block 2456 is followed by three parallel blocks—2458 for sectional view analysis, block 2460 for analysis of heat source distribution, and block 2462 for heat depth analysis. Blocks 2458, 2460, and 2462 are followed by block 2464 where the report of the analysis is generated. Block 2464 returns the information to block 2456 (data analysis center), which transmits the results through block 2454 to block 2466 for digital reporting.

Figure 61:
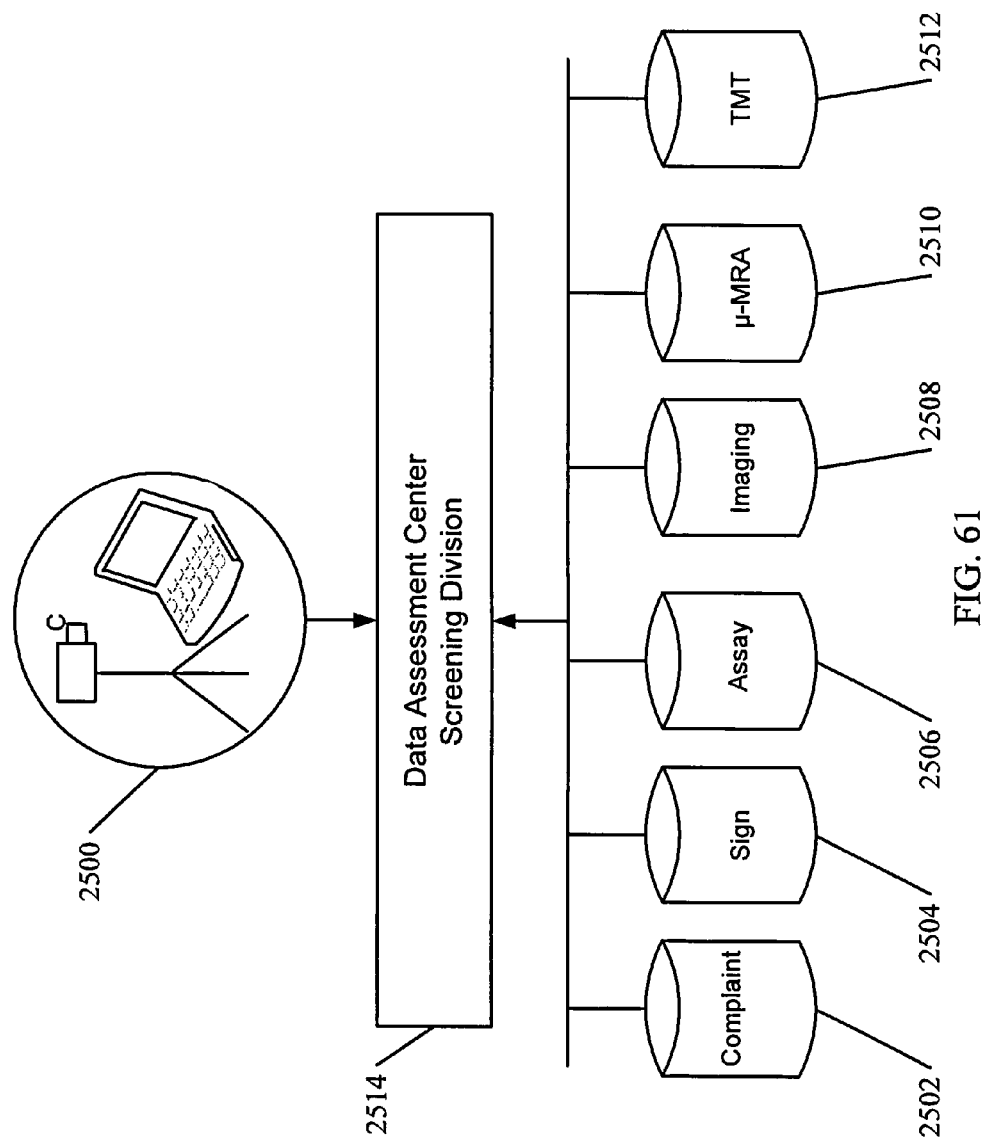
FIG. 61 illustrates a block diagram for remote TMT health screening system.

FIG. 61 illustrates a block diagram for remote TMT health screening system. The system includes image capturing at block 2500. The captured information is sent to the screening division of a data assessment center at block 2514. The data assessment center accesses data from a plurality of databases. The database includes complaint database 2502, a sign database 2504, an assay database 2506, an imaging database 2508, a μ-MRA database 2510, and a TMT database 2512.

Figure 62:
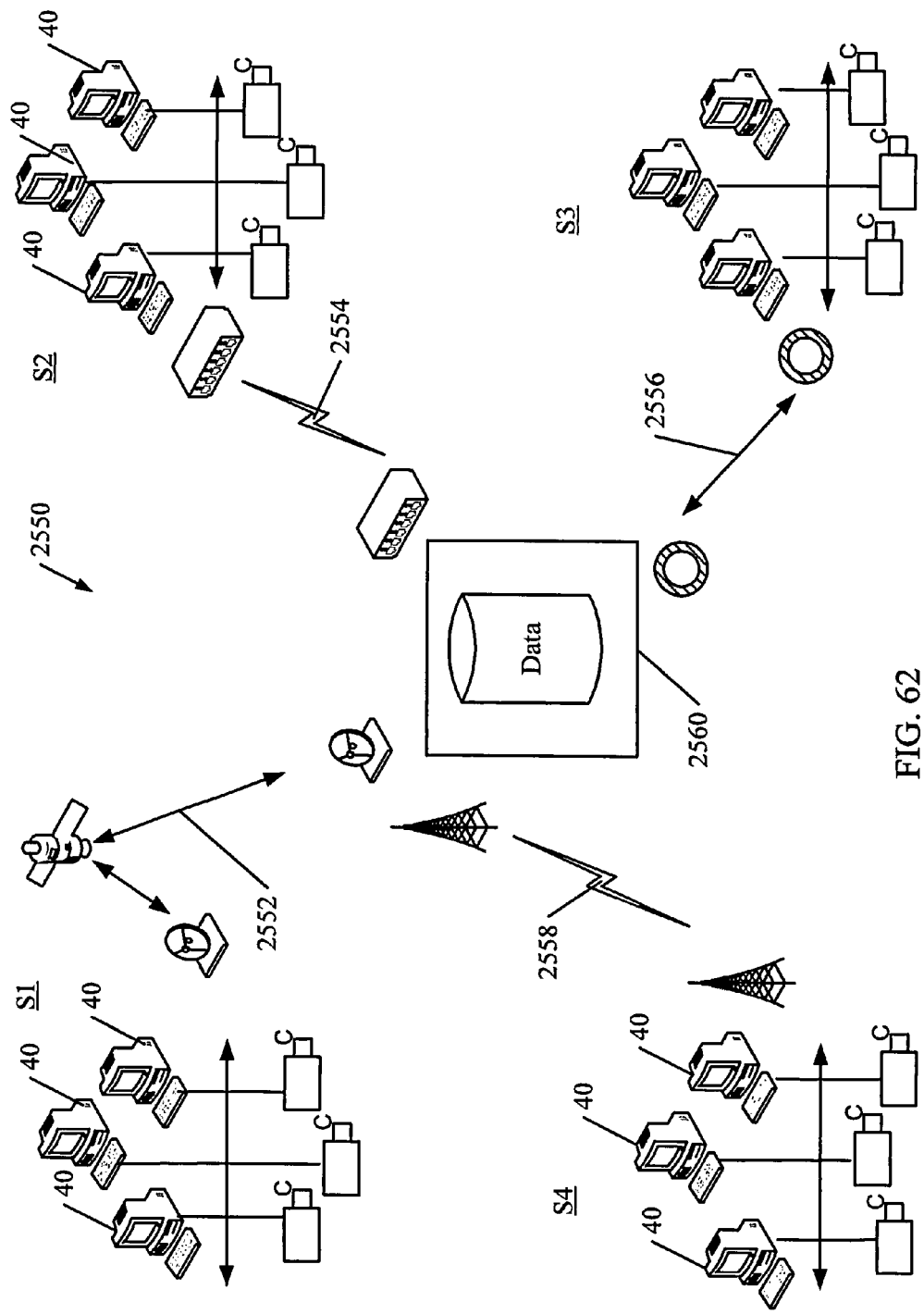
FIG. 62 illustrates a network diagram for remote TMT health screening or analysis.

FIG. 62 illustrates a network for remote TMT health screening or analysis 2550. Network 2550 supports a satellite communication 2552, a modem communication 2554, a cable communication 2556, and a wireless communication 2558. The remote sites S1, S2, S3, and S4 include a plurality of distinct health evaluation systems 40 (shown in FIG. 3) that are not necessarily locally adjacent. Each health evaluation system 40 at site S1 is capable of transmitting and receiving data from a central database site 2560.

The user of any one health evaluation system 40 (shown in FIG. 3) can access a central database 2560 which contains patient information and medical information. Users can potentially access database 2560 through a satellite communication 2552, Intranet or Internet networks via modem 2554, or cable communication 2556, or wireless communication 2558.

Figure 63:
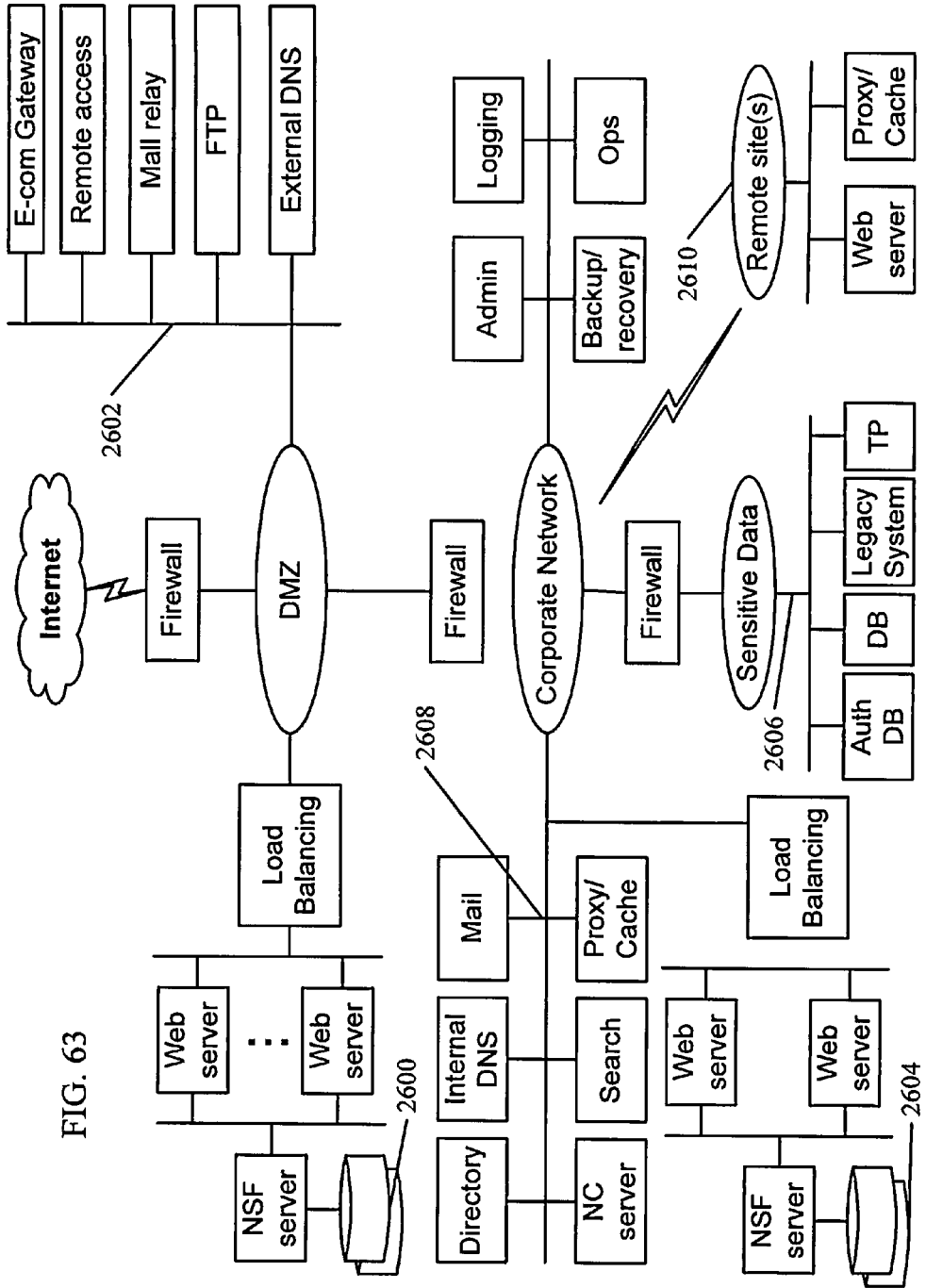
FIG. 63 illustrates a network diagram for multiples networks.

FIG. 63 illustrates a network diagram for multiple networks through which a user can transmit analysis data to and from the patient database. In one embodiment, data stored in a database 2600 is transferred over the Internet through various servers, facilitated by different communication protocols 2602. In another embodiment, data stored in a database 2604 or behind a firewall as sensitive data in various databases 2606 is transmitted through an internal corporate network and accessible through various communication protocols 2608. Data in a corporate network is accessible through remote sites 2610 using various communication protocols.

In one or more configurations, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and without limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technology such as infrared, radio, and microwave is included in the definition of medium.

Disk and disc, as used herein, include compact disc (CD), laser disc, optical disc, digital versatile disc (DVD), floppy disk, and blu-ray disc, where disks usually reproduce data magnetically, while discs reproduce data optically with lasers. Combinations of the above should also be included within the scope of computer-readable media.

A person skilled in the art would recognize that other components and/or configurations might be utilized in the above-described embodiments, if such other components and/or configurations do not depart from the intended purpose and scope of the present invention. Moreover, all terms should be interpreted in the broadest possible manner consistent with the context. In particular, the terms, comprises and comprising, should be interpreted as referring to elements, components, or steps in a non-exclusive manner, indicating that the referenced elements, components, or steps may be present, or utilized, or combined with other elements, components, or steps that are not expressly referenced.

While the present invention has been described in detail with regards to the above described embodiments, it should be appreciated that various modifications and variations may be made in the present invention without departing from the scope or spirit of the invention. In this regard, it is important to note that practicing the invention is not limited to the applications described hereinabove. Many other applications and/or alterations, including alterations to graphical user interfaces, may be utilized provided that such other applications and/or alterations do not depart from the intended purpose of the present invention.

Also, features illustrated or described as part of one embodiment can be used in another embodiment to provide yet another embodiment such that the features are not limited to the specific embodiments described above. Thus, it is intended that the present invention cover all such embodiments and variations as long as such embodiments and variations come within the scope of the appended claims and their equivalents.

What is claimed is:

1. A health evaluation system comprising:
a thermal imaging device to capture a thermal image of a human anatomy;
a medical analysis rules library database for storing a set of rules to perform a thermal mapping and automatic zoning analysis; and
a processor coupled to the thermal imaging device and configured to apply the set the rules to perform the thermal mapping and automatic zoning analysis to create thermal zones in the thermal image of the human anatomy, calculate a temperature distribution for each thermal zone, automatically evaluate temperature distribution for each thermal zone with reference to at least one of a particular temperature range, a pattern of temperature distribution, and temperature distribution in a corresponding symmetry of the each thermal zone in the human anatomy, and determine a diagnostic health condition of biological members in the each thermal zone of the human anatomy based on the evaluation, wherein in calculating and automatically evaluating the temperature distribution for each thermal zone the processor is further configured to:
generate thermal gradient sectional views of the thermal image, wherein portions in each thermal zone whose temperatures within the temperature range are identified in each thermal gradient sectional view, and wherein an upper limit and a lower limit of the temperature range are reduced by a precision factor for generating each thermal gradient sectional view, and wherein the temperature range is provided by the set of rules;
perform cascade chromatography on the gradient sectional views to generate a thermal cascade sectional view identifying areas of abnormal temperature, wherein temperature distribution of each portion identified in each thermal gradient sectional view is automatically evaluated with reference to a temperature distribution in a corresponding symmetry of the human anatomy, and wherein those portions not having same temperature distribution with reference to corresponding symmetries are identified as the areas of abnormal temperature in the thermal cascade sectional view; and
perform thermal layer sectional view on the thermal cascade sectional view for determining the diagnostic health condition of biological members, wherein a depth of heat is evaluated in the areas identified to have abnormal temperature, and wherein a relative temperature distribution of a radiation emitted or conducted by each biological member is evaluated for evaluating the depth of heat, and wherein the set of rules determine the diagnostic condition of biological members based on a pattern of the relative temperature distribution.

2. The system according to claim 1, wherein in creating the thermal zones the processor is further configured to:
vectorize the thermal image and separate at least a portion of the human anatomy represented in the thermal image from a background in the thermal image;
receive positioning reference points on the vectorized thermal image; and
apply zoning lines to the vectorized thermal image based on the received positioning referencing points to create the thermal zones, wherein the zoning lines are based on a zoning template of a medical perspective.

3. The system according to claim 1, wherein the processor is further configured to generate and display a three-dimensional (3D) representation of the human anatomy based on the evaluation of the depth of heat in the captured thermal image.

4. The system according to claim 1, wherein the processor is further configured to determine at least one of human respiratory system abnormalities, otorhinolaryngological abnormalities, cardiovascular system abnormalities, reproductive system abnormalities, respiratory system abnormalities, digestive system abnormalities, urinary system abnormalities, endocrine system abnormalities, and lymphatic system abnormalities.

5. The system according to claim 1, wherein the pattern of temperature distribution includes pattern of temperature distribution derived from patients' data stored in the medical analysis rules library database.

6. The system according to claim 1, wherein the biological members include cells, tissues, and organs in the human anatomy.

7. A computer program product including a non transitory computer readable medium having instructions for causing a computer to:
receive a thermal image of a human anatomy;
apply a thermal mapping and automatic zoning analysis to the thermal image to create thermal zones in the thermal image;
calculate a temperature distribution for each thermal zone;
automatically evaluate the temperature distribution for each thermal zone with reference to at least one of a temperature range, a pattern of temperature distribution, and temperature distribution in a corresponding symmetry of the each thermal zone in the human anatomy, wherein in automatically evaluating the temperature distribution for each thermal zone the instructions further cause the computer to:
generate thermal gradient sectional views from the thermal image having the thermal zones, wherein each thermal zone in the thermal image is automatically evaluated with reference to the temperature range, and wherein portions in each thermal zone whose temperatures within the temperature range are identified in each thermal gradient sectional view, and wherein an upper limit and a lower limit of the temperature range are reduced by a precision factor for generating each thermal gradient sectional view;
perform cascade chromatography on the gradient sectional views to generate a thermal cascade sectional view identifying areas of abnormal temperature, wherein temperature distribution of each portion identified in each thermal gradient sectional view is automatically evaluated with reference to a temperature distribution in a corresponding symmetry of the human anatomy, and wherein those portions not having same temperature distribution with reference to corresponding symmetries are identified as the areas of abnormal temperature in the thermal cascade sectional view; and
perform a thermal layer sectional view on the thermal cascade sectional view for determining the diagnostic health condition of biological members, wherein a depth of heat is evaluated in the areas identified to have abnormal temperature, and wherein a relative temperature distribution of a radiation emitted or conducted by each biological member is evaluated for evaluating the depth of heat, and wherein a set of rules in the thermal mapping and automatic zoning analysis determine the diagnostic condition of biological members based on a pattern of the relative temperature distribution; and
determine a diagnostic health condition of biological members in the each thermal zone of the human anatomy based on the evaluation.

8. The computer program product according to claim 7, wherein the instructions to apply the thermal mapping and automatic zoning in creating the thermal zones further include instructions to cause the computer to:
vectorize the thermal image and separate at least a portion of the human anatomy represented in the thermal image from a background in the thermal image;
receive positioning reference points on the vectorized thermal image; and
apply zoning lines to the vectorized thermal image based on the received positioning reference points to create the thermal zones, wherein the zoning lines are based on a zoning template of a selected medical perspective.

9. The computer program product according to claim 7, wherein the instructions further cause the computer to generate and display a three-dimensional (3D) representation of the human anatomy based on the evaluation of the depth of heat in the thermal image.

10. The computer program product according to claim 7, wherein the instructions further cause the computer to report results of the evaluation including at least one of clinical information, thermal images and corresponding analysis relating to the thermal image.

11. The computer program product according to claim 6, wherein the temperature distribution includes a relative temperature distribution of a radiation emitted or conducted by each biological member under the each thermal zone.

12. An apparatus comprising:
thermal image capturing camera for capturing a thermal image of a human anatomy;
a processor for applying thermal mapping and automatic zoning analysis to the thermal image to create thermal zones in the thermal image;
the processor for calculating a temperature distribution for each thermal zone; and
the processor for automatically evaluating the temperature distribution for each thermal zone with a predefined criteria for evaluation selected from a medical analysis rules library database and determining a diagnostic health condition of biological members in the each thermal zone of the human anatomy based on the evaluation, wherein the processor means for automatically evaluating the temperature distribution further comprises:
thermal gradient sectional view module for generating thermal gradient sectional views from the thermal image having the thermal zones, wherein each thermal zone in the thermal image is automatically evaluated with reference to the temperature range, and wherein portions in each thermal zone whose temperatures within the temperature range are identified in each thermal gradient sectional view, and wherein an upper limit and a lower limit of the temperature range are reduced by a precision factor for generating each thermal gradient sectional view;
cascade chromatography module for performing cascade chromatography on the gradient sectional views to generate a thermal cascade sectional view identifying areas of abnormal temperature, wherein temperature distribution of each portion identified in each thermal gradient sectional view is automatically evaluated with reference to a temperature distribution in a corresponding symmetry of the human anatomy, and wherein those portions not having same temperature distribution with reference to corresponding symmetries are identified as the areas of abnormal temperature in the thermal cascade sectional view; and
thermal sectional view module for performing a thermal layer sectional view on the thermal cascade sectional view for determining the diagnostic health condition of biological members, wherein a depth of heat is evaluated in the areas identified to have abnormal temperature, and wherein a relative temperature distribution of a radiation emitted or conducted by each biological member is evaluated for evaluating the depth of heat, and wherein a set of rules in the thermal mapping and automatic zoning analysis determine the diagnostic condition of biological members based on a pattern of the relative temperature distribution.

13. The apparatus according to claim 12, wherein applying thermal mapping and automatic zoning further includes:
   the processor for vectorizing the thermal image;
   the processor for separating at least a portion of the human anatomy represented in the thermal image from a background in the thermal image;
   the processor for receiving positioning reference points on the vectorized thermal image; and
   the processor for applying zoning lines to the vectorized thermal image based on the received positioning reference points to create the thermal zones, wherein the zoning lines are based on a zoning template.

14. The apparatus according to claim 12, further comprising:
   a display for displaying a three-dimensional (3D) results related to the human anatomy based on the evaluation of the depth of heat to help diagnose a human illness.

15. The apparatus according to claim 12, further comprising:
   the processor for reporting results of the evaluation including at least one of clinical information, thermal images and corresponding analysis relating to the thermal image.

16. The apparatus according to claim 12, wherein the temperature distribution includes a relative temperature distribution of a radiation emitted or conducted by each biological member under the each thermal zone.

17. A method for human health evaluation comprising:
   capturing a thermal image of a selected human anatomy area of a patient;
   applying a thermal mapping and automatic zoning analysis to the thermal image to create thermal zones in the thermal image;
   calculating a temperature distribution for each thermal zone;
   automatically evaluating the temperature distribution for each thermal zone with reference to at least one of a temperature range, a pattern of temperature distribution, and temperature distribution in a corresponding symmetry of the each thermal zone from a medical analysis rules library database, wherein in automatically evaluating the temperature distribution for each thermal zone the method further comprises:
      generating thermal gradient sectional views from the thermal image having the thermal zones, wherein each thermal zone in the thermal image is automatically evaluated with reference to the temperature range, and wherein portions in each thermal zone whose temperatures within the temperature range are identified in each thermal gradient sectional view, and wherein an upper limit and a lower limit of the temperature range are reduced by a precision factor for generating each thermal gradient sectional view;
      performing cascade chromatography on the gradient sectional views to generate a thermal cascade sectional view identifying areas of abnormal temperature, wherein temperature distribution of each portion identified in each thermal gradient sectional view is automatically evaluated with reference to a temperature distribution in a corresponding symmetry of the human anatomy, and wherein those portions not having same temperature distribution with reference to corresponding symmetries are identified as the areas of abnormal temperature in the thermal cascade sectional view; and
      performing a thermal layer sectional view on the thermal cascade sectional view for determining the diagnostic health condition of biological members, wherein a depth of heat is evaluated in the areas identified to have abnormal temperature, and wherein a relative temperature distribution of a radiation emitted or conducted by each biological member is evaluated for evaluating the depth of heat, and wherein a set of rules in the thermal mapping and automatic zoning analysis determine the diagnostic condition of biological members based on a pattern of the relative temperature distribution; and
   determining a diagnostic health condition of biological members in the each thermal zone in the selected human anatomy area of the patient based on the evaluation.

18. The method according to claim 17, wherein said step of applying the thermal mapping and automatic zoning further comprises the steps of:
   vectorizing the thermal image and separating at least a portion of the selected human anatomy represented in the thermal image from a background in the thermal image;
   receiving positioning reference points on the vectorized thermal image; and
   applying zoning lines to the vectorized thermal image based on the received positioning reference points to create the thermal zones, wherein the zoning lines are based on a zoning template of a medical perspective.

19. The method according to claim 17, further comprises the steps of:
   generating and displaying a three-dimensional (3D) representation of the selected human anatomy based on the evaluation of the depth of heat.

20. The method according to claim 17, further comprises the step of:
   reporting results of the evaluation including at least one of clinical information, thermal images and corresponding analysis relating to the thermal image.

21. The method according to claim 17, wherein the temperature distribution includes a relative temperature distribution of a radiation emitted or conducted by each biological member under the each thermal zone.

22. A computer program for thermal muscle metabolism evaluation in fitness evaluation embodied on a non transitory computer readable medium having instructions for causing a computer to:
   calculate a passive temperature distribution of a muscle area in a human anatomy from passive thermal images captured at a skin surface of the muscle area;
   calculate a symmetric passive temperature distribution of a symmetric muscle area from passive thermal images captured at a skin surface of the symmetric muscle area;
   calculate an active temperature distribution of the muscle area after the muscle area is stimulated, wherein the active temperature distribution is calculated from thermal image captured at the skin surface of the muscle area after stimulation;
   calculate a symmetric active temperature distribution of the symmetric muscle area after the symmetric muscle area is stimulated, wherein the symmetric active temperature distribution is calculated from thermal image captured at the skin surface of the symmetric muscle area after stimulation;

automatically evaluate active and passive temperature distributions using a three-dimensional thermal depth analysis algorithm, wherein an abnormality is evaluated when the active temperature distributions between the symmetric muscle areas after the stimulation are unequal or the passive temperature distributions between the symmetric muscle areas before the simulation are unequal; and determine effectiveness of fitness training regimen when there is no difference between respective temperature distributions before or after the stimulation, wherein a diagnostic condition is determined to rectify the abnormality related to the muscle growth effectiveness.

23. The computer program for thermal muscle metabolism evaluation in fitness evaluation according to claim 22, wherein the muscle area is stimulated by an exercise or an electrical stimuli.

24. The computer program for thermal muscle metabolism evaluation in fitness evaluation according to claim 22, wherein automatically evaluating the active temperature distribution with the passive temperature distribution includes evaluating with reference to at least one of a particular temperature range, a pattern of temperature distribution, and temperature distribution in the corresponding symmetric muscle area in the human anatomy.

25. A computer program for fat mapping in an anatomic zone in fitness evaluation embodied on a non transitory computer readable medium having instructions for causing a computer to:

receive passive thermal images of the anatomic zone of a human anatomy captured at a skin surface of the anatomic zone, wherein the anatomic zone includes muscle and fat;

calculate a passive temperature distribution in the anatomic zone from each of the passive thermal images;

receive active thermal images of the anatomic zone captured at the skin surface of the anatomic zone after the anatomic zone is stimulated;

calculate an active temperature distribution in the anatomic zone from each of the active thermal images;

evaluate the active temperature distribution with the passive temperature distribution using a three-dimensional thermal depth analysis algorithm to differentiate fat content from the muscle in the anatomic zone, wherein relative temperature distribution of a radiation emitted or conducted before and after the stimulation is evaluated to determine the fat content and the muscle in the anatomic zone; and determine fat content in the anatomic zone.

26. The computer program for fat mapping in an anatomic zone in fitness evaluation according to claim 25, wherein the anatomic zone is stimulated by an exercise or an electrical stimuli.

27. A computer program for thermal microcirculation metabolism evaluation in fitness evaluation embodied on a non transitory computer readable medium having instructions for causing a computer to:

receive thermal images of a micro-capillary system captured at a skin surface of hands and feet of a human anatomy;

calculate a temperature distribution in respective thermal images of the hands and the feet;

automatically evaluate respective temperature distributions of the hands and the feet for temperature variations using a three-dimensional thermal depth analysis algorithm; and determine an abnormal vascular condition if the temperature distributions of the micro-capillary system between the hands are unequal or the temperature distributions of the micro-capillary system between the feet are unequal.

28. A computer program for psychological evaluation embodied on a non transitory computer readable medium having instructions for causing a computer to:

receive thermal images captured at a skin surface of a left side and a right side of brain area of a human anatomy;

calculate temperature distribution in respective thermal images of the left side and the right side;

automatically evaluate temperature distributions in the left side and the right side of the brain area using a three-dimensional thermal depth analysis algorithm, wherein an abnormal temperature is evaluated when the temperature distributions between the left side and the right side of the brain are unequal; and determine a psychological condition based on a location of the abnormal temperature.

29. A computer program for muscle endurance evaluation in fitness evaluation embodied on a non transitory computer readable medium having instructions for causing a computer to:

receive a passive image of a human muscle area captured at a skin surface and calculate a passive temperature distribution in the passive image;

receive active images captured at the skin surface of the human muscle area at periodic intervals while stimulating the human muscle area, wherein the muscle area is stimulated by an exercise or an electrical stimuli;

calculate an active temperature distribution in each of the active images captured at periodic intervals;

calculate a rate of change in temperature between subsequent temperature distributions starting from the passive temperature distribution using a three-dimensional thermal depth analysis algorithm, wherein the human muscle area is stimulated till the temperature variation is constant; and determine a muscle type based on the rate of change in temperatures and a calculated final temperature variation.

30. The computer program for muscle endurance evaluation in fitness evaluation according to claim 29, wherein the rate of change in temperature and the final temperature variation determine whether the muscle type is suited for aerobic activities or for anaerobic activities.

31. The computer program for muscle endurance evaluation in fitness evaluation according to claim 29, wherein a damaged muscle is determined based on a temperature variation between the passive distribution and a temperature distribution of the human muscle area calculated at least twelve hours after the stimulation.

32. A computer program for lymphatic system evaluation embodied on a non transitory computer readable medium having instructions for causing a computer to:

receive a thermal image of the lymphatic system, the lymphatic system comprising lymph nodes connected by lymph vessels, lymph capillaries, and lymph ducts, wherein the thermal image is captured at a skin surface of the lymphatic system;

calculate temperature distribution in the lymphatic system from the thermal image;

evaluate the temperature distribution with reference to a standardized lymphatic system temperature distribution using a three-dimensional thermal depth analysis algorithm; and determine abnormalities in the lymph nodes based on points at which temperature differences are assessed in the evaluation.

33. The computer program for lymphatic system evaluation according to claim 32, wherein the standardized lymphatic system temperature distribution includes a pattern of temperature distribution derived from patients' lymph system data stored in a medical analysis rules library database.

* * * * *

UNITED STATES PATENT AND TRADEMARK OFFICE
CERTIFICATE OF CORRECTION

PATENT NO.         : 8,792,968 B2
APPLICATION NO.    : 11/903300
DATED              : July 29, 2014
INVENTOR(S)        : Song Xiao et al.

Page 1 of 1

It is certified that error appears in the above-identified patent and that said Letters Patent is hereby corrected as shown below:

In the claims
On col. 43, line 67, the phrase "the set the rules" should be corrected to --the set of rules--

Signed and Sealed this
Second Day of February, 2016

Michelle K. Lee
*Director of the United States Patent and Trademark Office*

(12) SUPPLEMENTAL EXAMINATION CERTIFICATE

United States Patent
Xiao et al.

(10) Number: US 8,792,968 F1
(45) Certificate Issued: Feb. 12, 2015

Control No.: 96/000,076

Filing Date: Dec. 23, 2014

Primary Examiner: Catherine S. Williams

No substantial new question of patentability is raised in the request for supplemental examination. See the Reasons for Substantial New Question of Patentability Determination in the file of this proceeding.

(56) Items of Information

OTHER DOCUMENTS

CHRISTOPHE L HERRY ET AL.: "Quantitative assessment of pain-related thermal dysfunction through clinical digital infrared thermal imaging", BIOMEDICAL ENGINEERING ONLINE, vol. 3, no. 1, 1 January 2004 (2004-01-01), page 19.

SUMIO UEMATSU ET AL.: "Quantification of thermal asymmetry", JOURNAL OF NEUROSURGERY, vol. 69, no. 4, 1 October 1988 (1988-10-01), pages 552-555.

B.F. JONES ET AL.: "Digital infrared thermal imaging of human skin", IEEE ENGINEERING IN MEDICINE AND BIOLOGY MAGAZINE, vol. 21, no. 6, 1 November 2002 (2002-11-01), pages 41-48.

The extended European search report from the European Patent Office ("EPO") issued for European patent application No. EP 07 838 686.9, dated December 18, 2013.

Amendments and arguments filed on July 9, 2014 in response to the EPO Search Report.